US012669513B2

(12) United States Patent
Virtanen et al.

(10) Patent No.: US 12,669,513 B2
(45) Date of Patent: Jun. 30, 2026

(54) MAGNETIC POINT-OF-CARE SYSTEMS AND ASSAYS FOR DETERMINING GFAP IN BIOLOGICAL SAMPLES

(71) Applicant: Abbott Laboratories, Abbott Park, IL (US)

(72) Inventors: Antti Virtanen, Ottawa (CA); Cary James Miller, Ottawa (CA); Tony Lee, Abbott Park, IL (US); Peter Karabatsos, Abbott Park, IL (US); Craig Jeffrey, Abbott Park, IL (US); Andrew Schapals, Abbott Park, IL (US); Alison Taylor, Abbott Park, IL (US)

(73) Assignee: Abbott Laboratories, Abbott Park, IL (US)

( * ) Notice: Subject to any disclaimer, the term of this patent is extended or adjusted under 35 U.S.C. 154(b) by 486 days.

(21) Appl. No.: 18/353,371

(22) Filed: Jul. 17, 2023

(65) Prior Publication Data

US 2024/0003916 A1     Jan. 4, 2024

Related U.S. Application Data

(63) Continuation of application No. PCT/US2023/069325, filed on Jun. 29, 2023.

(60) Provisional application No. 63/522,334, filed on Jun. 21, 2023, provisional application No. 63/433,134, filed on Dec. 16, 2022, provisional application No. 63/402,122, filed on Aug. 30, 2022, provisional application No. 63/356,843, filed on Jun. 29, 2022.

(51) Int. Cl.
*G01N 33/68*     (2006.01)
*G01N 33/543*     (2006.01)

(52) U.S. Cl.
CPC ... *G01N 33/6893* (2013.01); *G01N 33/54326* (2013.01); *G01N 33/54386* (2013.01); *G01N 2333/4756* (2013.01); *G01N 2470/04* (2021.08); *G01N 2800/2871* (2013.01)

(58) Field of Classification Search
CPC ....... G01N 2333/4756; G01N 2470/04; G01N 2800/2871; G01N 33/54326; G01N 33/54333; G01N 33/54386; G01N 33/6893; G01N 33/6896
See application file for complete search history.

(56) References Cited

U.S. PATENT DOCUMENTS

2012/0034633 A1     2/2012  Miller et al.
2012/0301906 A1*   11/2012  Collier .................. G01N 33/74
                                                                    436/501

FOREIGN PATENT DOCUMENTS

CN     109521004 A     3/2019
WO     2018067474 A1   4/2018

OTHER PUBLICATIONS

International Searching Authority, International Search report and Written Opinion for International Application No. PCT/US23/069325 mailed Sep. 15, 2023.

* cited by examiner

*Primary Examiner* — Jennifer Wecker
(74) *Attorney, Agent, or Firm* — Lisa Mueller; Casimir Jones SC

(57)     ABSTRACT

Disclosed herein are systems and assays that employ magnetically susceptible beads and point-of-care devices comprising magnetic immunosensors to determine the amount of glial fibrillary acidic protein (GFAP) in a biological sample obtained from a subject.

35 Claims, 10 Drawing Sheets

Specification includes a Sequence Listing.

Sample inlet

First opening

First end

Hydrophilic top layer

Hydrophobic layer with microchannel

Second end

Second opening

MAGNETIC POINT-OF-CARE SYSTEMS AND ASSAYS FOR DETERMINING GFAP IN BIOLOGICAL SAMPLES

RELATED APPLICATION INFORMATION

This application is a continuation application of International Application No. PCT/US23/69325, filed on Jun. 29, 2023, which claims priority to U.S. Application No. 63/522,334, filed on Jun. 21, 2023, and U.S. Application No. 63/433,134, filed on Dec. 16, 2022, and U.S. Application No. 63/402,122, filed on Aug. 30, 2022, and U.S. Application 63/356,843, filed on Jun. 29, 2022, the contents of each of which are herein incorporated by reference.

SEQUENCE LISTING STATEMENT

The contents of the electronic sequence listing titled 40972_601_ST26.xml (Size: 7,839 bytes; and Date of Creation: Jun. 28, 2023) is herein incorporated by reference in its entirety.

TECHNICAL FIELD

The present disclosure relates to systems and assays for determining the amount of glial fibrillary acidic protein (GFAP) in a biological sample (e.g., a blood sample such as a venous blood sample, a capillary blood sample, a finger-stick blood sample or a combination thereof) obtained from a subject. The systems and assays utilize point-of-care devices containing at least one cartridge comprising at least one magnetic immunosensor to magnetically capture, retain, and determine the amount of GFAP in a sample. The amount of GFAP in a sample can aid in the diagnosis and evaluation of whether the subject has sustained, may have sustained, or is suspected of sustaining an injury to the head, such as an acquired brain injury, such as, for example, a traumatic brain injury (TBI).

BACKGROUND

More than 5 million mild traumatic brain injuries (TBIs) occur each year in the United States alone. Much of TBI evaluation and diagnosis is based on subjective data. Unfortunately, objective measurements such as head CT and Glasgow Coma Score (GCS) are not very comprehensive or sensitive in evaluating mild TBI. Moreover, head CT is unrevealing for the vast majority of the time for mild TBI, is expensive, and exposes the patient to unnecessary radiation. Additionally, a negative head CT does not mean the patient has been cleared from having a concussion; rather it just means certain interventions, such as surgery, are not warranted. Clinicians and patients need objective, reliable information to accurately evaluate this condition to promote appropriate triage and recovery. To date, limited data have been available for the use of GFAP in the acute care setting to aid in patient evaluation and management.

Mild TBI or concussion is much harder to objectively detect and presents an everyday challenge in emergency care units globally. Concussion usually causes no gross pathology, such as hemorrhage, and no abnormalities on conventional computed tomography scans of the brain, but rather rapid-onset neuronal dysfunction that resolves in a spontaneous manner over a few days to a few weeks. Approximately 15% of mild TBI patients suffer persisting cognitive dysfunction. There is an unmet need for mild TBI victims on scene, in emergency rooms and clinics, in the sports area and in military activity (e.g., combat).

Current algorithms for assessment of the severity of brain injury include Glasgow Coma Scale score and other measures. These measures may at times be adequate for relating acute severity but are insufficiently sensitive for subtle pathology which can result in persistent deficit. GCS and other measures also do not enable differentiation among types of injury and may not be adequate. Thus, patients grouped into a single GCS level entering a clinical trial may have vastly heterogeneous severity and type of injury. Because outcomes also vary accordingly, inappropriate classification undermines the integrity of a clinical trial. Improved classification of injury will enable more precise delineation of disease severity and type for TBI patients in clinical trials.

Additionally, current brain injury trials rely on outcome measures such as Glasgow Outcome Scale Extended, which capture global phenomena but fail to assess for subtle differences in outcome. Thus 30 consecutive trials for brain injury therapeutics have failed. Sensitive outcome measures are needed to determine how well patients have recovered from brain injury in order to test therapeutics and prophylactics.

SUMMARY

In one embodiment, the present disclosure relates to an assay for measuring an amount of glial fibrillary acid protein (GFAP) in a biological sample obtained from a subject. In some aspects, the assay comprises:

(a) contacting the sample with a cartridge comprising at least one magnetic immunosensor and: (i) at least one first specific binding partner comprising at least one anti-GFAP antibody which specifically binds to GFAP in the sample that is printed on the cartridge, wherein said at least one first specific binding partner is immobilized on at least one magnetically susceptible bead; and (ii) at least one second specific binding partner comprising a detectable label that is printed on the cartridge, thereby producing one or more complexes comprising the first specific binding partner-GFAP-second specific binding partner;

(b) magnetically capturing and retaining the bead containing the complexes on at least one magnetic immunosensor in cartridge contained in a point-of-care device; and (c) assessing a signal from the complexes using the at least one magnetic immunosensor, wherein the amount of detectable signal from the detectable label indicates the amount of GFAP in the sample, where the assay exhibits at least a 5-fold increase in sensitivity compared to an assay that does not immobilize the first specific binding partner on a magnetically susceptible bead and magnetically capture and retain the bead containing the complexes on at least one magnetic immunosensor in a cartridge contained in a point-of-care device.

In further aspects, the above assay further comprises the step of washing unbound sample that is not magnetically captured and retained on the at least one magnetic immunosensor.

In still further aspects of the above assay, the magnetic immunosensor comprises a sensing electrode on a substantially planar chip and a magnetic layer on the chip. More specifically, in still further aspects, the magnetic layer comprises high-field magnetic particles.

In still further aspects of the above assay, the assay further comprises measuring an amount of ubiquitin carboxy-terminal hydrolase L1 (UCH-L1) in the sample in a non-magnetic assay.

In still further aspects of the above assay, the assay exhibits at least a 7-fold, at least an 8-fold, at least a 9-fold, at least a 10-fold, at least a 11-fold, at least a 12-fold, at least a 13-fold, at least a 14-fold, or at least a 15-fold increase in sensitivity compared to an assay that does not immobilize the first specific binding partner on a magnetically susceptible bead and magnetically capture and retain the bead containing the complexes on at least one magnetic immunosensor in a cartridge contained in a point-of-care device.

In yet further aspects, the above assay is used to aid in a diagnosis and evaluation of a subject that has sustained or may have sustained an injury to the head. In some aspects, the subject is diagnosed as having an acquired brain injury. In still further aspects, the subject is diagnosed as having a traumatic brain injury. In still further aspects, the subject is treated for the traumatic brain injury.

In still further aspects of the above assay, the sample is collected using a microsampling device or a fingerstick device. In some aspects, the sample collected is a venous blood sample, a capillary blood sample, a fingerstick blood sample or a combination thereof.

In yet further aspects, the sample is processed prior to performing the assay. In some aspects, the sample is processed by plasma separation. In some aspects, the sample is processed using a plasma separation device. In still further aspects, the plasma separation device is: (a) incorporated into or operably linked to the point-of-care device; or (b) separate from the point-of-care device.

In yet still further aspects, the amount of GFAP is communicated by displaying on the device.

In still yet further aspects, prior to displaying the amount of the GFAP on the device, the assay further comprises:

a. determining the amount or of GFAP in the capillary blood sample;

b. selecting a conversion factor for comparing the amount of GFAP in the sample with the amount of the GFAP in venous blood, wherein the conversion factor is a static correlation ratio, a dynamic ratio or a combination thereof; and c. normalizing the amount of GFAP in the sample with the amount of GFAP from venous blood by applying the conversion factor selected in step b) to the amount of GFAP in the sample.

In still further aspects, conversion factor is from about 1.2:1.0 to about 1.0:0.5. In other aspects, the conversion factor is from about 1.0:0.85.

In yet further aspects, if a conversion factor is employed, a normalized amount of GFAP is displayed by the device.

In another embodiment, the present disclosure relates to a system. In some aspects, the system comprises:

an assay for glial fibrillary acidic protein (GFAP), wherein the assay comprises contacting a biological sample from a subject with a cartridge comprising at least one magnetic immunosensor and: (i) at least one first specific binding partner comprising at least one anti-GFAP antibody which specifically binds to GFAP in the sample that is printed on the cartridge, wherein said at least one first specific binding partner is immobilized on at least one magnetically susceptible bead; and (ii) at least one second specific binding partner comprising a detectable label that is printed on the cartridge, thereby producing one or more complexes comprising the first specific binding partner-GFAP-second specific binding partner;

a point-of-care device comprising a cartridge, wherein the cartridge comprises at least one magnetic immunosensor, wherein the device (a) determines an amount of GFAP in a sample obtained from the subject by magnetically capturing and retaining the bead containing the complexes on the at least one magnetic immunosensor; and (b) assesses a signal from the complexes, wherein the amount of detectable signal from the detectable label indicates the amount of GFAP in the sample, where the assay exhibits at least a 5-fold increase in sensitivity compared to an assay that does not immobilize the first specific binding partner on a magnetically susceptible bead and magnetically capture and retain the bead containing the complexes on at least one magnetic immunosensor in a cartridge contained in a point-of-care device.

In further aspects, the above system further comprises the step of washing unbound sample that is not magnetically captured and retained on the at least one magnetic immunosensor.

In still further aspects of the above system, the magnetic immunosensor comprises a sensing electrode on a substantially planar chip and a magnetic layer on the chip. More specifically, in still further aspects, the magnetic layer comprises high-field magnetic particles.

In still further aspects of the above system, the assay further comprises measuring an amount of ubiquitin carboxy-terminal hydrolase L1 (UCH-L1) in the sample in a non-magnetic assay.

In still further aspects of the above system, the assay exhibits at least a 7-fold, at least an 8-fold, at least a 9-fold, at least a 10-fold, at least a 11-fold, at least a 12-fold, at least a 13-fold, at least a 14-fold, or at least a 15-fold increase in sensitivity compared to an assay that does not immobilize the first specific binding partner on a magnetically susceptible bead and magnetically capture and retain the bead containing the complexes on at least one magnetic immunosensor in a cartridge contained in a point-of-care device.

In yet further aspects, the above system is used to aid in a diagnosis and evaluation of a subject that has sustained or may have sustained an injury to the head. In some aspects, the subject is diagnosed as having an acquired brain injury. In still further aspects, the subject is diagnosed as having a traumatic brain injury. In still further aspects, the subject is treated for an acquired brain injury. In yet still further aspects, the subject is treated for the traumatic brain injury.

In still further aspects of the above system, the sample is collected using a microsampling device or a fingerstick device. In some aspects, the sample collected is a venous blood sample, a capillary blood sample, a fingerstick blood sample or a combination thereof.

In yet further aspects, the sample is processed prior to performing the assay. In some aspects, the sample is processed by plasma separation. In some aspects, the sample is processed using a plasma separation device. In still further aspects, the plasma separation device is: (a) incorporated into or operably linked to the point-of-care device; or (b) separate from the point-of-care device.

In yet still further aspects, the amount of GFAP is communicated by displaying on the device.

In another embodiment, the present disclosure relates to a cartridge comprising:

a magnet;

an area comprising printed paramagnetic particles coated with an anti-GFAP antibody; and an area comprising a plurality of printed detectably labeled anti-GFAP antibodies, wherein the cartridge is used in a point-of-care device.

In some aspects in the cartridge, the area comprising the plurality of detectably labeled anti-GFAP antibodies is in the same area containing the printed paramagnetic particles coated with the anti-GFAP antibody.

In other aspects in the cartridge, the area comprising the plurality of detectably labeled anti-GFAP antibodies is adjacent to the area containing the printed paramagnetic particles coated with the anti-GFAP antibody.

BRIEF DESCRIPTION OF THE DRAWINGS

FIG. 1 shows a GFAP assay that uses a magnetically susceptible bead and is magnetically captured and retained on a magnet as described in Example 1.

DETAILED DESCRIPTION

Figure 2:
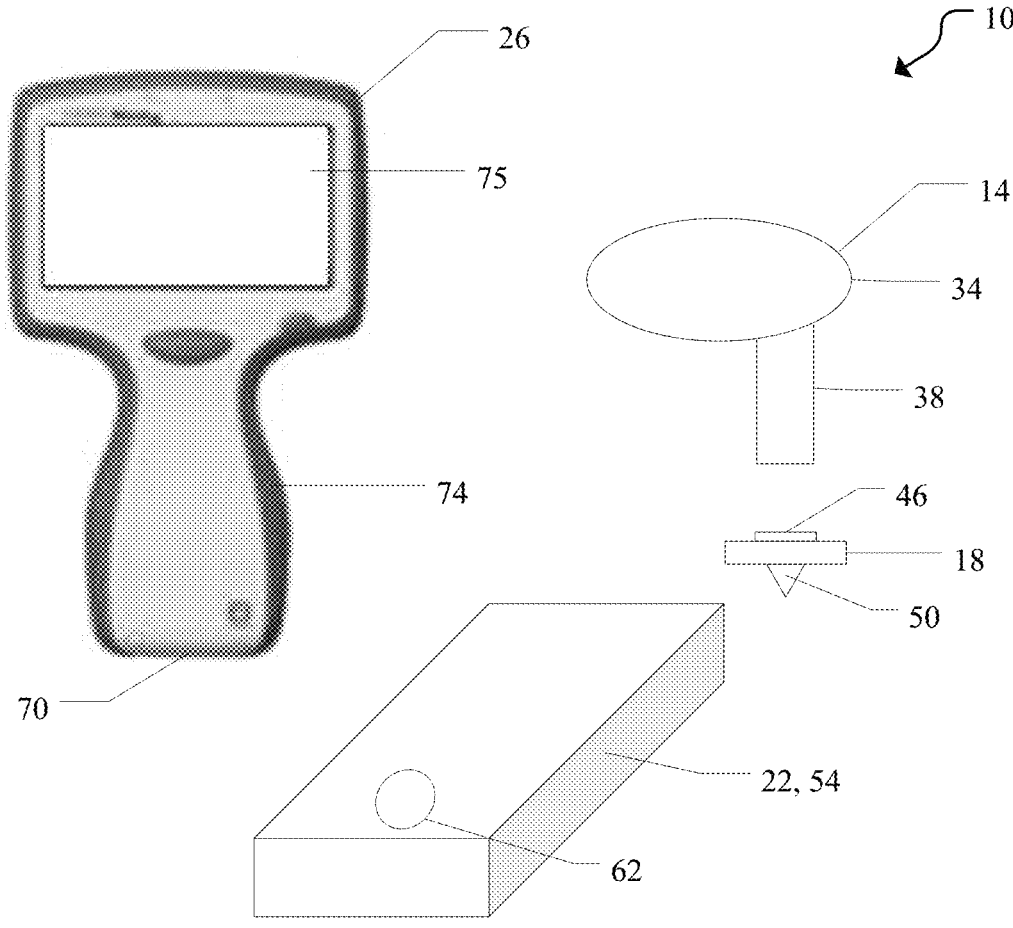
FIG. 2 shows a system for diagnosis and evaluation of a subject that has sustained or may have sustained an injury to the head according to one aspect of the disclosure.

The present disclosure relates to systems and methods (e.g., assays) for determining the amount of glial fibrillary acidic protein (GFAP) in a biological sample, such as a blood sample (e.g., a venous blood sample, a capillary blood sample, a fingerstick blood sample, or any combinations thereof) obtained from a subject (e.g., such as a human subject). The systems and methods described herein employ at least one point-of-care device containing at least one cartridge comprising at least one magnetic immunosensor or immunosensing device.

In some aspects, the systems and methods involve performing an assay for GFAP which comprises contacting a biological sample, such as blood (e.g., a venous blood sample, a capillary blood sample, a fingerstick blood sample, or any combinations thereof), with a cartridge comprising at least one magnetic immunosensor and (i) at least one first specific binding partner comprising at least one anti-GFAP antibody which specifically binds to GFAP in the sample that is printed on the cartridge, where the at least one first specific binding partner is immobilized on at least one magnetically susceptible bead and (ii) at least one second specific binding partner comprising a detectable label that is printed on the cartridge to produce one or more complexes comprising the first specific binding partner-GFAP-second specific binding partner. The point-of-care device contains the at least one cartridge which is used to magnetically capture and retain the bead containing the complexes using the at least one magnetic immunosensor and the signal from the complexes assessed, wherein the amount of detectable signal from the detectable label indicates the amount of GFAP in the sample. The GFAP assay performed and used in the systems described herein exhibits at least a 5-fold increase in sensitivity when compared to an assay that does not immobilize the first specific binding partner on a magnetically susceptible bead and use a point-of-care device comprising a cartridge containing at least one magnetic immunosensor.

Section headings as used in this section and the entire disclosure herein are merely for organizational purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Acquired brain injury" or (ABI) as used herein refers to damage to the brain that is caused by events occurring after birth. In other words, acquired brain injuries are not genetic or congenital but are the result neurological conditions and injuries. Acquired brain injuries are often divided into two categories. The first category is acquired traumatic brain injuries (TBI), that occur due to an external force, such as, for example, a sports injury, fall, physical shaking, blunt force trauma, explosion, blast, or exposure to a fire. The second category is non-traumatic acquired brain injuries that in some cases are caused by internal factors and include stroke, tumors, anoxia, infections, metabolic disorders, and others. As used herein, an acquired brain injury does not include or encompass damage to the brain that is caused by a stroke (including, such as, for example, ischemic stroke, hemorrhagic stroke, or a transient ischemic attack, etc.).

"Affinity matured antibody" is used herein to refer to an antibody with one or more alterations in one or more CDRs, which result in an improvement in the affinity (i.e., $K_D$, $k_d$ or $k_a$) of the antibody for a target antigen compared to a parent antibody, which does not possess the alteration(s). Exemplary affinity matured antibodies will have nanomolar or even picomolar affinities for the target antigen. A variety of procedures for producing affinity matured antibodies is known in the art, including the screening of a combinatory antibody library that has been prepared using bio-display. For example, Marks et al., *BioTechnology*, 10: 779-783 (1992) describes affinity maturation by VH and VL domain shuffling. Random mutagenesis of CDR and/or framework residues is described by Barbas et al., *Proc. Nat. Acad. Sci. USA*, 91: 3809-3813 (1994); Schier et al., *Gene*, 169: 147-155 (1995); Yelton et al., *J. Immunol.*, 155: 1994-2004 (1995); Jackson et al., *J. Immunol.*, 154(7): 3310-3319 (1995); and Hawkins et al, *J. Mol. Biol.*, 226: 889-896 (1992). Selective mutation at selective mutagenesis positions and at contact or hypermutation positions with an activity-enhancing amino acid residue is described in U.S. Pat. No. 6,914,128 B1.

An "amount" as used herein refers to a quantity specified (e.g., high or low) or a number e.g., where the number is a level, such as a position on a real or imaginary scale of amount or quantity, or a concentration, such as, for example, a relative amount of a given substance contained within a solution or in a particular volume of space, e.g., the amount of solute per unit volume of solution.

"Antibody" and "antibodies" as used herein refers to monoclonal antibodies, multispecific antibodies, human antibodies, humanized antibodies (fully or partially humanized), animal antibodies such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, F(ab')₂ fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., *Nature Biotechnology*, 25(11):1290-1297 (2007) and PCT International Application WO 2001/058956, the contents of each of which are herein incorporated by reference), and functionally active epitope-binding fragments of any of the above. Antibodies include immunoglobulin molecules and immunologically active fragments of immunoglobulin molecules, namely, molecules that contain an analyte-binding site. Immunoglobulin molecules can be of any type (for example, IgG, IgE, IgM, IgD, IgA, and IgY), class (for example, IgG1, IgG2, IgG3, IgG4, IgA1, and IgA2), or subclass. For simplicity sake, an antibody against an analyte is frequently referred to herein as being either an "anti-analyte antibody" or merely an "analyte antibody" (e.g., an anti-UCH-L1 antibody or a UCH-L1 antibody).

"Antibody fragment" as used herein refers to a portion of an intact antibody comprising the antigen-binding site or variable chain region. The portion does not include the constant heavy chain domains (i.e., CH2, CH3, or CH4, depending on the antibody isotype) of the Fc region of the intact antibody. Examples of antibody fragments include, but are not limited to, Fab fragments, Fab' fragments, Fab'-SH fragments, F(ab')₂ fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Aperture" as used herein refers to an opening, hole, or gap.

The "area under curve" or "AUC" refers to area under a ROC curve. AUC under a ROC curve is a measure of accuracy. An AUC of 1 represents a perfect test, whereas an AUC of 0.5 represents an insignificant test. A preferred AUC may be at least approximately 0.700, at least approximately 0.750, at least approximately 0.800, at least approximately 0.850, at least approximately 0.900, at least approximately 0.910, at least approximately 0.920, at least approximately 0.930, at least approximately 0.940, at least approximately 0.950, at least approximately 0.960, at least approximately 0.970, at least approximately 0.980, at least approximately 0.990, or at least approximately 0.995.

"Bead" and "particle" are used herein interchangeably and refer to a substantially spherical solid support. One example of a bead or particle is a microparticle. Microparticles that can be used herein can be any type known in the art. For example, the bead or particle can be a magnetically susceptible (or responsive) bead or particle (See, for example, U.S. Pat. Nos. 4,230,685 4,554,088 and 4,628,037, all of which are herein incorporated by reference) or magnetic particle, as used interchangeable herein. Another example of a bead or particle is a magnetic or magnetically susceptible beads or particles.

"Binding protein" is used herein to refer to a monomeric or multimeric protein that binds to and forms a complex with a binding partner, such as, for example, a polypeptide, an antigen, a chemical compound or other molecule, or a substrate of any kind. A binding protein specifically binds a binding partner. Binding proteins include antibodies, as well as antigen-binding fragments thereof and other various forms and derivatives thereof as are known in the art and described herein below, and other molecules comprising one or more antigen-binding domains that bind to an antigen molecule or a particular site (epitope) on the antigen molecule. Accordingly, a binding protein includes, but is not limited to, an antibody a tetrameric immunoglobulin, an IgG molecule, an IgG1 molecule, a monoclonal antibody, a chimeric antibody, a CDR-grafted antibody, a humanized antibody, an affinity matured antibody, and fragments of any such antibodies that retain the ability to bind to an antigen.

"Bispecific antibody" is used herein to refer to a full-length antibody that is generated by quadroma technology (see Milstein et al., *Nature*, 305(5934): 537-540 (1983)), by chemical conjugation of two different monoclonal antibodies (see, Staerz et al., *Nature*, 314(6012): 628-631 (1985)), or by knob-into-hole or similar approaches, which introduce mutations in the Fc region (see Holliger et al., *Proc. Natl. Acad. Sci. USA*, 90(14): 6444-6448 (1993)), resulting in multiple different immunoglobulin species of which only one is the functional bispecific antibody. A bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen-binding arms (in both specificity and CDR sequences) and is monovalent for each antigen to which it binds to.

"Capillary blood sample" as used herein refers to a sample of blood from the capillaries which is obtained (e.g., extracted) through the skin (and not the veins) of a subject using a syringe, needle, or any other suitable device or combination thereof. For example, a whole blood sample can be obtained from the skin on the fingers and/or toes, a hand, a foot (including the heel), an earlobe, a location on the arms and/or legs, chest, back, head, or any combinations thereof. In other aspects, the whole capillary blood sample is extracted from the arms or legs. In still other aspects, the capillary blood sample is obtained from the hands or feet. In still other aspects, the capillary blood sample is obtained from the chest or back. In yet other aspects, the capillary blood sample is obtained from an earlobe. In still other aspects, the capillary blood sample is obtained from the head.

In further aspects, the capillary blood sample is whole blood, serum or plasma. In yet other embodiments, the capillary blood sample contains predominantly capillary blood, but may also contain or comprise a small amount or percentage of interstitial fluid.

In still further aspects, the capillary blood sample obtained from the subject is obtained without the use of a syringe, needle (e.g., 21-gauge needle, a butterfly needle, etc.), or any other suitable device, or any combination thereof which are typically used to draw blood (e.g., venous blood). Instead, the capillary blood sample is obtained using a self- or other-administered blood collection device. Examples of self- or other-administered blood collection devices include microsampling devices. Example microsampling devices which can be used herein include the TAP device available from YourBio Health, Inc. (Cambridge, MA) as well as the device described in U.S. Pat. No. 9,113,836, the contents of which are herein incorporated by reference, the Tasso+, Tasso-M20, and Tasso-ST devices available from Tasso, Inc. (Seattle, WA), the One Draw device available from Draw Bridge Health (San Diego, CA), PBS-1000 from PreciHealth (Neuchatel, Switzerland) or the Loop blood collection device available from Loop Medical (Lausanne, Switzerland).

In yet further aspects, the capillary blood sample is obtained or collected from a subject in a decentralized setting. For example, the capillary blood sample can be obtained or collected from an urgent care clinic, a pharmacy, a grocery or other convenience store, a residence, a workplace, and/or a government office.

In addition or alternatively, in still yet further aspects, the capillary blood sample is obtained from the subject by a user who is not trained in collecting blood (e.g., by someone other than a trained phlebotomist, a nurse, a medical assistant and/or physician). For example, the capillary blood sample can be obtained by the subject him or herself, a relative, friend, a co-worker, a coach, a pharmacist, and/or any other individual. In still yet further aspects, the capillary blood sample is obtained from a subject by a robot.

In yet still further aspects, the capillary blood sample obtained from the subject is in an amount of less than about 4 mL. In some aspects, the capillary blood sample obtained from the subject is less than about 3 mL. In some aspects, the capillary blood sample obtained from the subject is less than about 2 mL. In some aspects, the amount of capillary blood sample obtained from the subject is less than about 3.9 mL, about 3.8 mL, about 3.7 mL, about 3.6 mL, about 3.5 mL, about 3.4 mL, about 3.3 mL, about 3.2 mL, about 3.1 mL, about 3.0 mL, about 2.9 mL, about 2.8 mL, about 2.7 mL, about 2.6 mL, about 2.5 mL, about 2.4 mL, about 2.3 mL, about 2.2 mL, about 2.1 mL, about 2.0 ml, about 1.9 mL, about 1.8 mL, about 1.7 mL, about 1.6 mL, about 1.5 mL, about 1.4 mL, about 1.3 mL, about 1.2 mL, about 1.1 mL, about 1.0 mL, about 0.9 mL, about 0.8 mL, about 0.7 mL, about 0.6 mL, or about 0.5 mL. In some aspects, higher volumes of capillary blood may be obtained when the sample collected is whole blood.

"Cartridge" as used herein refers to a hollow container and/or chip that comprises one or more substances and/or components (e.g., a liquid, reagents (e.g, antibodies and/or antigens), and/or a particle (e.g., a bead, or microparticle)) for insertion into an apparatus (e.g., a point-of-care device). In some aspects, the cartridge comprises at least one chip. In other aspects, the cartridge is a chip. In still further aspects, the cartridge has one or more apertures. In some aspects, a cartridge is a microfluidic cartridge. In other aspects, the cartridge contains a magnetic immunosensor or magnetic immunosensing device.

"Coupled" or "linked" as used herein refers to two or more components that are secured, by any suitable means, together. Accordingly, in some embodiments, the statement that two or more parts or components are "coupled" shall mean that the parts are joined or operate together either directly or indirectly, e.g., through one or more intermediate parts or components.

"CDR" is used herein to refer to the "complementarity determining region" within an antibody variable sequence. There are three CDRs in each of the variable regions of the heavy chain and the light chain. Proceeding from the N-terminus of a heavy or light chain, these regions are denoted "CDR1", "CDR2", and "CDR3", for each of the variable regions. The term "CDR set" as used herein refers to a group of three CDRs that occur in a single variable region that binds the antigen. An antigen-binding site, therefore, may include six CDRs, comprising the CDR set from each of a heavy and a light chain variable region. A polypeptide comprising a single CDR, (e.g., a CDR1, CDR2, or CDR3) may be referred to as a "molecular recognition unit." Crystallographic analyses of antigen-antibody complexes have demonstrated that the amino acid residues of CDRs form extensive contact with bound antigen, wherein the most extensive antigen contact is with the heavy chain CDR3. Thus, the molecular recognition units may be primarily responsible for the specificity of an antigen-binding site. In general, the CDR residues are directly and most substantially involved in influencing antigen binding.

The exact boundaries of these CDRs have been defined differently according to different systems. The system described by Kabat (Kabat et al., *Sequences of Proteins of Immunological Interest* (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as "Kabat CDRs". Chothia and coworkers (Chothia and Lesk, *J. Mol. Biol.,* 196: 901-917 (1987); and Chothia et al., *Nature,* 342: 877-883 (1989)) found that certain sub-portions within Kabat CDRs adopt nearly identical peptide backbone conformations, despite having great diversity at the level of amino acid sequence. These sub-portions were designated as "L1", "L2", and "L3", or "H1", "H2", and "H", where the "L" and the "H" designate the light chain and the heavy chain regions, respectively. These regions may be referred to as "Chothia CDRs", which have boundaries that overlap with Kabat CDRs. Other boundaries defining CDRs overlapping with the Kabat CDRs have been described by Padlan, *FASEB J.,* 9: 133-139 (1995), and MacCallum, *J. Mol. Biol.,* 262(5): 732-745 (1996). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat- or Chothia-defined CDRs.

A "clinically-relevant time frame" refers to a time frame (e.g., seconds, minutes, or hours) during which a careful and prudent medical practitioner (e.g., doctor, nurse, paramedic, or other) would reasonably consider the results of one or more biomarker tests to have bearing on an imaging procedure, such as a head CT scan, or pursuant to guidelines established by an overseeing entity (e.g., a standards-setting body such as the World Health Organization (WHO), physicians review board, regulatory approval authority such as FDA, EMEA or other, etc.).

"Component," "components," or "at least one component," refer generally to a capture antibody, a detection or conjugate a calibrator, a control, a sensitivity panel, a container, a buffer, a diluent, a salt, an enzyme, a co-factor for an enzyme, a detection reagent, a pretreatment reagent/ solution, a substrate (e.g., as a solution), a stop solution, and the like that can be included in a kit for assay of a test sample, such as a patient whole blood, serum or plasma sample, in accordance with the methods described herein and other methods known in the art. Some components can be in solution or lyophilized for reconstitution for use in an assay.

"Correlated to" as used herein refers to compared to.

"CT scan" as used herein refers to a computerized tomography (CT) scan. A CT scan combines a series of X-ray images taken from different angles and uses computer processing to create cross-sectional images, or slices, of the bones, blood vessels and soft tissues inside your body. The CT scan may use X-ray CT, positron emission tomography (PET), single-photon emission computed tomography (SPECT), computed axial tomography (CAT scan), or computer aided tomography. The CT scan may be a conventional CT scan or a spiral/helical CT scan. In a conventional CT scan, the scan is taken slice by slice and after each slice the scan stops and moves down to the next slice, e.g., from the top of the abdomen down to the pelvis. The conventional CT scan requires patients to hold their breath to avoid movement artefact. The spiral/helical CT scan is a continuous scan which is taken in a spiral fashion and is a much quicker process where the scanned images are contiguous.

A head CT scan is "negative" for a TBI when no intracranial lesion(s) is observed in an image taken from a subject that has sustained, may have sustained or is suspected of sustaining an injury to the head. To further clarify, the head CT scan of a subject is "negative" for a TBI when a lesion is not found or identified; however, in some aspects, the subject may still be experiencing symptoms (e.g., of TBI) even though the head CT is negative. Most subjects will be negative for a TBI on head CT given that not all injuries or lesions can be visualized by head CT. Consequently, the methods and assays described herein can be used to provide an assessment or determination of a subject with a negative head CT that may still have a TBI.

"Curie point" or "Curie temperature" as used interchangeably herein, refers to a characteristic property of a ferromagnetic material. The Curie point of a ferromagnetic material is the temperature above which it loses its characteristic ferromagnetic ability to possess a net (spontaneous) magnetization in the absence of an external magnetic field. At temperatures below the Curie point, the magnetic moments are partially aligned within magnetic domains in ferromagnetic materials. As the temperature is increased from below the Curie point, thermal fluctuations increasingly destroy this alignment, until the net magnetization becomes zero at and above the Curie point. Above the Curie point, the material is purely paramagnetic.

"Decentralize", "Decentralized", or "Decentralization", as used interchangeably herein, refers to, in the context of testing, the performance of one or more medical tests and/or assays outside of a traditional medical setting (e.g., a hospital, physician office, stand alone lab site, etc.) to one or more places such as urgent care clinics, retail clinics, pharmacies, grocery stores or convenience stores, residences (e.g., homes, apartments, etc.), workplaces, and/or government offices (e.g., U.S. Transportation and Safety Authority), etc. "Hybrid-decentralization" or "hybrid-decentralized" refers to situations in which a subject or patient collects a sample at a residence and/or workplace and ships the sample to a laboratory, avoiding a professional collection site (such as a hospital, physician's office, or stand alone sample collection or lab site).

"Determined by an assay" is used herein to refer to the determination of a reference level by any appropriate assay. The determination of a reference level may, in some embodiments, be achieved by an assay of the same type as the assay that is to be applied to the sample from the subject (for example, by an immunoassay, clinical chemistry assay, a single molecule detection assay, protein immunoprecipitation, immunoelectrophoresis, chemical analysis, SDS-PAGE and Western blot analysis, or protein immunostaining, electrophoresis analysis, a protein assay, a competitive binding assay, a functional protein assay, or chromatography or spectrometry methods, such as high-performance liquid chromatography (HPLC) or liquid chromatography-mass spectrometry (LC/MS)). The determination of a reference level may, in some embodiments, be achieved by an assay of the same type and under the same assay conditions as the assay that is to be applied to the sample from the subject. As noted herein, this disclosure provides exemplary reference levels (e.g., calculated by comparing reference levels at different time points). It is well within the ordinary skill of one in the art to adapt the disclosure herein for other assays to obtain assay-specific reference levels for those other assays based on the description provided by this disclosure. For example, a set of training samples comprising samples obtained from human subjects known to have sustained an injury to the head (and more particularly, samples obtained from human subjects known to have sustained a (i) mild TBI; and/or (ii) moderate, severe, or moderate to severe TBI and samples obtained from human subjects known not to have sustained an injury to the head may be used to obtain assay-specific reference levels. It will be understood that a reference level "determined by an assay" and having a recited level of "sensitivity" and/or "specificity" is used herein to refer to a reference level which has been determined to provide a method of the recited sensitivity and/or specificity when said reference level is adopted in the methods of the disclosure. It is well within the ordinary skill of one in the art to determine the sensitivity and specificity associated with a given reference level in the methods of the disclosure, for example by repeated statistical analysis of assay data using a plurality of different possible reference levels.

Practically, when discriminating between a subject as having a traumatic brain injury or not having a traumatic brain injury or a subject as having a mild versus a moderate, severe, or moderate to severe traumatic brain injury, the skilled person will balance the effect of raising a cutoff on sensitivity and specificity. Raising or lowering a cutoff will have a well-defined and predictable impact on sensitivity and specificity, and other standard statistical measures. It is well known that raising a cutoff will improve specificity but is likely to worsen sensitivity (proportion of those with disease who test positive). In contrast, lowering a cutoff will improve sensitivity but will worsen specificity (proportion of those without disease who test negative). The ramifications for detecting traumatic brain injury or determining a mild versus moderate, severe, or moderate to severe traumatic brain injury will be readily apparent to those skilled in the art. In discriminating whether a subject has or does not have a traumatic brain injury or a mild versus a moderate, severe, or moderate to severe traumatic brain injury, the higher the cutoff, specificity improves as more true negatives (i.e., subjects not having a traumatic brain injury, not having a mild traumatic brain injury, not have a moderate traumatic brain injury, not having a severe traumatic brain injury or not having a moderate to severe traumatic brain injury) are distinguished from those having a traumatic brain injury, a mild traumatic brain injury, a moderate traumatic brain injury, a severe traumatic brain injury or a moderate to severe traumatic brain injury. But at the same time, raising the cutoff decreases the number of cases identified as positive overall, as well as the number of true positives, so the sensitivity must decrease. Conversely, the lower the cutoff, sensitivity improves as more true positives (i.e., subjects having a traumatic brain injury, having a mild traumatic brain injury, having a moderate traumatic brain injury, having a severe traumatic brain injury or having a moderate to severe traumatic brain injury) are distinguished from those who do not have a traumatic brain injury, a mild traumatic brain injury, a moderate traumatic brain injury, a severe traumatic brain injury or a moderate to severe traumatic brain injury. But at the same time, lowering the cutoff increases the number of cases identified as positive overall, as well as the number of false positives, so the specificity must decrease.

Generally, a high sensitivity value helps one of skill rule out disease or condition (such as a traumatic brain injury, mild traumatic brain injury, moderate traumatic brain injury, severe traumatic brain injury or moderate to severe traumatic brain injury), and a high specificity value helps one of skill rule in disease or condition. Whether one of skill desires to rule out or rule in disease depends on what the consequences are for the patient for each type of error. Accordingly, one cannot know or predict the precise balancing employed to derive a test cutoff without full disclosure of the underlying information on how the value was selected. The balancing of sensitivity against specificity and other factors will differ on a case-by-case basis. This is why it is sometimes preferable to provide alternate cutoff (e.g., reference) values so a physician or practitioner can choose.

"Derivative" of an antibody as used herein may refer to an antibody having one or more modifications to its amino acid sequence when compared to a genuine or parent antibody and exhibit a modified domain structure. The derivative may still be able to adopt the typical domain configuration found in native antibodies, as well as an amino acid sequence, which is able to bind to targets (antigens) with specificity. Typical examples of antibody derivatives are antibodies coupled to other polypeptides, rearranged antibody domains, or fragments of antibodies. The derivative may also comprise at least one further compound, e.g., a protein domain, said protein domain being linked by covalent or non-covalent bonds. The linkage can be based on genetic fusion according to the methods known in the art. The additional domain present in the fusion protein comprising the antibody may preferably be linked by a flexible linker, advantageously a peptide linker, wherein said peptide linker comprises plural, hydrophilic, peptide-bonded amino acids of a length sufficient to span the distance between the C-terminal end of the further protein domain and the N-terminal end of the antibody or vice versa. The antibody may be linked to an effector molecule having a conformation suitable for biological activity or selective binding to a solid support, a biologically active substance (e.g., a cytokine or growth hormone), a chemical agent, a peptide, a protein, or a drug, for example.

"Drugs of abuse" is used herein to refer to one or more additive substances (such as a drug) taken for non-medical reasons (such as for, example, recreational and/or mind-altering effects). Excessive overindulgence, use or dependence of such drugs of abuse is often referred to as "substance abuse". Examples of drugs of abuse include alcohol, barbiturates, benzodiazepines, cannabis, cocaine, hallucinogens (such as ketamine, mescaline (peyote), PCP, psilocybin, DMT and/or LSD), methaqualone, opioids, amphetamines (including methamphetamines), anabolic steroids, inhalants (namely, substances which contain volatile substances that contain psychoactive properties such as, for example, nitrites, spray paints, cleaning fluids, markers, glues, etc.) and combinations thereof.

"Dual-specific antibody" is used herein to refer to a full-length antibody that can bind two different antigens (or epitopes) in each of its two binding arms (a pair of HC/LC) (see PCT publication WO 02/02773). Accordingly, a dual-specific binding protein has two identical antigen binding arms, with identical specificity and identical CDR sequences, and is bivalent for each antigen to which it binds.

"Dual variable domain" is used herein to refer to two or more antigen binding sites on a binding protein, which may be divalent (two antigen binding sites), tetravalent (four antigen binding sites), or multivalent binding proteins. DVDs may be monospecific, i.e., capable of binding one antigen (or one specific epitope), or multispecific, i.e., capable of binding two or more antigens (i.e., two or more epitopes of the same target antigen molecule or two or more epitopes of different target antigens). A preferred DVD binding protein comprises two heavy chain DVD polypeptides and two light chain DVD polypeptides and is referred to as a "DVD immunoglobulin" or "DVD-Ig." Such a DVD-Ig binding protein is thus tetrameric and reminiscent of an IgG molecule but provides more antigen binding sites than an IgG molecule. Thus, each half of a tetrameric DVD-Ig molecule is reminiscent of one half of an IgG molecule and comprises a heavy chain DVD polypeptide and a light chain DVD polypeptide, but unlike a pair of heavy and light chains of an IgG molecule that provides a single antigen binding domain, a pair of heavy and light chains of a DVD-Ig provide two or more antigen binding sites.

Each antigen binding site of a DVD-Ig binding protein may be derived from a donor ("parental") monoclonal antibody and thus comprises a heavy chain variable domain (VH) and a light chain variable domain (VL) with a total of six CDRs involved in antigen binding per antigen binding site. Accordingly, a DVD-Ig binding protein that binds two different epitopes (i.e., two different epitopes of two different antigen molecules or two different epitopes of the same antigen molecule) comprises an antigen binding site derived from a first parental monoclonal antibody and an antigen binding site of a second parental monoclonal antibody.

A description of the design, expression, and characterization of DVD-Ig binding molecules is provided in PCT Publication No. WO 2007/024715, U.S. Pat. No. 7,612,181, and Wu et al., *Nature Biotech.*, 25: 1290-1297 (2007). A preferred example of such DVD-Ig molecules comprises a heavy chain that comprises the structural formula VD1-(X1)n-VD2-C—(X2)n, wherein VD1 is a first heavy chain variable domain, VD2 is a second heavy chain variable domain, C is a heavy chain constant domain, X1 is a linker with the proviso that it is not CH1, X2 is an Fc region, and n is 0 or 1, but preferably 1; and a light chain that comprises the structural formula VD1-(X1)n-VD2-C—(X2)n, wherein VD1 is a first light chain variable domain, VD2 is a second light chain variable domain, C is a light chain constant domain, X1 is a linker with the proviso that it is not CH1, and X2 does not comprise an Fc region; and n is 0 or 1, but preferably 1. Such a DVD-Ig may comprise two such heavy chains and two such light chains, wherein each chain comprises variable domains linked in tandem without an intervening constant region between variable regions, wherein a heavy chain and a light chain associate to form tandem functional antigen binding sites, and a pair of heavy and light chains may associate with another pair of heavy and light chains to form a tetrameric binding protein with four functional antigen binding sites. In another example, a DVD-Ig molecule may comprise heavy and light chains that each comprise three variable domains (VD1, VD2, VD3) linked in tandem without an intervening constant region between variable domains, wherein a pair of heavy and light chains may associate to form three antigen binding sites, and wherein a pair of heavy and light chains may associate with another pair of heavy and light chains to form a tetrameric binding protein with six antigen binding sites.

In a preferred embodiment, a DVD-Ig binding protein not only binds the same target molecules bound by its parental monoclonal antibodies, but also possesses one or more desirable properties of one or more of its parental monoclonal antibodies. Preferably, such an additional property is an antibody parameter of one or more of the parental monoclonal antibodies. Antibody parameters that may be contributed to a DVD-Ig binding protein from one or more of its parental monoclonal antibodies include, but are not limited to, antigen specificity, antigen affinity, potency, biological function, epitope recognition, protein stability, protein solubility, production efficiency, immunogenicity, pharmacokinetics, bioavailability, tissue cross reactivity, and orthologous antigen binding.

A DVD-Ig binding protein binds at least one epitope of GFAP. Non-limiting examples of a DVD-Ig binding protein include a DVD-Ig binding protein that binds one or more epitopes of GFAP, a DVD-Ig binding protein that binds an epitope of a human GFAP and an epitope of GFAP of another species (for example, mouse), and a DVD-Ig binding protein that binds an epitope of a human GFAP and an epitope of another target molecule.

"Dynamic range" as used herein refers to range over which an assay readout is proportional to the amount of target molecule or analyte in the sample being analyzed.

"Epitope," or "epitopes," or "epitopes of interest" refer to a site(s) on any molecule that is recognized and can bind to a complementary site(s) on its specific binding partner. The molecule and specific binding partner are part of a specific binding pair. For example, an epitope can be on a polypeptide, a protein, a hapten, a carbohydrate antigen (such as, but not limited to, glycolipids, glycoproteins or lipopolysaccharides), or a polysaccharide. Its specific binding partner can be, but is not limited to, an antibody.

"Fingerstick blood sample" or "finger prick blood sample" as used interchangeably herein, refers to a capillary blood sample obtained from the fingers or digits of a subject using a microneedle, lancet, microlancet, or any other suitable device or combination thereof (e.g., a fingerstick device). In some embodiments, a fingerstick blood sample is whole blood, serum or plasma. In some aspects, the fingerstick blood sample contains predominantly capillary blood, but may also contain or comprise a small amount or percentage of interstitial fluid.

"Fragment antigen-binding fragment" or "Fab fragment" as used herein refers to a fragment of an antibody that binds to antigens and that contains one antigen-binding site, one complete light chain, and part of one heavy chain. Fab is a monovalent fragment consisting of the VL, VH, CL and CH1 domains. Fab is composed of one constant and one variable domain of each of the heavy and the light chain. The variable domain contains the paratope (the antigen-binding site), comprising a set of complementarity determining regions, at the amino terminal end of the monomer. Each arm of the Y thus binds an epitope on the antigen. Fab fragments can be generated such as has been described in the art, e.g., using the enzyme papain, which can be used to cleave an immunoglobulin monomer into two Fab fragments and an Fc fragment, or can be produced by recombinant means.

"F(ab')$_2$ fragment" as used herein refers to antibodies generated by pepsin digestion of whole IgG antibodies to remove most of the Fc region while leaving intact some of the hinge region. F(ab')$_2$ fragments have two antigen-binding F(ab) portions linked together by disulfide bonds, and therefore are divalent with a molecular weight of about 110 kDa. Divalent antibody fragments (F(ab')$_2$ fragments) are smaller than whole IgG molecules and enable a better penetration into tissue thus facilitating better antigen recognition in immunohistochemistry. The use of F(ab')$_2$ fragments also avoids unspecific binding to Fc receptor on live cells or to Protein A/G. F(ab')$_2$ fragments can both bind and precipitate antigens.

"Framework" (FR) or "Framework sequence" as used herein may mean the remaining sequences of a variable region minus the CDRs. Because the exact definition of a CDR sequence can be determined by different systems (for example, see above), the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3, and FR4) on each chain, in which CDR1 is positioned between FR1 and FR2, CDR2 between FR2 and FR3, and CDR3 between FR3 and FR4. Without specifying the particular sub-regions as FR1, FR2, FR3, or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region. Human heavy chain and light chain FR sequences are known in the art that can be used as heavy chain and light chain "acceptor" framework sequences (or simply, "acceptor" sequences) to humanize a non-human antibody using techniques known in the art. In one embodiment, human heavy chain and light chain acceptor sequences are selected from the framework sequences listed in publicly available databases such as V-base (hypertext transfer protocol://vbase.mrc-cpe.cam.ac.uk/) or in the international ImMunoGeneTics® (IMGT®) information system (hypertext transfer protocol://imgt.cines.fr/texts/IMGTrepertoire/LocusGenes/).

"Functional antigen binding site" as used herein may mean a site on a binding protein (e.g., an antibody) that is capable of binding a target antigen. The antigen binding affinity of the antigen binding site may not be as strong as the parent binding protein, e.g., parent antibody, from which the antigen binding site is derived, but the ability to bind antigen must be measurable using any one of a variety of methods known for evaluating protein, e.g., antibody, binding to an antigen. Moreover, the antigen binding affinity of each of the antigen binding sites of a multivalent protein, e.g., multivalent antibody, herein need not be quantitatively the same.

"GFAP" is used herein to describe glial fibrillary acidic protein. GFAP is a protein that is encoded by the GFAP gene in humans, and which can be produced (e.g., by recombinant means, in other species).

"GFAP status" can mean either the level or amount of GFAP at a point in time (such as with a single measure of GFAP), the level or amount of GFAP associated with monitoring (such as with a repeat test on a subject to identify an increase or decrease in GFAP amount), the level or amount of GFAP associated with treatment for traumatic brain injury (whether a primary brain injury and/or a secondary brain injury) or combinations thereof.

"Glasgow Coma Scale" or "GCS" as used herein refers to a 15-point scale (e.g., described in 1974 by Graham Teasdale and Bryan Jennett, *Lancet* 1974; 2:81-4) that provides a practical method for assessing impairment of conscious level in patients who have suffered a brain injury. The test measures the best motor response, verbal response and eye opening response with these values: I. Best Motor Response (6—obey 2-part request; 5—brings hand above clavicle to stimulus on head neck; 4—bends arm at elbow rapidly but features not predominantly abnormal; 3—bends arm at elbow, features clearly predominantly abnormal; 2—extends arm at elbow; 1-no movement in arms/legs, no interfering factor; NT—paralyzed or other limiting factor); II. Verbal Response (5—correctly gives name, place and date; 4—not orientated but communication coherently; 3—intelligible single words; 2—only moans/groans; 1—no audible response, no interfering factor; NT—factor interfering with communication); and III. Eye Opening (4—open before stimulus; 3—after spoken or shouted request; 2—after fingertip stimulus; 1—no opening at any time, no interfering factor; NT—closed by local factor). The final score is determined by adding the values of I+II+III. A subject is considered to have a mild TBI if the GCS score is 13-15. A subject is considered to have a moderate TBI if the GCS score is 9-12. A subject is considered to have a severe TBI if the GCS score is 8 or less, typically 3-8.

"Glasgow Outcome Scale" as used herein refers to a global scale for functional outcome that rates patient status into one of five categories: Dead, Vegetative State, Severe Disability, Moderate Disability or Good Recovery. "Extended Glasgow Outcome Scale" or "GOSE" as used interchangeably herein provides more detailed categorization into eight categories by subdividing the categories of severe disability, moderate disability and good recovery into a lower and upper category as shown in Table 1.

TABLE 1

| 1 | Death | D | |
|---|---|---|---|
| 2 | Vegetative state | VX | |
| 3 | Lower severe disability | SD– | Condition of unawareness with only reflex responses but with periods of spontaneous eye opening |
| 4 | Upper severe disability | SD+ | |
| 5 | Lower moderate disability | MD– | Patient who is dependent for daily support for mental or physical disability, usually a combination of both. If the patient can be left |
| 6 | Upper moderate disability | MD+ | alone for more than 8 hours at home it is upper level of MD, if not then it is low level of MD. |
| 7 | Lower good recovery | GR– | Patients have some disability such as aphasia, hemiparesis or epilepsy and/or deficits of |
| 8 | Upper good recovery | GR+ | memory or personality but are able to look after themselves. They are independent at home but dependent outside. If they are able to return to work even with special arrangement it is upper level of GR, if not then it is low level of GR. |

As used herein the term "hydrophilic", such as in reference to a "hydrophilic material" (e.g., membrane, film, etc.) refers to those materials having a water contact angle of less than about 40 degrees.

As used herein the term "hydrophobic", such as in reference to a "hydrophobic material" (e.g., membrane, film, etc.) refers to those materials having a water contact angle greater than about 80 degrees.

"Humanized antibody" is used herein to describe an antibody that comprises heavy and light chain variable region sequences from a non-human species (e.g., a mouse) but in which at least a portion of the VH and/or VL sequence has been altered to be more "human-like," i.e., more similar to human germline variable sequences. A "humanized antibody" is an antibody or a variant, derivative, analog, or fragment thereof, which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98%, or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. In an embodiment, a humanized antibody also comprises at least a portion of an immunoglobulin constant region (Fc), typically that of a human immunoglobulin. In some embodiments, a humanized antibody contains the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

A humanized antibody can be selected from any class of immunoglobulins, including IgM, IgG, IgD, IgA, and IgE, and any isotype, including without limitation IgG1, IgG2, IgG3, and IgG4. A humanized antibody may comprise sequences from more than one class or isotype, and particular constant domains may be selected to optimize desired effector functions using techniques well-known in the art.

The framework regions and CDRs of a humanized antibody need not correspond precisely to the parental sequences, e.g., the donor antibody CDR or the consensus framework may be mutagenized by substitution, insertion, and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see, e.g., Winnaker, *From Genes to Clones* (Verlagsgesellschaft, Weinheim, 1987)). A "consensus immunoglobulin sequence" may thus comprise a "consensus framework region(s)" and/or a "consensus CDR(s)". In a family of immunoglobulins, each position in the consensus sequence is occupied by the amino acid occurring most frequently at that position in the family. If two amino acids occur equally frequently, either can be included in the consensus sequence.

"Identical" or "identity," as used herein in the context of two or more polypeptide or polynucleotide sequences, can mean that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation.

"Injury to the head" or "head injury" as used interchangeably herein, refers to any trauma to the scalp, skull, or brain. Such injuries may include only a minor bump on the skull or may be a serious brain injury. Such injuries include primary injuries to the brain and/or secondary injuries to the brain. Primary brain injuries occur during the initial insult and result from displacement of the physical structures of the brain. More specifically, a primary brain injury is the physical damage to parenchyma (tissue, vessels) that occurs during the traumatic event, resulting in shearing and compression of the surrounding brain tissue. Secondary brain injuries occur subsequent to the primary injury and may involve an array of cellular processes. More specifically, a secondary brain injury refers to the changes that evolve over a period of time (from hours to days) after the primary brain injury. It includes an entire cascade of cellular, chemical, tissue, or blood vessel changes in the brain that contribute to further destruction of brain tissue.

An injury to the head can be either closed or open (penetrating). A closed head injury refers to a trauma to the scalp, skull or brain where there is no penetration of the skull by a striking object. An open head injury refers a trauma to the scalp, skull or brain where there is penetration of the skull by a striking object. An injury to the head may be caused by physical shaking of a person, by blunt impact by an external mechanical or other force that results in a closed or open head trauma (e.g., vehicle accident such as with an automobile, plane, train, etc.; blow to the head such as with a baseball bat, or from a firearm), a cerebral vascular accident (e.g., stroke), one or more falls (e.g., as in sports or other activities), explosions or blasts (collectively, "blast injuries") and by other types of blunt force trauma. Alternatively, an injury to the head may be caused by the ingestion and/or exposure to a fire, chemical, toxin or a combination of a chemical and toxin. Examples of such chemicals and/or toxins include molds, asbestos, pesticides and insecticides, organic solvents, paints, glues, gases (such as carbon monoxide, hydrogen sulfide, and cyanide), organic metals (such as methyl mercury, tetraethyl lead and organic tin) and/or one or more drugs of abuse. Alternatively, an injury to the head may be caused as a result of a subject suffering from an autoimmune disease, a metabolic disorder, a brain tumor, hypoxia, a viral infection (e.g., SARS-CoV-2), a fungal infection, a bacterial infection, meningitis, hydrocephalus, or any combinations thereof. In some cases, it is not possible to be certain whether any such event or injury has occurred or taken place. For example, there may be no history on a patient or subject, the subject may be unable to speak, the subject may be aware of what events they were exposed to, etc. Such circumstances are described herein as the subject "may have sustained an injury to the head." In certain embodiments herein, the closed head injury does not include and specifically excludes a cerebral vascular accident, such as stroke.

"Interstitial fluid" as used herein refers to the fluid that surrounds and/or fills the space between cells. Interstitial fluid can contain or comprise a mixture of water, ions, and small solutes that are forced out of the blood by the systolic pressure created when the heart pumps.

"Intracranial lesion" as used herein refers to an area of injury within the brain. An intracranial lesion can be an abnormality seen on a CT scan or brain-imaging test, such as magnetic resonance imaging (MRI). On CT or MRI scans, brain lesions can appear as dark or light spots that do not look like normal brain tissue.

"Isolated polynucleotide" as used herein may mean a polynucleotide (e.g., of genomic, cDNA, or synthetic origin, or a combination thereof) that, by virtue of its origin, the isolated polynucleotide is not associated with all or a portion of a polynucleotide with which the "isolated polynucleotide" is found in nature; is operably linked to a polynucleotide that it is not linked to in nature; or does not occur in nature as part of a larger sequence.

"Label" and "detectable label" as used herein refer to a moiety attached to an antibody or an analyte to render the reaction between the antibody and the analyte detectable, and the antibody or analyte so labeled is referred to as "detectably labeled." A label can produce a signal that is detectable by visual or instrumental means. Various labels include signal-producing substances, such as chromagens, fluorescent compounds, chemiluminescent compounds, radioactive compounds, and the like. Representative examples of labels include moieties that produce light, e.g., acridinium compounds, and moieties that produce fluorescence, e.g., fluorescein. Other labels are described herein. In this regard, the moiety, itself, may not be detectable but may become detectable upon reaction with yet another moiety. Use of the term "detectably labeled" is intended to encompass such labeling.

Any suitable detectable label as is known in the art can be used. For example, the detectable label can be a radioactive label (such as 3H, 14C, 32P, 33P, 35S, 90Y, 99Tc, 111In, 125I, 131I, 177Lu, 166Ho, and 153Sm), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immunopolymerase chain reaction label. An introduction to labels, labeling procedures and detection of labels is found in Polak and Van Noorden, *Introduction to Immunocytochemistry, 2nd* ed., Springer Verlag, N.Y. (1997), and in Haugland, *Handbook of Fluorescent Probes and Research Chemicals* (1996), which is a combined handbook and catalogue published by Molecular Probes, Inc., Eugene, Oregon. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous chemiluminescent assay (see, e.g., Adamczyk et al., Bioorg. *Med. Chem. Lett.* 16: 1324-1328 (2006); Adamczyk et al., *Bioorg. Med. Chem. Lett.* 4: 2313-2317 (2004); Adamczyk et al., *Biorg. Med. Chem. Lett.* 14: 3917-3921 (2004); and Adamczyk et al., *Org. Lett.* 5: 3779-3782 (2003)).

In one aspect, the acridinium compound is an acridinium-9-carboxamide. Methods for preparing acridinium 9-carboxamides are described in Mattingly, *J. Biolumin. Chemilumin.* 6: 107-114 (1991); Adamczyk et al., *J. Org. Chem.* 63: 5636-5639 (1998); Adamczyk et al., *Tetrahedron* 55: 10899-10914 (1999); Adamczyk et al., *Org. Lett.* 1: 779-781 (1999); Adamczyk et al., *Bioconjugate Chem.* 11: 714-724 (2000); Mattingly et al., In *Luminescence Biotechnology: Instruments and Applications*; Dyke, K. V. Ed.; CRC Press: Boca Raton, pp. 77-105 (2002); Adamczyk et al., *Org. Lett.* 5: 3779-3782 (2003); and U.S. Pat. Nos. 5,468,646, 5,543, 524 and 5,783,699 (each of which is incorporated herein by reference in its entirety for its teachings regarding same).

Another example of an acridinium compound is an acridinium-9-carboxylate aryl ester. An example of an acridinium-9-carboxylate aryl ester of formula II is 10-methyl-9-(phenoxycarbonyl)acridinium fluorosulfonate (available from Cayman Chemical, Ann Arbor, MI). Methods for preparing acridinium 9-carboxylate aryl esters are described in McCapra et al., *Photochem. Photobiol.* 4: 1111-21 (1965); Razavi et al., *Luminescence* 15: 245-249 (2000); Razavi et al., *Luminescence* 15: 239-244 (2000); and U.S. Pat. No. 5,241,070 (each of which is incorporated herein by reference in its entirety for its teachings regarding same). Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9-carboxylate aryl ester is completed rapidly, i.e., in under 1 second, while the acridinium-9-carboxamide chemiluminescent emission extends over 2 seconds. Acridinium-9-carboxylate aryl ester, however, loses its chemiluminescent properties in the presence of protein. Therefore, its use requires the absence of protein during signal generation and detection. Methods for separating or removing proteins in the sample are well-known to those skilled in the art and include, but are not limited to, ultrafiltration, extraction, precipitation, dialysis, chromatography, and/or digestion (see, e.g., Wells, *High Throughput Bioanalytical Sample Preparation. Methods and Automation Strategies*, Elsevier (2003)). The amount of protein removed or separated from the test sample can be about 40%, about 45%, about 50%, about 55%, about 60%, about 65%, about 70%, about 75%, about 80%, about 85%, about 90%, or about 95%. Further details regarding acridinium-9-carboxylate aryl ester and its use are set forth in U.S. patent application Ser. No. 11/697, 835, filed Apr. 9, 2007. Acridinium-9-carboxylate aryl esters can be dissolved in any suitable solvent, such as degassed anhydrous N,N-dimethylformamide (DMF) or aqueous sodium cholate.

"Linking sequence" or "linking peptide sequence" refers to a natural or artificial polypeptide sequence that is connected to one or more polypeptide sequences of interest (e.g., full-length, fragments, etc.). The term "connected" refers to the joining of the linking sequence to the polypeptide sequence of interest. Such polypeptide sequences are preferably joined by one or more peptide bonds. Linking sequences can have a length of from about 4 to about 50 amino acids. Preferably, the length of the linking sequence is from about 6 to about 30 amino acids. Natural linking sequences can be modified by amino acid substitutions, additions, or deletions to create artificial linking sequences. Linking sequences can be used for many purposes, including in recombinant Fabs. Exemplary linking sequences include, but are not limited to: (i) Histidine (His) tags, such as a 6×His tag, which has an amino acid sequence of HHHHHH (SEQ ID NO: 3), are useful as linking sequences to facilitate the isolation and purification of polypeptides and antibodies of interest; (ii) Enterokinase cleavage sites, like His tags, are used in the isolation and purification of proteins and antibodies of interest. Often, enterokinase cleavage sites are used together with His tags in the isolation and purification of proteins and antibodies of interest. Various enterokinase cleavage sites are known in the art. Examples of enterokinase cleavage sites include, but are not limited to, the amino acid sequence of DDDDK (SEQ ID NO: 4) and derivatives thereof (e.g., ADDDDK (SEQ ID NO: 5), etc.); (iii) Miscellaneous sequences can be used to link or connect the light and/or heavy chain variable regions of single chain variable region fragments. Examples of other linking sequences can be found in Bird et al., *Science* 242: 423-426 (1988); Huston et al., *PNAS USA* 85: 5879-5883 (1988); and McCafferty et al., *Nature* 348: 552-554 (1990). Linking sequences also can be modified for additional functions, such as attachment of drugs or attachment to solid supports. In the context of the present disclosure, the monoclonal antibody, for example, can contain a linking sequence, such as a His tag, an enterokinase cleavage site, or both.

"Magnetic resonance imaging" or "MRI" as used interchangeably herein refers to a medical imaging technique used in radiology to form pictures of the anatomy and the physiological processes of the body in both health and disease (e.g., referred to herein interchangeably as "an MRI", "an MRI procedure" or "an MRI scan"). MRI is a form of medical imaging that measures the response of the atomic nuclei of body tissues to high-frequency radio waves when placed in a strong magnetic field, and that produces images of the internal organs. MRI scanners, which is based on the science of nuclear magnetic resonance (NMR), use strong magnetic fields, radio waves, and field gradients to generate images of the inside of the body.

As used herein, the term "microchannel" refers to a channel having a cross-sectional dimension (namely, height and width) that is less than about 200 µm. In some aspects, the channel has a cross-sectional dimension of less than about 150 µm. In yet other aspects, the channel has a cross-sectional dimension of less than about 100 µm.

"Microsampling device" as used herein refers to any device known in the art that is suitable for extracting capillary blood through the skin. It is understood that while a sample obtained through the skin using a microsampling device will comprise predominantly capillary blood, the sample may also comprise a small amount or percentage of interstitial fluid. In some aspects, the microsampling device can comprise from about 0.1 mL to about 4 mL of capillary blood. In some other aspects, the device contains a plurality of microneedles, lancets or microlancets, blades or micro-blades, microscrews, or any combination thereof. In some aspects, the plurality of microneedles, lancets or microlan-cets, blades or microblades, microscrews, or any combina-tion thereof can be rotating. In yet other aspects, the plurality of microneedles, lancets or microlancets, blades or micro-blades, microscrews, or any combination thereof are non-rotating. In some aspects, the microsampling device creates a vacuum and/or uses a stored vacuum to pull the skin into the device and/or activate the plurality of microneedles, lancets or microlancets, blades or microblades, microscrews, or any combination thereof to cut the skin. Exemplary microsampling devices which can be used in the methods described herein include the TAP device available from YourBio Health, Inc. (Cambridge, MA) as well as the device described in U.S. Pat. No. 9,113,836, the contents of which are herein incorporated by reference, the Tasso+, Tasso-M20, and Tasso-ST devices available from Tasso, Inc. (Seattle, WA), the One Draw device available from Draw Bridge Health (San Diego, CA), PBS-1000 from Preci-Health (Neuchatel, Switzerland) or the Loop blood collec-tion device available from Loop Medical (Lausanne, Swit-zerland). In other aspects, an example of a microsampling device includes a fingerstick device. In some aspects, the microsampling device can include a band-aid, bandage, or other suitable material which can be applied or dispensed to the area of the skin once the sample is obtained and/or the device is removed and/or detached from the skin.

"Monoclonal antibody" as used herein refers to an anti-body obtained from a population of substantially homoge-neous antibodies, i.e., the individual antibodies comprising the population are identical except for possible naturally occurring mutations that may be present in minor amounts. Monoclonal antibodies are highly specific, being directed against a single antigen. Furthermore, in contrast to poly-clonal antibody preparations that typically include different antibodies directed against different determinants (epitopes), each monoclonal antibody is directed against a single deter-minant on the antigen. The monoclonal antibodies herein specifically include "chimeric" antibodies in which a portion of the heavy and/or light chain is identical with or homolo-gous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biologi-cal.

"Multivalent binding protein" is used herein to refer to a binding protein comprising two or more antigen binding sites (also referred to herein as "antigen binding domains"). A multivalent binding protein is preferably engineered to have three or more antigen binding sites and is generally not a naturally occurring antibody. The term "multispecific binding protein" refers to a binding protein that can bind two or more related or unrelated targets, including a binding protein capable of binding two or more different epitopes of the same target molecule.

"Negative predictive value" or "NPV" as used inter-changeably herein refers to the probability that a subject has a negative outcome given that they have a negative test result.

"Operatively coupled" or "operatively linked" as used herein means that a number of elements or assemblies, each of which is movable between a first position and a second position, or a first configuration and a second configuration, are coupled so that as the first element moves from one position/configuration to the other, the second element moves between positions/configurations as well. It is noted that a first element may be "operatively coupled" to another without the opposite being true. Where movement is capable between a first element and another element, and vice versa, the elements are said to be "reciprocally operatively coupled".

"Normalize" or "normalizing" as used herein refers adjusting the amount of an analyte (e.g., GFAP) determined in a capillary blood sample obtained from a subject based on the amount of the same analyte in venous blood. In some aspects, for example, normalizing can involve multiplying a factor (e.g., correlation or conversion factor) by the amount of the analyte in the capillary blood sample.

"Point-of-care device" refers to a device used to provide medical diagnostic testing at or near the point-of-care (namely, typically, outside of a laboratory), at the time and place of patient care (such as in a hospital, physician's office, urgent or other medical care facility, a patient's home, a nursing home and/or a long term care and/or hospice facil-ity). Examples of point-of-care devices include those pro-duced by Abbott Laboratories (Abbott Park, IL) (e.g., i-STAT and i-STAT Alinity, Universal Biosensors (Rowville, Australia) (see US 2006/0134713), Axis-Shield PoC AS (Oslo, Norway) and Clinical Lab Products (Los Angeles, USA).

"Positive predictive value" or "PPV" as used interchange-ably herein refers to the probability that a subject has a positive outcome given that they have a positive test result.

"Quality control reagents" in the context of immunoas-says and kits described herein, include, but are not limited to, calibrators, controls, and sensitivity panels. A "calibra-tor" or "standard" typically is used (e.g., one or more, such as a plurality) in order to establish calibration (standard) curves for interpolation of the amount of an analyte, such as an antibody or an analyte. Alternatively, a single calibrator, which is near a reference level or control level (e.g., "low", "medium", or "high" levels), can be used. Multiple calibra-tors (i.e., more than one calibrator or a varying amount of calibrator(s)) can be used in conjunction to comprise a "sensitivity panel."

As used herein, a "reaction vessel" refers to a holder or receiver, such as a container, receptacle, tube, and/or cartridge, in or upon which an assay is performed. In some aspects, a reaction vessel may have one or more apertures.

A "receiver operating characteristic" curve or "ROC" curve refers to a graphical plot that illustrates the performance of a binary classifier system as its discrimination threshold is varied. For example, a ROC curve can be a plot of the true positive rate against the false positive rate for the different possible cutoff points of a diagnostic test. It is created by plotting the fraction of true positives out of the positives (TPR=true positive rate) vs. the fraction of false positives out of the negatives (FPR=false positive rate), at various threshold settings. TPR is also known as sensitivity, and FPR is one minus the specificity or true negative rate. The ROC curve demonstrates the tradeoff between sensitivity and specificity (any increase in sensitivity will be accompanied by a decrease in specificity); the closer the curve follows the left-hand border and then the top border of the ROC space, the more accurate the test; the closer the curve comes to the 45-degree diagonal of the ROC space, the less accurate the test; the slope of the tangent line at a cutoff point gives the likelihood ratio (LR) for that value of the test; and the area under the curve is a measure of test accuracy.

"Recombinant antibody" and "recombinant antibodies" refer to antibodies prepared by one or more steps, including cloning nucleic acid sequences encoding all or a part of one or more monoclonal antibodies into an appropriate expression vector by recombinant techniques and subsequently expressing the antibody in an appropriate host cell. The terms include, but are not limited to, recombinantly produced monoclonal antibodies, chimeric antibodies, humanized antibodies (fully or partially humanized), multi-specific or multi-valent structures formed from antibody fragments, bifunctional antibodies, heteroconjugate Abs, DVD-Ig® s, and other antibodies as described in (i) herein. (Dual-variable domain immunoglobulins and methods for making them are described in Wu, C., et al., *Nature Biotechnology*, 25:1290-1297 (2007)). The term "bifunctional antibody," as used herein, refers to an antibody that comprises a first arm having a specificity for one antigenic site and a second arm having a specificity for a different antigenic site, i.e., the bifunctional antibodies have a dual specificity.

"Reference level" as used herein refers to an assay cutoff value that is used to assess diagnostic, prognostic, or therapeutic efficacy and that has been linked or is associated herein with various clinical parameters (e.g., presence of disease, stage of disease, severity of disease, progression, non-progression, or improvement of disease, etc.). An "absolute amount" as used herein refers to the absolute value of a change or difference between at least two assay results taken or sampled at different time points and, which similar to a reference level, has been linked or is associated herein with various clinical parameters (e.g., presence of disease, stage of disease, severity of disease, progression, non-progression, or improvement of disease, etc.). "Absolute value" as used herein refers to the magnitude of a real number (such as, for example, the difference between two compared levels (such as levels taken at a first time point and levels taken at a second time point)) without regard to its sign, i.e., regardless of whether it is positive or negative. The UCH-L1 and/or GFAP reference levels referred to herein are from venous blood.

This disclosure provides exemplary reference levels and absolute amounts (e.g., calculated by comparing reference levels at different time points). However, it is well-known that reference levels and absolute amounts may vary depending on the nature of the immunoassay (e.g., antibodies employed, reaction conditions, sample purity, etc.) and that assays can be compared and standardized. It further is well within the ordinary skill of one in the art to adapt the disclosure herein for other immunoassays to obtain immunoassay-specific reference levels and absolute amounts for those other immunoassays based on the description provided by this disclosure. Whereas the precise value of the reference level and absolute amount may vary between assays, the findings as described herein should be generally applicable and capable of being extrapolated to other assays.

"Removably coupled" or "removably linked" as used herein means that one component is coupled with another component in an essentially temporary manner. That is, the two components are coupled in such a way that the joining or separation of the components is easy and does not damage the components. Accordingly, "removably coupled" components may be readily uncoupled and recoupled without damage to the components.

"Result" as used herein refers to an item of information obtained by performing an assay. In one aspect, a result is an amount of a biomarker (e.g., GFAP or GFAP and UCH-L1) in a test sample (e.g, capillary blood sample). In another aspect, a result is identifying the presence of biomarker (e.g., GFAP or GFAP and UCH-L1) in a sample. A result can be visually displayed (e.g., as a readout).

"Risk assessment," "risk classification," "risk identification," or "risk stratification" of subjects (e.g., patients) as used herein refers to the evaluation of factors including biomarkers, to predict the risk of occurrence of future events including disease onset or disease progression, so that treatment decisions regarding the subject may be made on a more informed basis.

"Plasma separation device" as used herein, refers to an apparatus or device that can be used to separate components of whole blood (e.g., red and white blood cells) from serum, plasma or serum and plasma using a separation system, such as, for example, at least one membrane, filter, synthetic paper (e.g., micropillar scaffolds) or any combination thereof. For example, the membrane and/or filter that can be used in the plasma separation device may comprise at least one of polycarbonate, polysulfone, polyester, polyethylene, polyurethane and polypropylene. In some aspects, the membrane and/or filter is pre-treated (e.g., with one or more polycations, zwitterions, one or more noncovalent surface treatments (e.g., PEGMA, HEMA, BSA, $O_2$ plasma etc.)). In other aspects, the membrane and/or filter is not pre-treated. In still further aspects, the filter that can be used is a gravity-assisted separation system. Examples of plasma separation devices that can be used in the methods described herein include those described in U.S. Patent Publication No. 2020/0124508, the contents of which are herein incorporated by reference. In some aspects, a plasma separation device does not include a lateral flow device.

"Sensitivity" of an assay as used herein refers to the proportion of subjects for whom the outcome is positive that are correctly identified as positive (e.g., correctly identifying those subjects with a disease or medical condition for which they are being tested). For example, this might include correctly identifying subjects as having a TBI as distinct from those who do not have a TBI, correctly identifying subjects having a moderate, severe, or moderate to severe TBI as distinct from those having a mild TBI, correctly identifying subjects as having a mild TBI as distinct from those having a moderate, severe, or moderate to severe TBI, correctly identifying subjects as having a moderate, severe, or moderate to severe TBI as distinct from those having no TBI or correctly identifying subjects as having a mild TBI as distinct from those having no TBI etc.

"Specificity" of an assay as used herein refers to the proportion of subjects for whom the outcome is negative that are correctly identified as negative (e.g., correctly identifying those subjects who do not have a disease or medical condition for which they are being tested). For example, this might include correctly identifying subjects not having an TBI as distinct from those who do have a TBI, correctly identifying subjects not having a moderate, severe, or moderate to severe TBI as distinct from those having a mild TBI, correctly identifying subjects as not having a mild TBI as distinct from those having a moderate, severe, or moderate to severe TBI, etc.).

"Series of calibrating compositions" refers to a plurality of compositions comprising a known amount of GFAP, wherein each of the compositions differs from the other compositions in the series by the amount of GFAP.

"Solid phase" or "solid support" as used interchangeably herein, refers to any material that can be used to attach and/or attract and immobilize (1) one or more capture agents or capture specific binding partners, or (2) one or more detection agents or detection specific binding partners. The solid phase can be chosen for its intrinsic ability to attract and immobilize a capture agent. Alternatively, the solid phase can have affixed thereto a linking agent that has the ability to attract and immobilize the (1) capture agent or capture specific binding partner, or (2) detection agent or detection specific binding partner. For example, the linking agent can include a charged substance that is oppositely charged with respect to the capture agent (e.g., capture specific binding partner) or detection agent (e.g., detection specific binding partner) itself or to a charged substance conjugated to the (1) capture agent or capture specific binding partner or (2) detection agent or detection specific binding partner. In general, the linking agent can be any binding partner (preferably specific) that is immobilized on (attached to) the solid phase and that has the ability to immobilize the (1) capture agent or capture specific binding partner, or (2) detection agent or detection specific binding partner through a binding reaction. The linking agent enables the indirect binding of the capture agent to a solid phase material before the performance of the assay or during the performance of the assay. For examples, the solid phase can be plastic, derivatized plastic, magnetic, or non-magnetic metal, glass or silicon, including, for example, a test tube, microtiter well, sheet, bead, microparticle, chip, and other configurations known to those of ordinary skill in the art. In some aspects, the solid support can be a magnetically susceptible bead or particle.

"Specific binding" or "specifically binding" as used herein may refer to the interaction of an antibody, a protein, or a peptide with a second chemical species, wherein the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

"Specific binding partner" is a member of a specific binding pair. A specific binding pair comprises two different molecules, which specifically bind to each other through chemical or physical means. Therefore, in addition to antigen and antibody specific binding pairs of common immunoassays, other specific binding pairs can include biotin and avidin (or streptavidin), carbohydrates and lectins, complementary nucleotide sequences, effector and receptor molecules, cofactors and enzymes, enzymes and enzyme inhibitors, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes and fragments thereof, whether isolated or recombinantly produced.

"Statistically significant" as used herein refers to the likelihood that a relationship between two or more variables is caused by something other than random chance. Statistical hypothesis testing is used to determine whether the result of a data set is statistically significant. In statistical hypothesis testing, a statistically significant result is attained whenever the observed p-value of a test statistic is less than the significance level defined of the study. The p-value is the probability of obtaining results at least as extreme as those observed, given that the null hypothesis is true. Examples of statistical hypothesis analysis include Wilcoxon signed-rank test, t-test, Chi-Square or Fisher's exact test. "Significant" as used herein refers to a change that has not been determined to be statistically significant (e.g., it may not have been subject to statistical hypothesis testing).

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgus or rhesus monkey, chimpanzee, etc.) and a human). In some embodiments, the subject may be a human or a non-human. In some embodiments, the subject is a human. The subject or patient may be undergoing other forms of treatment.

"Treat," "treating" or "treatment" are each used interchangeably herein to describe reversing, alleviating, or inhibiting the progress of a disease and/or injury, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a pharmaceutical composition to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

As used herein, a "transfer tube" refers to a container or receptacle used to transfer a fluid (e.g., a capillary blood sample) from one location to a second location (e.g., to a reaction vessel or from a plasma separation device).

"Traumatic Brain Injury" or "TBI" as used interchangeably herein refers to a complex injury with a broad spectrum of symptoms and disabilities. TBI is most often an acute event similar to other injuries. TBI can be classified as "mild," "moderate," or "severe." The causes of TBI are diverse and include, for example, physical shaking by a person, a car accident, injuries from firearms, cerebral vascular accidents (e.g., strokes), falls, explosions or blasts and other types of blunt force trauma. Other causes of TBI include the ingestion and/or exposure to one or more fires, chemicals or toxins (such as molds, asbestos, pesticides and insecticides, organic solvents, paints, glues, gases (such as carbon monoxide, hydrogen sulfide, and cyanide), organic metals (such as methyl mercury, tetraethyl lead and organic tin), one or more drugs of abuse or combinations thereof). Alternatively, TBI can occur in subjects suffering from an autoimmune disease, a metabolic disorder, a brain tumor, hypoxia, a viral infection (e.g., SARS-CoV-2, meningitis, etc.), fungal infection (e.g., meningitis), bacterial infection (e.g., meningitis), or any combinations thereof. Young adults and the elderly are the age groups at highest risk for TBI. In certain embodiments herein, traumatic brain injury or TBI does not include and specifically excludes cerebral vascular accidents such as strokes.

"Mild TBI" as used herein refers to a head injury where a subject may or may not experience a loss of consciousness. For subjects that experience a loss of consciousness, it is typically brief, usually lasting only a few seconds or minutes. Mild TBI is also referred to as a concussion, minor head trauma, minor TBI, minor brain injury, and minor head injury. While MRI and CT scans are often normal, the individual with mild TBI may have cognitive problems such as headache, difficulty thinking, memory problems, attention deficits, mood swings and frustration.

Mild TBI is the most prevalent TBI and is often missed at time of initial injury. Typically, a subject has a Glasgow Coma scale number of between 13-15 (such as 13-15 or 14-15). Fifteen percent (15%) of people with mild TBI have symptoms that last 3 months or more. Common symptoms of mild TBI include fatigue, headaches, visual disturbances, memory loss, poor attention/concentration, sleep disturbances, dizziness/loss of balance, irritability-emotional disturbances, feelings of depression, and seizures. Other symptoms associated with mild TBI include nausea, loss of smell, sensitivity to light and sounds, mood changes, getting lost or confused, and/or slowness in thinking.

"Moderate TBI" as used herein refers to a brain injury where loss of consciousness and/or confusion and disorientation is between 1 and 24 hours and the subject has a Glasgow Coma scale number of between 9-13 (such as 9-12 or 9-13). The individual with moderate TBI may have abnormal brain imaging results. "Severe TBI" as used herein refers to a brain injury where loss of consciousness is more than 24 hours and memory loss after the injury or penetrating skull injury longer than 24 hours and the subject has a Glasgow Coma scale number between 3-8. The deficits range from impairment of higher level cognitive functions to comatose states. Survivors may have limited function of arms or legs, abnormal speech or language, loss of thinking ability or emotional problems. Individuals with severe injuries can be left in long-term unresponsive states. For many people with severe TBI, long-term rehabilitation is often necessary to maximize function and independence.

"Moderate to severe" TBI as used herein refers to a spectrum of brain injury that includes a change from moderate to severe TBI over time and thus encompasses (e.g., temporally) moderate TBI alone, severe TBI alone, and moderate to severe TBI combined. For example, in some clinical situations, a subject may initially be diagnosed as having a moderate TBI but who, over the course of time (minutes, hours or days), progresses to having a severe TBI (such, as for example, in situations when there is a brain bleed). Alternatively, in some clinical situations, a subject may initially be diagnosed as having a severe TBI but who, over the course of time (minutes, hours or days), progresses to having a moderate TBI. Such subjects would be examples of patients that could be classified as "moderate to severe". Common symptoms of moderate to severe TBI include cognitive deficits including difficulties with attention, concentration, distractibility, memory, speed of processing, confusion, perseveration, impulsiveness, language processing, and/or "executive functions", not understanding the spoken word (receptive aphasia), difficulty speaking and being understood (expressive aphasia), slurred speech, speaking very fast or very slow, problems reading, problems writing, difficulties with interpretation of touch, temperature, movement, limb position and fine discrimination, the integration or patterning of sensory impressions into psychologically meaningful data, partial or total loss of vision, weakness of eye muscles and double vision (diplopia), blurred vision, problems judging distance, involuntary eye movements (nystagmus), intolerance of light (photophobia), hearing issues, such as decrease or loss of hearing, ringing in the ears (tinnitus), increased sensitivity to sounds, loss or diminished sense of smell (anosmia), loss or diminished sense of taste, the convulsions associated with epilepsy that can be several types and can involve disruption in consciousness, sensory perception, or motor movements, problems with control of bowel and bladder, sleep disorders, loss of stamina, appetite changes, problems with regulation of body temperature, menstrual difficulties, dependent behaviors, issues with emotional ability or stability, lack of motivation, irritability, aggression, depression, disinhibition, or denial/lack of awareness. Subjects having a moderate to severe TBI can have a Glasgow Coma scale score from 3-12 (which includes the range of 9-12 for a moderate TBI, and 3-8 for a severe TBI).

"Variant" is used herein to describe a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree, and distribution of charged regions) is recognized in the art as typically involving a minor change. These minor changes can be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also can be used to refer to an antigenically reactive fragment of an anti-GFAP antibody that differs from the corresponding fragment of anti-GFAP antibody in amino acid sequence but is still antigenically reactive and can compete with the corresponding fragment of anti-GFAP antibody for binding with GFAP. "Variant" also can be used to describe a polypeptide or a fragment thereof that has been differentially processed, such as by proteolysis, phosphorylation, or other post-translational modification, yet retains its antigen reactivity.

"Vector" is used herein to describe a nucleic acid molecule that can transport another nucleic acid to which it has been linked. One type of vector is a "plasmid", which refers to a circular double-stranded DNA loop into which additional DNA segments may be ligated. Another type of vector is a viral vector, wherein additional DNA segments may be ligated into the viral genome. Certain vectors can replicate autonomously in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. "Plasmid" and "vector" may be used interchangeably as the plasmid is the most commonly used form of vector. However, other forms of expression vectors, such as viral vectors (e.g., replication defective retroviruses, adenoviruses and adeno-associated viruses), which serve equivalent functions, can be used. In this regard, RNA versions of vectors (including RNA viral vectors) may also find use in the context of the present disclosure.

"Venous blood" as used herein refers to a blood sample that is obtained from the veins from a subject using a syringe, needle, or combination thereof, or any appropriate device. In some embodiments, a venous blood sample is obtained by a trained health clinician such as a physician, phlebotomist, nurse, laboratory technician, or combination thereof. In some embodiments, a venous blood sample is whole blood, serum or plasma.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. Systems and Assays for Measuring the Amount of GFAP in a Biological Sample Obtained from a Subject In one embodiment, the present disclosure relates to systems and assays (e.g., methods) for measuring the amount of glial fibrillary acid protein (GFAP) in a biological sample. The systems and assays of the present disclosure utilize a point-of-care device containing at least one cartridge which comprises at least one magnetic immunosensor or immunosensing device. The magnetic immunosensor or immunosensing device is used to determine the amount of GFAP in the sample. Specifically, as will be described in more detail herein, the magnetic immunosensor or magnetic immunosensing device is used to capture and retain complexes containing GFAP that have been immobilized on magnetically susceptible beads using one or more specific binding partners (e.g., one or more antibodies).

The biological sample used in the systems and assays described herein can be a blood sample, such as a venous blood sample, a capillary blood sample, a fingerstick blood sample, or a combination thereof. In some aspects, the system and assays of the present disclosure relate to measuring the amount of GFAP in a blood sample, such as a venous blood sample, a capillary blood sample, a fingerstick blood sample, or a combination thereof.

In some aspects, when the biological sample is a blood sample (e.g., a venous blood sample, a capillary blood sample, a fingerstick blood sample, or a combination thereof), the blood sample can be subjected to further or additional processing prior to determining the amount of GFAP. In some aspects, the sample is processed using centrifugation. In yet other aspects, the sample is processed using a plasma separation device which may comprise at least one filter, membrane and/or synthetic paper. For example, in some aspects, the plasma separation device that can be used is the apparatus described in Section 3. The plasma separation device can separate blood into serum and/or plasma.

In other aspects, the plasma separation device can be in fluid communication with or operably linked, coupled and/or removably coupled to a microsampling device as part of a microsampling system as described in further detail in Section 4. In other aspects, the plasma separation device can be integrated into the microsampling device as described in further detail in Section 4.

In still yet other aspects, the plasma separation device can be in fluid communication with or operably linked, coupled and/or removably coupled to an aperture of a reaction vessel as described in further detail in Section 4. For example, in some aspects, the reaction vessel is a cartridge such as those used in a point-of-care device.

In still other aspects, the plasma separation device can be in fluid communication with or operably linked, coupled and/or removably coupled to a transfer tube as described in further detail in Section 4. In these aspects, the transfer can be in fluid communication with or operably linked, coupled and/or removably coupled to a reaction vessel as described in further detail in Section 4. In still further aspects, the plasma separation device can be integrated into the transfer tube. In yet other aspects, the transfer tube includes a cap or a stopper.

In some aspects, the systems and assays include obtaining a sample within about 24 hours of an actual or suspected injury to the subject and contacting the sample with an antibody for a biomarker of TBI, such as GFAP, to allow formation of a complex of the antibody and the biomarker. More specifically, the sample can be contacted with an anti-GFAP antibody. The assays also include detecting the resulting antibody-biomarker complex.

The systems and assays described herein can aid in determining the extent of traumatic brain injury in a subject (e.g., human subject) who has sustained, may have sustained, or is suspected of sustaining an injury to the head has more likely than not, sustained an acquired brain injury (ABI), such as a traumatic brain injury (TBI). As used herein, "determining whether the subject (e.g., a human subject) has an acquired brain injury (ABI)", refers to the fact that the aforementioned method can be used, e.g., with other information (e.g., clinical assessment data), to determine that the subject is more likely than not to have an ABI. The assays described herein can be performed on a sample obtained from the subject (e.g., a human subject) within about 24 hours after an actual or suspected injury to the head to measure or detect a level of a biomarker of ABI, such as GFAP, in the sample and determining whether the subject (e.g., a human subject) has an ABI. In some aspects, the subject is determined as having an ABI when the amount of the biomarker in the sample is higher than a reference level of a biomarker (e.g., GFAP).

The systems and assays described herein can aid in determining the extent of traumatic brain injury in a subject (e.g., human subject) with an actual or suspected injury to the head, e.g., determining whether the subject (e.g., a human subject) has a mild traumatic brain injury, moderate traumatic brain injury, severe traumatic brain injury, or a moderate to severe traumatic brain injury. As used herein, "determining whether the subject (e.g., a human subject) has a mild traumatic brain injury, a moderate traumatic brain injury, a severe traumatic brain injury, or a moderate to severe brain injury" refers to the fact that the aforementioned method can be used, e.g., with other information (e.g., clinical assessment data), to determine that the subject is more likely than not to have a mild traumatic brain injury, moderate traumatic brain injury, severe traumatic brain injury, or moderate to severe traumatic brain injury. The assays described herein can be performed on a sample obtained from the subject (e.g., a human subject) within about 24 hours after an actual or suspected injury to the head to measure or detect a level of a biomarker of traumatic brain injury, such as GFAP, in the sample and determining whether the subject (e.g., a human subject) has sustained a mild, moderate, severe, or a moderate to severe traumatic brain injury (TBI). In some aspects, the subject is determined as having a mild, moderate, severe, or moderate or severe TBI when the amount of the biomarker in the sample is higher than a reference level of a biomarker (e.g., GFAP).

A. Assays

In another embodiment, the present disclosure relates to an assay (e.g., method) for measuring GFAP in a biological sample obtained from a subject. In some aspects, the biological sample is a blood sample, such as a venous blood sample, a capillary blood sample, a fingerstick blood sample, or a combination thereof. Generally, the assay involves performing an assay for GFAP. The assay involves contacting the biological sample with a cartridge with at least one magnetic immunosensor and at least one first specific binding partner comprising at least one anti-GFAP antibody where the specific binding partner is immobilized on at least one magnetically susceptible bead that is printed on the cartridge as will be described herein. The GFAP assays described herein can be used alone or in combination with other assays that do not employ a cartridge comprising at least one magnetic immunosensor. Such assays, include, for example, assays for ubiquitin carboxy-terminal hydrolase L1 (UCH-L1).

Once the one or more complexes are formed, the beads containing the immobilized one or more complexes are magnetically captured and retained using the at least one magnetic immunosensor or magnetic immunosensing device in the cartridge that is contained in a point-of-care device. In some aspects, the any unbound sample that is not magnetically captured and retained on the magnetic immunosensor can be removed by washing the immunosensor.

Once the one or more complexes are captured and retained on the at least one magnetic immunosensor, the signal from the one or more complexes is assessed. Specifically, the amount of signal from the detectable label indicates the amount of GFAP in the sample.

In one aspect, the assay performed is an assay for measuring the amount of GFAP in a biological sample, such as a blood sample (e.g., a venous blood sample, a capillary blood sample, a fingerstick blood sample or a combination thereof). In this aspect, the assay comprises contacting the sample with a cartridge (which is used in a point-of-care device) comprising at least one magnetic immunosensor and: (i) at least one first specific binding partner comprising at least one anti-GFAP antibody which specifically binds to GFAP in the sample, where the at least one first specific binding partner is immobilized on at least one magnetically susceptible bead that is printed on the cartridge; and (ii) at least one second specific binding partner comprising a detectable label that is printed on the cartridge, to produce one or more complexes comprising the first specific binding partner-GFAP-second specific binding partner. After the complexes are formed, the magnetically susceptible beads are captured and retained on the at least one magnetic immunosensor in the cartridge in the point-of-care device. Optionally, any unbound sample can be washed from the magnetic immunosensor using routine techniques known in the art. For the complexes retained on the at least one magnetic immunosensor, the signal from the complexes are assessed. Specifically, the amount of detectable signal from the detectable label of the complexes indicates the amount of GFAP in the sample. It has been found that assays for measuring GFAP as described herein exhibit at least a 5-fold increase in sensitivity when compared to assays for GFAP that do not immobilize the first specific binding partner on a magnetically susceptible bead and magnetically capture and retain the bead containing complexes on at least one magnetic immunosensor in a cartridge contained in a point-of-care device. In some aspects, it has been found that assays for measuring GFAP as described herein exhibit at least a 6-fold, at least a 7-fold, at least an 8-fold, at least a 9-fold, at least a 10-fold, at least a 11-fold, at least a 12-fold, at least a 13-fold, at least a 14-fold, or at least a 15-fold increase in sensitivity when compared to an assay that does not immobilize the first specific binding partner on a magnetically susceptible bead and magnetically capture and retain the bead containing the complexes on at least one magnetic immunosensor in a cartridge contained in a point-of-care device.

In some aspects, the sample is taken from the subject (e.g., human subject) within about 24 hours of injury of an actual or suspected injury to the head. For example, the sample can be taken from the subject (e.g., a human subject) within about 0 minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 20 minutes, about 30 minutes, about 60 minutes, about 90 minutes, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours, after an actual or suspected injury to the head.

Examples of assays that can be used to determine the amount of GFAP include an immunoassay, such as an enzyme immunoassay (EIA), an enzyme linked immunosorbent assay (ELISA), a fluorescent immunoassay, a chemiluminescence immunoassay (CLIA), a radioimmunoassay (RIA), a microparticle enzyme immunoassay (MEIA), a turbidimetric immunoassay, etc. In yet other aspects, the assay may be a clinical chemistry assay such as, for example, a photometry, a spectrophotometry, an absorbance, a fluorescence, a turbidimetry, a nephelometry, a potentiometry and/or an electrophoresis assay. In yet further aspects, the assay may be a combination of an immunoassay and a clinical chemistry assay. In still other aspects, the assay may be a single molecule detection assay.

In some aspects, the at least one assay for GFAP is performed in about 4 to about 20 minutes. In some aspects, the at least one assay for GFAP is each performed in about 4 minutes. In some aspects, the at least one assay for GFAP is performed in about 5 minutes. In some aspects, the at least one assay for GFAP is performed in about 6 minutes. In some aspects, the at least one assay for GFAP is performed in about 7 minutes. In some aspects, the at least one assay for GFAP is performed in about 8 minutes. In some aspects, the at least one assay for GFAP is performed in about 9 minutes. In some aspects, the at least one assay for GFAP i performed in about 10 minutes. In some aspects, the at least one assay for GFAP is performed in about 11 minutes. In some aspects, the at least one assay for GFAP is performed in about 12 minutes. In some aspects, the at least one assay for GFAP is performed in about 13 minutes. In some aspects, the at least one assay for GFAP is performed in about 14 minutes. In some aspects, the at least one assay for GFAP is performed in about 15 minutes. In some aspects, the at least one assay for GFAP is performed in about 16 minutes. In some aspects, the at least one assay for GFAP is performed in about 17 minutes. In some aspects, the at least one assay for GFAP is performed in about 18 minutes. In some aspects, the at least one assay for GFAP is performed in about 19 minutes. In some aspects, the at least one assay for GFAP is performed in about 20 minutes.

In some aspects, the subject has received a Glasgow Coma Scale score before or after the assay is performed. In some aspects, the subject (e.g., a human subject) is suspected as having moderate, severe, or moderate to severe traumatic brain injury based on the Glasgow Coma Scale score. In some aspects, the reference level of the biomarker, such as GFAP, is correlated with subjects having moderate, severe, or moderate to severe traumatic brain injury. In some aspects, the reference level of the biomarker, such as GFAP, is correlated with a Glasgow Coma Scale score of 9-13 (a moderate TBI). In some aspects, the reference level of the biomarker, such as GFAP, is correlated with a Glasgow Coma Scale score of 3-8 (a severe TBI). In some aspects, the reference level of the biomarker, such as GFAP, is correlated with a Glasgow Coma Scale score of 3-12 (a moderate, severe, or moderate to severe TBI). In some aspects, the subject is suspected as having mild traumatic brain injury based on the Glasgow Coma Scale score. In some aspects, the reference level of the biomarker, such as GFAP, is correlated with subjects having mild traumatic brain injury.

In some aspects, the reference level of the biomarker, such as GFAP, is correlated with a Glasgow Coma Scale score of 13-15 (mild TBI).

Generally, a reference level of the biomarker, such as GFAP, can also be employed as a benchmark against which to assess results obtained upon assaying a test sample for the biomarker, such as GFAP. Generally, in making such a comparison, the reference level of the biomarker, such as GFAP, is obtained by running or conducting a particular assay a sufficient number of times and under appropriate conditions such that a linkage or association of analyte presence, amount or concentration with a particular stage or endpoint of TBI or with particular indicia can be made. Typically, the reference level of the biomarker, such as GFAP, is obtained with assays of reference subjects (or populations of subjects). The biomarker, such as GFAP measured can include fragments thereof, degradation products thereof, and/or enzymatic cleavage products thereof.

In certain aspects, the reference level may be correlated with control subjects (e.g., human subjects) that have not sustained a head injury.

In some aspects, after the amount of GFAP in the capillary blood sample is determined using the methods described herein, a result is obtained. This result can be further processed. Specifically, this further processing involves selecting a conversion factor for comparing the amount of GFAP in the sample with the amount of GFAP in venous blood. Specifically, the conversion factor selected can be a static correlation ratio, a dynamic ratio, or a combination of a static correlation ratio and a dynamic ratio. A static correlation ratio is a ratio that exists between venous blood and a capillary blood sample for GFAP such that there is a simple ratio (i.e., a "static" correlate). A static correlation ratio assumes a constant ratio, that could be, for example, 1.0× or 1.2× or 1.5× or even 0.8×—to be used to convert the reading relating to the capillary blood to what it would have been had GFAP had been measured from a venous blood draw.

A dynamic ratio is ratio that exists between venous blood and a capillary blood sample for GFAP which involves more than a simple ratio (i.e., involves a non-linear or variant relationship) but is instead, dependent on one or more factors, such as sampling times, diffusion rate, etc. For example, for markers such as those for acquired brain injury, such as, a traumatic brain injury (TBI), such as GFAP, one might expect that the ratio GFAP sampled by venous versus capillary blood draw might be time dependent (i.e., or "dynamic"), and, as such, not being at equilibrium would mean that the factor changes based on the time sampled post event. This would mean that the correlation could have a time delay factor and so, for example, a longitudinal sampling design would be necessary to develop e.g., a "correlative table" that includes, for instance, two factors, magnitude (of the ratio) and timing—relative to "event" and what the amount would have been in venous versus capillary blood.

In some aspects, the conversion factor (e.g., static correlation ratio, dynamic correlation ratio, or a combination of a static correlation ratio and a dynamic correlation ratio) can be selected based on: (a) the amount of GFAP in the sample; (b) the disease, disorder, condition, stage or state associated with GFAP; (c) whether the amount of GFAP is determined using an analog assay, a digital assay, or a combination of an analog assay and a digital assay; or (d) any combination of (a) through (c).

For example, in some aspects, the conversion factor selected for GFAP can be a dynamic correlation ratio.

Alternatively, in still yet further aspects, when the disease, disorder, condition, stage or state associated with GFAP is an ABI or a TBI, the conversion factor selected is a dynamic correlation ratio.

In still further aspects, the conversion factor selected is a static correlation ratio, dynamic correlation ratio, both a static correlation ratio and a dynamic correlation ratio and is about 0.01, about 0.05, about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.5, about 3.0, about 3.5, about 4.0, about 4.5, about 5.0, about 6.0, about 7.0, about 8.0, about 9.0, about 10.0, about 11.0, about 12.0, about 13.0, about 14.0, about 15.0, about 16.0, about 17.0, about 18.0, about 19.0, or about 20.0.

Alternatively, in some aspects, the conversion factor for GFAP can be from about 1.2:1.0 (venous whole blood or plasma to capillary whole blood or plasma) to about 1.0:0.5 (venous whole blood or plasma to capillary whole blood or plasma). Alternatively, in some aspects, the conversion factor for GFAP is from about 1.0:0.85 (venous whole blood or plasma to capillary whole blood or plasma). In other aspects, the conversion factor is about 1.0:0.8 (venous whole blood or plasma to capillary whole blood or plasma).

Once the conversion factor (e.g., static correlation ratio, dynamic correlation ratio, both a static correlation ratio and a dynamic correlation ratio) is selected, the processing further involves normalizing the amount of GFAP in the capillary blood sample with the amount of the GFAP from venous blood by applying the conversion factor to the amount of GFAP in the sample. For example, the amount of GFAP in the capillary blood sample can be multiplied by the conversion factor to provide the normalized amount of GFAP in the sample.

In some aspects, the processing of the amount of GFAP (e.g., the result) can be by a processing system which comprises a computer processor and a non-transitory computer memory comprising one or more computer programs, in conjunction with said computer process which are configured to select a conversion factor for comparing the amount of GFAP in the sample with the amount of GFAP in venous blood and normalize the amount of GFAP in the sample with the amount of GFAP from venous blood by applying the selected conversion factor to the amount of GFAP in the sample.

Once the normalized amount of GFAP in the capillary blood sample is obtained, this normalized result can be communicated (e.g., reported) for further analysis, interpretation, interpretation, processing and/or display. The result can be communicated (e.g., reported) by a computer, in a document and/or spreadsheet, on a mobile device (e.g., a smart phone), on a website, in an e-mail, or any combination thereof.

In some aspects, the result is communicated by being displayed, such as on an instrument. In further aspects, the result is displayed as indicating that the amount of GFAP in a subject is elevated, are not elevated, or that the assay for GFAP should be repeated.

As will be discussed in further detail in Section 2(B), the systems and assays of the present disclosure utilize point-of-care devices. Suitable point-of-care devices for use in the systems and assays described herein include, for example, i-STAT and i-STAT Alinity devices marketed by Abbott Laboratories. Such point-of-care device can contain a user interface that can display the determination.

In some aspects, the result (which can be, in some aspects, a normalized result) of GFAP is communicated in about 4 minutes to about 40 minutes from the time the sample is collected (such as, for example, from the time of injury or suspected injury). In other aspects, the result is communicated in about 4 minutes to about 30 minutes from the time the sample is collected (e.g., the time of injury or suspected injury). In yet other aspects, the result is communicated in about 4 minutes to about 20 minutes from the time the sample is collected (such as, for example, from the time of injury or suspected injury). In some aspects, the result is communicated in about 40 minutes or less, about 39 minutes or less, about 38 minutes or less, about 37 minutes or less, about 36 minutes, or less about 35 minutes, less about 34 minutes or less, about 33 minutes or less, about 32 minutes or less, about 31 minutes or less, about 30 minutes or less, about 29 minutes or less, about 28 minutes or less, about 27 minutes or less, about 26 minutes or less, about 25 minutes or less, about 24 minutes or less, about 23 minutes or less, about 22 minutes or less, about 21 minutes or less, about 20 minutes, about 19 minutes, about 18 minutes, about 17 minutes, about 16 minutes, about 15 minutes, about 14 minutes, about 13 minutes, about 12 minutes, about 11 minutes, about 10 minutes, about 9 minutes, about 8 minutes, about 7 minutes, about 6 minutes, about 5 minutes, or about 4 minutes from the time the sample is collected (such as, for example, from the time of injury or suspected injury).

In some aspects, the instrument contains software to execute one or more tasks, including the performance of the methods and algorithms described herein. In some aspects, the instrument contains software to automatically determine the next appropriate step in a methods and algorithms as described herein. For example, the instrument may contain software that determines the amount or presence of an analyte of interest. The software may display this determination, such as on a graphical user interface.

In some aspects, the instrument stores software that instructs a processor to execute a given task. In some aspects, the software stores machine readable instructions that instruct a processor to execute a given task. The machine-readable instructions may be one or more executable programs or portion(s) of an executable program for execution by a computer. The programs may be embodied in software stored on a non-transitory computer readable storage medium such as a CD-ROM, a floppy disk, a hard drive, a DVD, a Blu-ray disk, or a memory associated with the processors. Alternatively, the entire programs and/or parts thereof could alternatively be executed by a device other than the processors and/or embodied in firmware or dedicated hardware. Additionally or alternatively, processes may be implemented by one or more hardware circuits (e.g., discrete and/or integrated analog and/or digital circuitry, an FPGA, an ASIC, a comparator, an operational-amplifier (op-amp), a logic circuit, etc.) structured to perform the corresponding operation without executing software or firmware.

The machine-readable instructions may be stored in one or more of a compressed format, an encrypted format, a fragmented format, a compiled format, an executable format, a packaged format, etc. Machine readable instructions as described herein may be stored as data (e.g., portions of instructions, code, representations of code, etc.) that may be utilized to create, manufacture, and/or produce machine executable instructions. For example, the machine-readable instructions may be fragmented and stored on one or more storage devices and/or computing devices (e.g., servers). The machine-readable instructions may require one or more of installation, modification, adaptation, updating, combining, supplementing, configuring, decryption, decompression, unpacking, distribution, reassignment, compilation, etc. in order to make them directly readable, interpretable, and/or executable by a computing device and/or other machine. For example, the machine-readable instructions may be stored in multiple parts, which are individually compressed, encrypted, and stored on separate computing devices, wherein the parts when decrypted, decompressed, and combined form a set of executable instructions that implement a program such as that described herein.

In another example, the machine-readable instructions may be stored in a state in which they may be read by a computer, but require addition of a library (e.g., a dynamic link library (DLL)), a software development kit (SDK), an application programming interface (API), etc. in order to execute the instructions on a particular computing device or other device. In another example, the machine-readable instructions may need to be configured (e.g., settings stored, data input, network addresses recorded, etc.) before the machine-readable instructions and/or the corresponding program(s) can be executed in whole or in part. Thus, the disclosed machine-readable instructions and/or corresponding program(s) are intended to encompass such machine-readable instructions and/or program(s) regardless of the particular format or state of the machine-readable instructions and/or program(s) when stored or otherwise at rest or in transit.

The machine-readable instructions described herein can be represented by any past, present, or future instruction language, scripting language, programming language, etc. For example, the machine-readable instructions may be represented using any of the following languages: C, C++, Java, C#, Perl, Python, JavaScript, HyperText Markup Language (HTML), Structured Query Language (SQL), Swift, etc.

The machine readable instructions may be stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media.

In some aspects, the GFAP assay described herein is used in combination with an assay for UCH-L1 that does not employ a cartridge comprising a magnetic immunosensor, the reference level for UCH-L1 is from about 320 to about 400 pg/mL. In other aspects, the reference level for UCH-L1 is about 360 pg/mL. In still further aspects, the reference level for UCH-L1 is about 400 pg/mL.

In some aspects, the reference level for UCH-L1 is from about 320 to about 400 pg/mL and the sample is obtained from the subject within about 24 hours or less. In other aspects, the reference level for UCH-L1 is about 360 pg/mL and the sample is obtained from the subject within about 24 hours or less. In yet other aspects, the reference level for UCH-L1 is about 400 pg/mL and the sample is obtained from the subject within about 24 hours or less.

In some aspects, the reference level for GFAP is from about 25 to about 40 pg/mL. In other aspects, the reference level for GFAP is about 30 pg/mL. In still further aspects, the reference level for GFAP is about 35 pg/mL.

In some aspects, the reference level for GFAP is from about 25 to about 40 pg/mL and the sample is obtained from the subject within about 24 hours or less. In other aspects, the reference level for GFAP is about 30 pg/mL and the sample is obtained from the subject within about 24 hours or less. In yet other aspects, the reference level for GFAP is about 35 pg/mL and the sample is obtained from the subject within about 24 hours or less.

In some aspects, the reference level for UCH-L1 is about 360 pg/mL and the reference level for GFAP is about 30 pg/mL. In yet other aspects, the reference level for UCH-L1 is about 400 pg/mL and the reference level for GFAP is about 35 pg/mL. In still further aspects, the reference level for UCH-L1 is about 360 pg/mL and the reference level for GFAP is about 30 pg/mL and the sample is obtained from the subject within about 24 hours or less. In yet other aspects, the reference level for UCH-L1 is about 400 pg/mL and the reference level for GFAP is about 35 pg/mL and the sample is obtained from the subject within about 24 hours or less.

In some aspects, the method comprises performing at least one assay for GFAP and at least one assay for UCH-L1 in at least one sample obtained from the subject, and determining whether the amount (e.g., level) of GFAP and UCH-L1 in the subject is elevated based upon the results of the assays. In some aspects, the method comprises determining that the amount of GFAP and UCH-L1 in the subject is elevated. In some aspects, the method comprises determining that the amount of GFAP and UCH-L1 in the subject is elevated when the amount of GFAP in the sample is equal to or above 30 pg/mL and the level of UCH-L1 is below about 360 pg/mL, cannot be determined by the assay for UCH-L1, or is not reported by the assay for UCH-L1. In some aspects, the method comprises determining that the amount of GFAP and UCH-L1 in a sample obtained from a subject is elevated when the level of GFAP is equal to or above about 30 pg/mL and level of UCH-L1 is equal to or above about 360 pg/mL. In some aspects, the method comprises determining that the amount of GFAP and UCH-L1 in the subject is elevated when the level of GFAP cannot be determined by the assay for GFAP or is not reported by the assay and the level of UCH-L1 is equal to or above about 360 pg/mL.

In some aspects, the method comprises determining that the amount of GFAP and UCH-L1 in the subject not elevated. In some aspects, the method comprises determining that the amount of GFAP and UCH-L1 in the subject is not elevated when the level of GFAP in the sample is below about 30 pg/mL and level of UCH-L1 in the sample is below about 360 pg/mL. In some aspects, the method comprises determining that the assays for GFAP and UCH-L1 should be repeated. In some aspects, the method comprises determining that the assays for GFAP and UCH-L1 or GFAP should be repeated when the amount of GFAP is below about 30 pg/mL and the level of UCH-L1 cannot be determined by the assay for UCH-L1 or is not reported by the assay for UCH-L1. In some aspects, the method comprises determining that the assays for GFAP and UCH-L1 or GFAP should be repeated when the amount of GFAP cannot be determined by the assay or is not reported by the assay for GFAP and the level of UCH-L1 is below about 360 pg/mL. In some aspects, the method comprises determining that the assays for GFAP and UCH-L1 or GFAP should be repeated when the amount of GFAP cannot be determined by the assay for GFAP or is not reported by the assay for GFAP and the level of UCH-L1 cannot be determined by the UCH-L1 or is not reported by the assay for UCH-L1.

In some aspects, the method comprises performing at least one assay for GFAP and at least one assay for UCH-L1 in at least one sample obtained from the subject, and determining whether the amount of GFAP and UCH-L1 in the subject is elevated based upon the results of the assays. In some aspects, the method comprises determining that the amount of GFAP and UCH-L1 in the subject is elevated. In some aspects, the method comprises determining that the amount of GFAP and UCH-L1 in the subject is elevated when the amount of GFAP in the sample is equal to or above 35 pg/mL and the amount of UCH-L1 is below about 400 pg/mL, cannot be determined by the assay for UCH-L1, or is not reported by the assay for UCH-L1. In some aspects, the method comprises determining that the amount of GFAP and UCH-L1 in the subject is elevated when the amount of GFAP is equal to or above about 35 pg/mL and level of UCH-L1 is equal to or above about 400 pg/mL. In some aspects, the method comprises determining that the amount GFAP and UCH-L1 in the subject is elevated when the amount of GFAP cannot be determined by the assay for GFAP or is not reported by the assay and the amount of UCH-L1 is equal to or above about 400 pg/mL.

In some aspects, the method comprises determining that the amount of GFAP and UCH-L1 in the subject is not elevated. In some aspects, the method comprises determining that the amount of GFAP and UCH-L1 in the subject is not elevated when the amount of GFAP in the sample is below about 35 pg/mL and amount of UCH-L1 in the sample is below about 400 pg/mL.

In some aspects, the method comprises determining that the assays for GFAP and UCH-L1 or GFAP should be repeated. In some aspects, the method comprises determining that the assays for GFAP and UCH-L1 or GFAP should be repeated when the amount of GFAP is below about 35 pg/mL and the amount of UCH-L1 cannot be determined by the assay for UCH-L1 or is not reported by the assay for UCH-L1. In some aspects, the method comprises determining that the assays for GFAP and UCH-L1 or GFAP should be repeated when the amount of GFAP cannot be determined by the assay for GFAP or is not reported by the assay for GFAP and the amount of UCH-L1 is below about 400 pg/mL. In some aspects, the method comprises determining that the assays for GFAP and UCH-L1 or GFAP should be repeated when the amount of GFAP cannot be determined by the assay for GFAP or is not reported by the assay for GFAP and the amount of UCH-L1 cannot be determined by the UCH-L1 or is not reported by the assay for UCH-L1.

In some aspects, the method further comprises performing a head computed tomography (CT) scan, a magnetic resonance imaging (MRI) procedure, or both a CT scan or a MRI procedure on the subject when the subject's levels of GFAP, or GFAP and UCH-L1 are elevated. For example, in some aspects, the method further comprises performing a head CT scan on the subject when the subject's levels of GFAP, or GFAP and UCH-L1 are elevated. As another example, in some aspects, the method further comprises performing an MRI procedure on the subject when the subject's levels of GFAP, or GFAP and UCH-L1 are elevated. In some aspects, the method further comprises performing a head CT scan and an MRI procedure on the subject when the subject's levels of GFAP or GFAP and UCH-L1 are elevated.

B. Point-of-Care Device Comprising a Magnetic Immunosensor

As mentioned previously herein, the systems and assays of the present disclosure utilize a point-of-care device. Examples of suitable point-of-care devices that can be used in the systems and assays described herein include, for example, i-STAT and i-STAT Alinity devices marketed by Abbott Laboratories.

The point-of-care devices used in the systems and assays of the present disclosure contain at least one cartridge which comprises at least one magnetic immunosensor or magnetic immunosensing device. In some aspects, the at least one magnetic immunosensor or magnetic immunosensing device includes a base sensor or sensing electrode. In some aspects, the base sensor or sensing election can be on a substantially planar chip (e.g., an immunosensor or sensor chip) where the sensing electrode is positioned in a conduit for receiving a biological sample (e.g., a blood sample such as a venous blood sample, a capillary blood sample, a fingerstick blood sample, or a combination thereof) and is mixed with magnetically susceptible beads that can be attracted to a magnet, or respond to a magnetic field.

A high-field magnet, e.g., a permanent magnet or an electromagnet, is positioned proximate to the chip, incorporated into the chip, or on the chip (e.g., on top of the chip or underneath or below the chip) for attracting the magnetically susceptible beads in the conduit substantially proximate to the sensing electrode. This magnetic zone functions to capture and substantially retain the beads at or near the sensing electrode surface such as, for example, during removal of any unbound sample and washing of the electrode. As described in detail herein, the beads are coated with at least one first specific binding partner (e.g., an anti-GFAP antibody, or an anti-GFAP antibody and an anti-UCH-L1 antibody) that specifically binds to an analyte (e.g., GFAP) in said sample. In some aspects, the at least one first specific binding partner is an anti-GFAP antibody. In another aspect, the at least one first specific binding partner is an anti-UCH-L1 antibody.

In yet further aspects, in addition to the magnetic immunosensor or magnetic immunosensing device, the cartridge further comprises one or more areas or regions that contain: (a) one or more beads (e.g., paramagnetic particles) coated with the at least one first specific binding partner (e.g., an anti-GFAP antibody) that specifically binds to an analyte (e.g., GFAP) that is printed or dispensed on the cartridge and dried using routine techniques known in the art; and (b) at least one detectably labeled second specific binding partner (e.g., an anti-GFAP antibody) that is printed or dispensed on the cartridge and dried using routine techniques known in the art. The one or more beads containing the at least one first specific binding partner (e.g., an anti-GFAP antibody) and the detectably labeled at least one second specific binding partner (e.g., an anti-GFAP antibody) can be printed and dried in the same area or region on the cartridge, or alternatively, in an area or region adjacent or in close proximity to one another.

In some aspects, during performance of the assay, the printed beads containing the at least one first specific binding partner (e.g., an anti-GFAP antibody) and printed detectably labeled at least one second specific binding partner (e.g., an anti-GFAP antibody) are reconstituted by wetting or dissolving the printed area with at least one diluent, buffer, or other liquid. Once reconstituted, the sample can be added and mixed with the beads and detectable label. In other aspects, the printed beads and the label can be reconstituted using the sample, thereby allowing for reconstitution and mixing to occur simultaneously. Once the sample is mixed with the beads coated with the at least one first specific binding partner and the detectably labeled at least one second specific binding partner, complexes comprising the first specific binding partner coated beads-analyte-detectable labeled second specific binding partner are formed. Once formed, the magnet contained in or on the cartridge is used to capture and retain the beads containing the complexes and the amount of analyte (e.g., GFAP) determined using routine techniques known in the art. In some aspects, the magnet may be positioned on top of the chip. In other aspects, the magnet may be positioned below or beneath the chip.

Additionally, in some other aspects, the point-of-care device comprises a reading apparatus or reader and a single-use cartridge containing the magnetic immunosensor or immunosensing device and all the other assay components used to analyze an analyte in a biological sample.

(1) High-Field Magnets and Magnetic Layers

In some aspects, the at least one magnetic immunosensor comprises a sensing electrode on a substantially planar chip and has a high-field magnet, e.g., a permanent magnet or an electromagnet, positioned proximate to (e.g., below) or associated with the chip. The magnetic immunosensor can provide a field of greater than about 0.1 Tesla and has an event horizon (e.g., a point of no return) that can efficiently draw beads from a range of about 0.05 mm to about 5 mm in the region of the sensing electrode.

The high-field magnet, such as a permanent magnet or electromagnet, includes any material that provides a high magnetic field (e.g., greater than about 0.1 Tesla, greater than 0.4 Tesla or greater than 1 Tesla). The magnetic field can be measured, for example, as the remnant field on a substantially flat surface area of a magnet. Examples of material that can be used include a neodymium iron boron alloy (NdFeB) alloy or $Nd_2Fe_{14}B$, although, other materials may be used. For example, high-field permanent magnets can include ferrite or aluminum nickel cobalt (AlNiCo) magnets, which typically exhibit fields of 0.1 to 1 Tesla. Other high-field permanent magnets comprised of alloys of rare earth elements (e.g., neodymium alloys and samarium cobalt (SmCo) alloys) exhibit fields in excess of 1 Tesla, e.g., greater than 1.2 Tesla or greater than 1.4 Tesla.

Rare earth magnets are generally brittle and also vulnerable to corrosion, and as such, these materials are frequently plated or coated to protect them from breaking and chipping. In addition, the Curie point of rare earth magnets is substantially above the temperatures encountered in the assays described herein which may be run at ambient temperature to about 50° C. In some aspects, the assays are thermostated at 37° C. for use with blood samples (such as a venous blood sample, a capillary blood sample, a fingerstick blood sample, or a combination thereof).

In another aspect, the high-field magnet comprises an electromagnet in which the magnetic field is produced by the flow of electric current. The electric current may be provided by a reader in the point-of-care device, in which the magnetic immunosensor or magnetic immunosensing device is inserted and with which the magnetic immunosensor or magnetic immunosensing device is in electrical contact.

The magnetic immunosensor or magnetic immunosensing device comprises a sensing electrode on a substantially planar chip and a bulk permanent high-field magnet positioned proximate to the electrode (e.g., below or on the opposite side of the chip). In some aspects, the bulk permanent high-field magnet is positioned in the housing (e.g., cut out or trench in the plastic cartridge) of the point-of-care device. In yet other aspects, the bulk permanent high-field magnet is positioned within the base of the plastic cartridge housing (e.g., non-coplanar with the sensing electrode). In other aspects, the magnet is positioned adjacent to or within the reading apparatus or reader in the point-of-care device.

In some aspects, the bulk high-field permanent magnet is substantially cylindrical, having a diameter in the range of about 0.1 mm to about 5 mm and a length of about 0.1 mm to about 5 mm, and is positioned to yield an event horizon in the conduit suitable for bead capture within a short period of time (e.g., 1-5 minutes). The conduit generally has a height of about 0.2 mm to about 5 mm and a width of about 0.2 mm to about 5 mm, and either a uniform or non-uniform cross-sectional area. In other embodiments, the bulk magnet shape may be in the form of a square, rectangle, oval, flake, pyramid, sphere, sub-sphere, or other shaped form.

In yet another aspect, the magnetic immunosensor or magnetic immunosensing device comprises a sensing electrode on a substantially planar chip. The electrode is positioned in a conduit for receiving a sample which has been mixed with one or more first specific binding partners (e.g., an antibodies) immobilized on magnetically susceptible beads and one or more labeled second specific binding partners and a magnetized layer (e.g., microfabricated magnetic layer). The magnetized (or magnetic) layer may be included on (e.g., positioned over, directly attached, coated or patterned onto any surface of the chip) or embedded into the chip (e.g., positioned within the chip, integral to the chip). This configuration attracts the magnetically susceptible beads substantially proximate to the electrode and substantially retains them at the electrode during removal of unbound sample and washing of the electrode.

The magnetized layer can be formed from a mobile magnetic composition, e.g., a slurry, comprising a material capable of sustaining a high-field permanent magnetic field, e.g., a NdFeB alloy, as particles in an immobilization or support matrix (e.g., a polyimide, polyvinyl alcohol (PVA) or thermoplastic equivalent). This slurry is not limited by viscosity and can include any viscosity that is known to be suitable in the art. In some aspects, the mobile magnetic composition has a viscosity ranging from 0.3 to 300,000 CPS, e.g., from 100 to 100,000 CPS or from 1,000 to 10,000 CPS. In other aspect, the magnetic particles in the slurry have an average particle size from 0.01 m to 100 m, e.g., from 0.1 m to 10 m or from 3 m to 7 m.

In addition to polyimide, PVA and thermoplastic polyimide, two-part chemically cured epoxy resins, kapton and the like may be used as the support matrix for fixing the magnetic particles to the wafer. The methods of curing the matrix may be based on a photo-initiated, thermally initiated or chemically initiated process. In certain embodiments, the immobilization matrix is comprised of other photoformed matrix materials.

As discussed above, the slurry can be applied in a variety of locations in or on the immunosensing device (e.g., to the front side or backside of a wafer or chip, electrode, housing, reader, etc.). For example, in some aspects, the high-field permanent magnetic material is applied to the substantially planar chip in a patterned manner (e.g., using a mask). In certain aspects, the high-field permanent magnetic material is also applied to a microfabricated sensing electrode. In other aspects, the slurry is applied in a layer below the sensing electrode.

Prior to the application process, the slurry may or may not be magnetized. However, after the deposition step, the magnetic layer can be magnetized to provide directionality to the field.

(2) Sensing Electrode

The sensing electrode can be microfabricated (e.g., an amperometric gold array) on a substantially planar chip (e.g., silicon wafer) using any technique known in the art, such as, for example, that described in U.S. Pat. Nos. 5,200,051 and 7,419,821, the contents of which are herein incorporated by reference.

(3) Magnetically Susceptible Beads

In some aspects, the biological sample, e.g., blood sample, is mixed with magnetically susceptible beads. The magnetically susceptible beads may be comprised of any material known in the art that is susceptive to movement by a magnet (e.g., permanent magnet or electromagnet) utilized in or in concert with the device of the present disclosure. As such, the terms "magnetic" and "magnetically susceptible" with regard to beads can be used interchangeably.

In some aspects, the beads include a magnetic core, which can be completely or partially coated with a coating material. The magnetic core may comprise a ferromagnetic, paramagnetic or a superparamagnetic material. In some aspects, the magnetically susceptible beads comprise a ferrite core and an outer polymer coating. However, the magnetic core may comprise one or more of Fe, Co, Mn, Ni, metals comprising one or more of these elements, ordered alloys of these elements, crystals comprised of these elements, magnetic oxide structures, such as ferrites, and combinations thereof. In other aspects, the magnetic core may be comprised of magnetite ($Fe_3O_4$), maghemite ($\gamma$-$Fe_2O_3$), or divalent metal-ferrites provided by the formula $Me_{1-x}OFe_3+x\,O_3$ where Me is, for example, Cu, Fe, Ni, Co, Mn, Mg, or Zn or combinations of these materials, and where x ranges from 0.01 to 99.

Suitable materials for the coating include synthetic and biological polymers, copolymers and polymer blends, and inorganic materials. Polymer materials may include various combinations of polymers of acrylates, siloxanes, styrenes, acetates, akylene glycols, alkylenes, alkylene oxides, parylenes, lactic acid, and glycolic acid. Biopolymer materials include starch or similar carbohydrate. Inorganic coating materials may include any combination of a metal, a metal alloy, and a ceramic. Examples of ceramic materials may include hydroxyapatite, silicon carbide, carboxylate, sulfonate, phosphate, ferrite, phosphonate, and oxides of Group IV elements of the Periodic Table of Elements.

In other aspects, the magnetic beads comprise non-magnetic substrate beads formed, for example, of a material selected from the group consisting of polystyrene, polyacrylic acid and dextran, upon which a magnetic coating is placed.

Any correctly-sized magnetically susceptible bead capable of being positioned with the high-field magnet of the as described may be utilized, taking into account the dispersability requirements for the magnetically susceptible beads. In some aspects, at least 50 wt. %, e.g., at least 75 wt. %, of the magnetically susceptible beads are retained at the electrode surface. In some aspects, the average particle size of the magnetically susceptible beads may range from 0.01 m to 20 m, e.g., from 0.1 m to 10 m, from 0.1 m to 5 m or from 0.2 m to 1.5 m. As used herein, the term "average particle size" refers to the average longest dimension of the particles, e.g., beads, for example the diameter for spherical particles, as determined by methods well-known in the art. The particle size distribution of the magnetically susceptible beads can be unimodal, although polymodal distributions may also be used. While spherical magnetically susceptible bead can be used, other bead shapes and structures, e.g., ovals, sub-spherical, cylindrical and other irregular shaped particles, are within the meaning of the term "beads" and "microparticles" as used herein.

Commercial sources for magnetically susceptible beads include Invitrogen™ (Carlsbad, Calif., U.S.A.) by Life Technologies™, Ademtech (Pessac, France), Chemicell GmbH (Berlin, Germany), Bangs Laboratories, Inc.™, (Fishers, Ind.) and Seradyn, Inc. (Indianapolis, Ind.). Many of the commercially available products incorporate surface functionalization that can be employed to immobilize antibodies (e.g., IgG) on the bead surfaces. Exemplary functionalizations include carboxyl, amino or streptavidin-modified magnetically susceptible beads.

In some aspects, the magnetically susceptible beads are coated with an antibody, such as an anti-GFAP antibody. The coating of the beads with the antibody immobilizes the antibody on the bead.

In certain aspects, the magnetically susceptible beads are deposited in a suitable region of the magnetic immunosensing device as a suspension in, for example, a mixture of lactitol and DEAE-dextran such as that supplied by Advanced Enzyme Technologies (Pontypool, Great Britain). Evaporation of the solvent, usually water, yields a glassy deposit in which the beads are immobilized. The lactitol/DEAE-dextran allows the beads to be regionalized within the device in a mechanically and biochemically stable state, but which also rapidly dissolves upon contact with a sample.

In various aspects, the beads are mobile and thereby capable of interacting with an analyte. After binding to GFAP, magnetic forces are used to concentrate the beads at the electrode for measurement causing the magnetically susceptible beads to be localized to the amperometric electrode for signal detection.

(4) Manufacture of Magnetic Immunosensor or Magnetic Immunosensing Device

The magnetic immunosensor or immunosensing device can be manufactured using techniques known in the art, including, for example, those described in U.S. Pat. Nos. 9,233,370, 9,958,440, and 10,145,843 and International Patent Publication Nos.: WO18107016, WO18107015, WO18107007, WO18107009, WO18107012, WO18107013, WO21211331, and WO21211332, the contents of which are herein incorporated by reference. For example, a silicon wafer is thermally oxidized to form an insulating oxide layer having a thickness of about 1 m. A titanium/tungsten layer is then sputtered onto the oxide layer to a preferable thickness of about 100 Å to about 1000 Å, followed by a layer of gold that is from 500 Å to 1000 Å thick, most preferably about 800 Å thick. Next, a photoresist is spun onto the wafer and is dried and baked. The surface is then exposed using a contact mask, the latent image is developed, and the wafer is exposed to a gold-etchant. The patterned gold layer is coated with a photodefinable polyimide, suitably baked, exposed using a contact mask, developed, cleaned in an oxygen plasma, and preferably imidized at 350° C. for about 5 hours. This leaves a large number of electrode openings in the polyimide layer in a square array. In some embodiments, the square array has a diameter, for example, from about 2 m to about 100 m, from about 5 m to about m or about 7 m, with an inter-distance of, for example, from about 5 m to about 100 m, from about 10 m to about 20 m or about 15 m. The area covered by these electrodes (i.e., sensor area) is substantially circular with a diameter of, for example, from about 50 m to about 1000 m, from about 100 m to about 300 m or about 300 m.

After dicing the wafer into individual chips, each chip is assembled into a single-use cartridge. The cartridges may be of the type described in U.S. Pat. Nos. 7,419,821, 8,747,774 and 9,415,389, which are herein incorporated by reference. In one aspect, the sensor is positioned in a conduit for receiving a sample, and a high-field magnet, e.g., permanent or electromagnet, is positioned directly below the sensor, such as in the center region thereof. In another aspect, a high-field magnet can be positioned above the sensor region of the conduit. These elements may be in a fixed position within the instrument housing, or adapted to an actuator capable of moving in and out of position with respect to the immunosensor and conduit. The one or more high-field magnets can be used for attracting magnetically susceptible beads in the conduit (e.g., substantially proximate to the sensor) and retaining them in the region of the sensor during removal of sample and washing of the sensor to remove unbound or partially absorbed reagents. As described above, the magnetic beads are coated with an antibody (e.g., an anti-GFAP antibody) to detect GFAP in the sample.

C. Systems

In another embodiment, the present disclosure relates to a system for determining the amount of GFAP in a biological system obtained from a subject. In some aspects, the system utilizes the assay described in Section 2(A), which utilizes a at least one magnetically susceptible bead. Additionally, the system utilizes a point-of-care device containing at least one cartridge which comprises at least one magnetic immunosensor or immunosensing device as described in Section 2(B). The point-of-care device determines the amount of GFAP in the sample by magnetically capturing and retaining the bead containing the complexes on the at least one magnetic immunosensor and assesses the signal from the complexes where the amount of detectable signal from the detectable label indicates the amount of GFAP in the sample. In further aspects, it has been found that when the system uses the GFAP assay described in Section 2A, that the assay exhibits at least a 5-fold increase in sensitivity when compared to assays for GFAP that do not immobilize the first specific binding partner on a magnetically susceptible bead and magnetically capture and retain the bead containing complexes on at least one magnetic immunosensor in a cartridge contained in a point-of-care device. In some aspects, it has been found that assays for measuring GFAP as described in Section 2A exhibit at least a 6-fold, at least a 7-fold, at least an 8-fold, at least a 9-fold, at least a 10-fold, at least a 11-fold, at least a 12-fold, at least a 13-fold, at least a 14-fold, or at least a 15-fold increase in sensitivity when compared to an assay that does not immobilize the first specific binding partner on a magnetically susceptible bead and magnetically capture and retain the bead containing the complexes on at least one magnetic immunosensor in a cartridge contained in a point-of-care device.

3. Plasma Separation Apparatus

As discussed previously, in some aspects of the systems and assays described herein, an apparatus that is a plasma separation device can be used to process the biological sample (e.g., blood sample). In one aspect, the apparatus comprises a hydrophobic layer comprising at least one microchannel and a top layer that flanks or is positioned above or on top of the hydrophobic layer. The hydrophobic layer can comprise or be constructed from at least one hydrophobic material. The hydrophobic material can be a membrane, film, fabric, fiber, filter, microfilm, screen, mesh, or any combination thereof. In one aspect, the hydrophobic layer is a membrane or film. Hydrophobic membranes or films that can be used are those known in the art. Specifically, membranes or films such as those available from Adhesive Research (Glen Rock, PA), 3M (Minneapolis, Minnesota), and/or Tesa SE (Norderstadt, Germany) can be used.

The hydrophobic layer comprises at least one microchannel having a first and second end which defines a path for capillary fluid flow of a processed blood sample or blood product (e.g., plasma). In some aspects, at least one microchannel extends longitudinally along a portion of the hydrophobic layer from the first end to an opening at the second (e.g., opposite) end of the microchannel. In other aspects, the at least one microchannel extends the width of a portion of the hydrophobic layer from the first end to an opening at the second (e.g., opposite) end of the microchannel. In some aspects, the microchannel contains a first opening connected to the first end of the microchannel. In these aspects, the processed blood or blood product (e.g., plasma) can flow from the first opening into the first end of the microchannel to the second opening at the second end of the microchannel.

The opening at the second end of the microchannel allows the processed blood or blood product (e.g., plasma) to flow out of the apparatus. For example, if the fluid being processed is blood, plasma can flow from the first end towards the second opening at the second (e.g., opposite) end by capillary fluid flow. The plasma can be collected at the second (e.g., opposite) end using a collection or other device or, if the apparatus is operably linked, removably coupled, or in fluid communication with another device (such as a sample analysis cartridge (such as a microfluidic cartridge)), allowed to continue to flow directly on or into the device for further processing and/or analysis.

The microchannel can be of any length. In some aspects, the microchannel is less than about 80 mm in length. In yet other aspects, the at least one microchannel is about 70 mm in length, the at least one microchannel is about 60 mm in length, about 55 mm in length, about 50 mm in length, about 45 mm in length, about 40 mm in length, about 35 mm in length, about 30 mm in length, about 25 mm in length, about 20 mm in length or about 15 mm in length. In yet other aspects, the at least one microchannel is less than about 5 mm wide, less than about 4.5 mm wide, less than about 4 mm wide, about 3 mm wide, less than about 2.5 mm wide, or less than about 2.0 mm wide.

Additionally, the at least one microchannel can be positioned at any location on the hydrophobic layer. For example, the at least one microchannel can be centered on the hydrophobic layer, it can be slightly off center on the hydrophobic layer, or it can be at or close to a side or edge of the hydrophobic layer.

In yet additional aspects, the hydrophobic layer can have a thickness of about 50 to about 200 microns. In yet other aspects, the hydrophobic layer can have a thickness of about 100 to about 200 microns. In some aspects, the hydrophobic layer can have a thickness of about 100 to about 150 microns.

The apparatus also comprises a top layer that flanks or is positioned above or on top of the hydrophobic layer. In some aspects, the top layer is adherent to the hydrophobic layer. In yet further aspects, the surface of the top layer that faces the hydrophobic layer comprises a material or is coated with a hydrophilic material. The hydrophilic material can be an adhesive, membrane, film, fabric, fiber, filter, microfilm, screen, mesh, or any combination thereof. In other aspects, the entire top layer is made or constructed of a hydrophilic material such as a membrane, film, fabric, fiber, filter, microfilm, screen, mesh, or any combination thereof. For example, in one aspect, the top layer is a membrane or film. In some aspects, the membrane or film is not constructed from a hydrophilic material but is coated with a hydrophilic material. The portion of the top layer coated with the hydrophilic material faces the hydrophobic layer. In another aspect, the entire membrane or film is made or constructed from a hydrophilic material. Hydrophilic membranes or films that can be used are those known in the art. An example of hydrophilic film that can be used is 9984 Diagnostic Microfluidic Surfactant Free Hydrophilic Film available from 3M (Minneapolis, MN), Kemafoil H, Hydrophilic coated polyester film from Coveme (S. Lazzaro diSavena, Italy), Tesa 62580, Hydrophilic coated polyester film from Tesa SE (Norderstadt, Germany). In yet additional aspects, the top layer can have a thickness of about 50 to about 200 microns. In yet other aspects, the top layer can have a thickness of about 100 to about 200 microns. In some aspects, the top layer can have a thickness of about 100 to about 150 microns.

When a blood sample or blood product is placed on the top layer of the apparatus, the blood sample or product flows through the top layer. As it does so, cellular components of the blood (e.g., red blood cells, white blood cells, platelets, and combinations thereof) are captured in the pores and/or fibers of the hydrophilic material thereby allowing the plasma to continue to flow through the hydrophilic material to the hydrophobic layer and into the microchannel. Once in the microchannel, the plasma flows by capillary fluid flow from the first end to the opening at the second (e.g., opposite) end of the channel. The plasma can be collected using a collection or other device, or, if the apparatus is operably linked, removably coupled, or in fluid communication with another device (such as a sample analysis cartridge (e.g., a microfluidic cartridge), allowed to continue to flow directly on or into the device for further processing and analysis.

In another aspect, the apparatus optionally comprises a bottom layer. The bottom layer is flanked or is positioned below or beneath the hydrophobic layer. In these aspects, the apparatus comprises at least three layers—a top layer, a hydrophobic layer, and a bottom layer. In some aspects, the bottom layer is adherent to the hydrophobic layer. In additional aspects, the top layer and bottom layer are each adherent to the hydrophobic layer.

In yet further aspects, the surface of the bottom layer that faces the hydrophobic layer comprises a material or is coated with a hydrophilic material. The hydrophilic material can be an adhesive, membrane, film, fabric, fiber, filter, microfilm, screen, mesh, or any combination thereof. In other aspects, the entire bottom layer is made or constructed from a hydrophilic material such as a membrane, film, fabric, fiber, filter, microfilm, screen, mesh, or any combination thereof. For example, in one aspect, the bottom layer is a membrane or film. In some aspects, the membrane or film is not constructed from a hydrophilic material but is coated with a hydrophilic material. The portion of the bottom layer coated with the hydrophilic material faces the hydrophobic layer. In another aspect, the entire membrane or film is made or constructed from a hydrophilic material. Hydrophilic membranes or films that can be used are those known in the art. An example of hydrophilic film that can be used is 9984 Diagnostic Microfluidic Surfactant Free Hydrophilic Film available from 3M (Minneapolis, MN), Kemafoil H, Hydrophilic coated polyester film from Coveme (S. Lazzaro diSavena, Italy), Tesa 62580, Hydrophilic coated polyester film from Tesa SE (Norderstadt, Germany).

In yet additional aspects, the bottom layer can have a thickness of about 50 to about 200 microns. In yet other aspects, the bottom layer can have a thickness of about 100 to about 200 microns. In some aspects, the bottom layer can have a thickness of about 100 to about 150 microns.

In still further aspects, the apparatus can contain a protective film which flanks or is positioned below or beneath the bottom layer. In some aspects, the protective film is adherent to the bottom layer. The protective film protects the apparatus from moisture and/or other contamination. The protective film can be a plastic film, such as a self-adhesive plastic film, cardboard with adhesive, a plastic sheet with adhesive, or combinations thereof.

In yet other aspects, when the apparatus contains a top layer, a hydrophobic layer and a bottom layer, the combined thickness of the three layers is between about 100 to about 600 microns. In other aspects, the combined thickness of the three layers is between about 150 to about 600 microns. In other aspects, the combined thickness of the three layers is between about 200 to about 600 microns. In yet other aspects, the combined thickness of the three layers is between about 150 to about 500 microns. Still yet further aspects, the combined thickness of the three layers is between about 200 to about 500 microns.

Additionally, in some aspects, when the apparatus contains a top layer, a hydrophobic layer and a bottom layer, the top layer and the bottom layer can be made from the same material. Alternatively, the top layer and the bottom layer can be made from different materials. For example, the top layer and bottom layer can be made or constructed from the same hydrophilic material or different hydrophilic materials. Alternatively, the top and bottom layers may be made or constructed from a material that is not hydrophilic but are coated with a hydrophilic material on the surface of the layer that faces the hydrophobic layer. Still further, either one of the top or bottom layers may be made or constructed from a material that is not hydrophilic and coated with a hydrophilic material on the surface facing the hydrophobic layer and the other layer made entirely from a hydrophilic material.

In some aspects, the top layer comprises a sample inlet where the blood sample or blood product is placed to begin the sample processing through the apparatus. The sample inlet can have any shape. For example, the sample inlet can be round, oval, rectangular, square, triangular, or any combination thereof. In some aspects, a hydrophobic transfer material (e.g., such as a transfer tape) can surround the sample inlet. The hydrophobic transfer material helps prevent the blood sample or blood product from wicking or moving away from the sample inlet area.

When the top layer comprises a sample inlet, the hydrophobic layer and optionally, the bottom layer, comprise one or more openings. The openings can have any shape. For example, the opening can be round, oval, rectangular, square, triangular, or any combination thereof. The opening can have the same shape as the sample inlet or it can have a different shape. In some aspects, when the apparatus contains two layers (e.g., a top layer having a sample inlet and a hydrophobic layer), one or more openings can be made in the hydrophobic layer. In yet other aspects, when the apparatus contains three layers, one or more openings can be made in the hydrophobic layer but not in the bottom layer. In other aspects, when the apparatus contains three layers, one or more openings can be made in each of the hydrophobic layer and bottom layer. Each opening in the one or more layers can be directly below the sample inlet.

Figure 8:
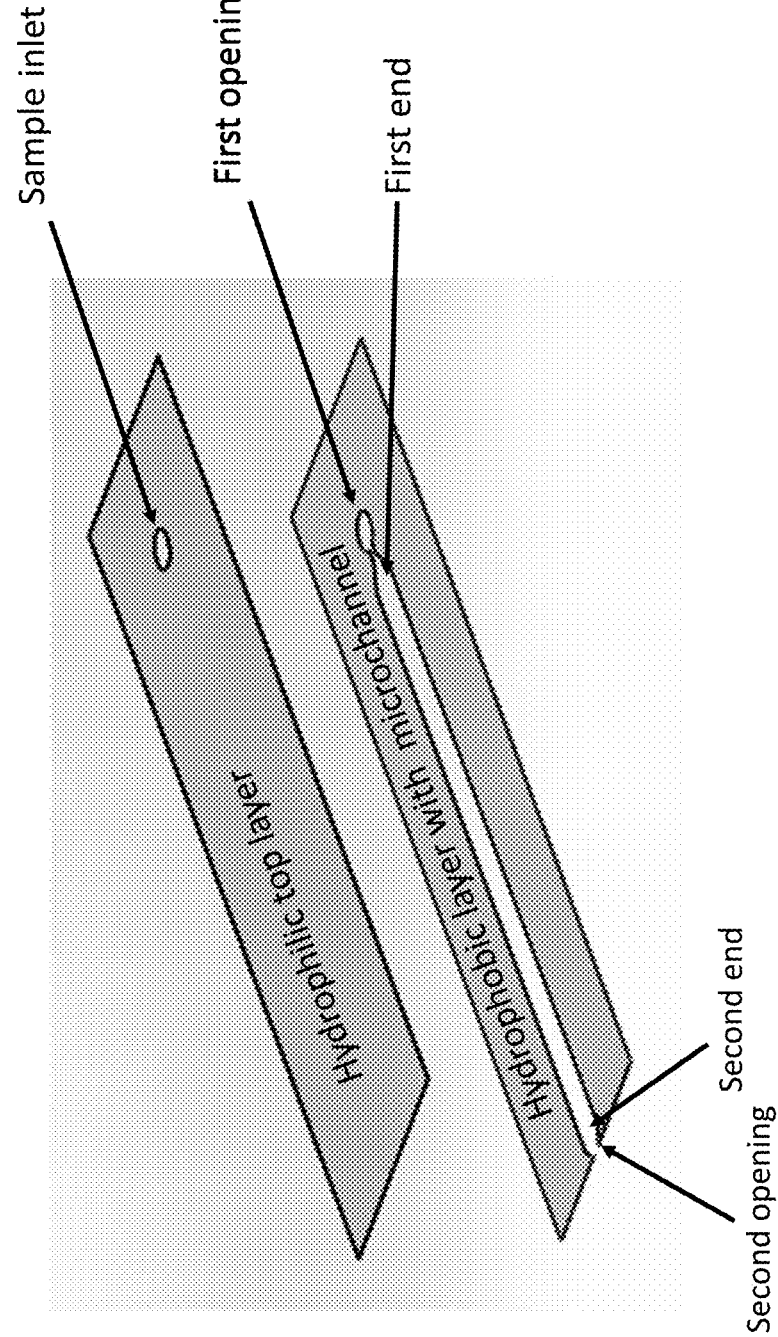
FIG. 8 shows an apparatus that can be used as a plasma separation device.

For example, FIG. 8 illustrates an apparatus for plasma separation which contains a hydrophilic top layer and a hydrophobic layer containing a microchannel having a first and second end. The top layer is adherent to the hydrophobic layer. The hydrophilic top layer comprises a sample inlet and the hydrophobic layer contains a first opening directly below the sample inlet. The first opening in the hydrophobic layer directly below the sample inlet is connected to the first end of the microchannel. When the plasma reaches the first opening on the hydrophobic layer, it flows from the opening into the first end of the microchannel and continues to flow to the second opening at the second end (e.g., opposite end) where it can be collected or allowed to flow directly on or into a sample analysis cartridge.

Figure 9:
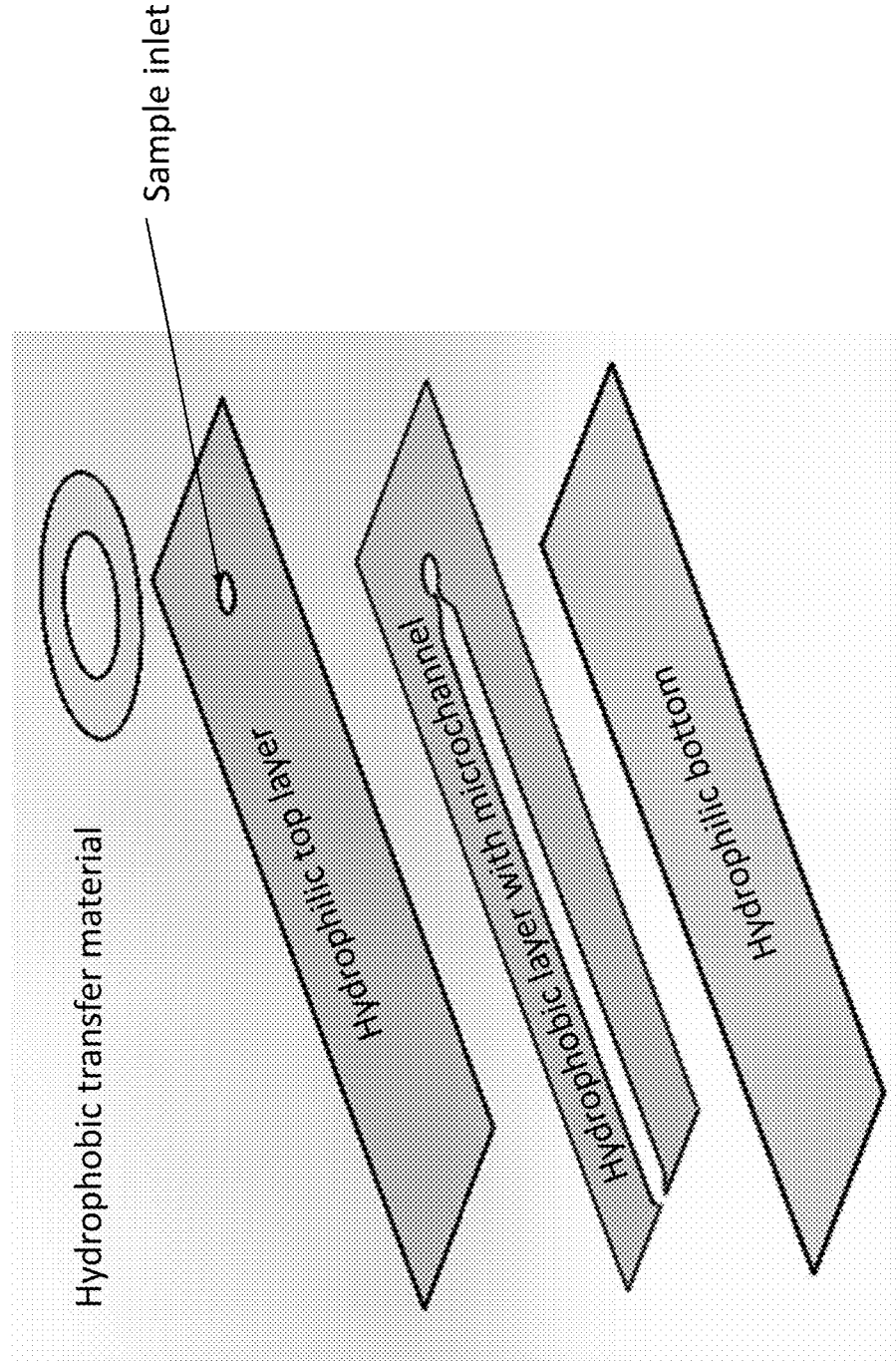
FIG. 9 shows an alternative apparatus that can be used as a plasma separation device.

FIG. 9 illustrates another embodiment of an apparatus for plasma separation. In this embodiment, the apparatus comprises a hydrophilic top layer, a hydrophobic layer and a hydrophilic bottom layer. The hydrophilic top layer is adherent to the hydrophobic layer and the bottom layer is adherent to the hydrophobic layer. The hydrophilic top layer comprises a hydrophobic transfer tape and a sample inlet. The hydrophobic layer contains a first opening directly below the sample inlet. The first opening in the hydrophobic layer directly below the sample inlet is connected to the first end of the microchannel. When the plasma reaches the first opening on the hydrophobic layer, it flows into the first end of the microchannel and continues to flow to the second opening at the second (e.g., opposite) end where it can be collected or allowed to flow directly on or into a sample analysis cartridge.

In still further aspects, the sample inlet can further comprise a separation membrane (such as a plasma separation membrane). In some aspects, the separation membrane is a glass fiber material, such as a membrane, film, fabric, fiber, filter, microfilm, screen, mesh, or any combination thereof. Additionally, the separation membrane can be in any shape. For example, the sample inlet can be round, oval, rectangular, square, triangular, or any combination thereof. In some aspects, the separation membrane can have the same shape as the sample inlet. In other aspects, the separation membrane can have a different shape than the sample inlet.

The separation membrane can be made from any material known in the art to be useful for separating blood samples or blood products into its components, such as plasma. When a blood sample or blood product is placed on a separation membrane, the blood sample or product flows through the membrane or material. As it flows through the membrane or material, cellular components of the blood (e.g., red blood cells, white blood cells, platelets, and combinations thereof) are captured in the pores and/or fibers of the membrane or material thereby allowing the plasma to continue to flow through the sample inlet and to the first opening on the hydrophobic layer. The first opening on the hydrophobic layer is connected to the microchannel such that when the plasma reaches the first opening on the hydrophobic layer, it flows into the first end of the microchannel and continues to flow to the second opening at the second (e.g., opposite end) of the microchannel. Once the plasma reaches the second opening at the second end of the microchannel, it can be collected using a collection or other device, or, if the apparatus is operably linked, removably coupled, or in fluid communication with another device (such as a sample analysis cartridge (e.g., a microfluidic cartridge), allowed to continue to flow directly on or into the device for further processing and analysis.

In some aspects, once the plasma reaches the first opening, second opening, or both the first and second opening of the microchannel, a pump, such as an air pump, foam ring pump, foil blister pump, film blister pump, or any combination thereof can be used to direct and/or disperse the plasma in the microchannel. In some aspects, the pump can be used to direct and/or disperse the plasma from the first end of the microchannel towards the second end of the microchannel. In yet other aspects, the pump can be used to direct and/or disperse the plasma from the second end of the microchannel towards and/or into another device (such as a sample analysis cartridge (e.g., a microfluidic cartridge). The pump can be connected at any point along the microfluidic channel, such as at the first opening, along the side, near the second end, or any combination thereof.

In some aspects, the separation membrane can be positioned or placed above, below or within the sample inlet. For example, in some aspects, the separation membrane can be cut to be larger than the size of the sample inlet and simply lay on top of the sample inlet. Alternatively, the separation membrane can be cut to be the same size or slightly smaller than the size of the sample inlet and be placed in the inlet. Still further, the separation membrane can be placed underneath the sample inlet and attached or adhered by any means known in the art, such as by an adhesive, glue, etc.

When the hydrophobic layer and/or bottom layer contain one or more openings, the hydrophobic layer and/or bottom layer can further contain one or more separation membranes positioned or placed above, below or within the opening in the layer. The separation membrane can be constructed from the same materials as used for the sample inlet or can be constructed from different materials. In still further aspects, the separation membrane can be positioned or placed above, below or within one or more openings. For example, in some aspects, the separation can be cut to be larger than the size of the opening and simply lay on top of the opening. Alternatively, the separation membrane can be cut to be the same size or slightly smaller than the size of the opening and be placed in the inlet. Still further, the separation membrane can be placed underneath the opening and attached or adhered by any means known in the art, such as by an adhesive, glue, etc.

In yet further aspects, one or more hydrophilic meshes or hydrophilic films can flank the separation membrane at the sample inlet and/or one or more openings. For example, a hydrophilic mesh or hydrophilic film can be positioned above or on top of the separation membrane to facilitate the spread of the blood sample or blood product into the apparatus. Alternatively, a hydrophilic mesh or hydrophilic film can be positioned below or beneath the separation membrane to help facilitate the continued movement of the blood sample or blood product as it is processed through to the hydrophobic layer and the first opening that is connected to the first end of the microchannel.

In some aspects, the apparatus further comprises an upper substrate material that comprises a sample inlet. The upper substrate material flanks or is positioned above or on top of the top layer. In some aspects, the top layer is adherent to the upper substrate. The upper substrate material can be a membrane, film, fabric, fiber, filter, microfilm, screen, mesh, or any combination thereof. In some aspects, the upper substrate material is made of a hydrophilic material. In other aspects, the upper substrate material is made from a hydrophobic material.

The upper substrate material comprises a sample inlet where the blood sample or blood product is placed to begin the sample processing. The sample inlet can have any shape. For example, the sample inlet can be round, oval, rectangular, square, triangular, or any combination thereof. In some aspects, a hydrophobic transfer material (e.g., such as a transfer tape) can surround the sample inlet. The hydrophobic transfer material helps prevent the blood sample or blood product from wicking or moving away from the sample inlet area.

In still further aspects, the sample inlet can comprise a separation. In some aspects, the separation membrane comprises a glass fiber material such as a membrane, film, fabric, fiber, filter, microfilm, screen, mesh, or any combination thereof. The separation membrane can be made from any material known in the art to be useful for separating blood samples or blood products into its components, such as plasma. The separation membrane in the upper substrate functions in the same way as the separation membrane used in the sample inlet of the top layer.

In some aspects, the separation membrane can be positioned or placed above, below or within the sample inlet. For example, in some aspects, the separation membrane can be cut to be larger than the size of the sample inlet and simply lay on top of the sample inlet. Alternatively, the separation membrane can be cut to be the same size or slightly smaller than the size of the sample inlet and be placed in the inlet. Still further, the separation membrane can be placed underneath the sample inlet and attached or adhered by any means known in the art, such as by an adhesive, glue, etc.

When an upper substrate and sample inlet are present, one or more openings are made in each of the top layer and hydrophobic layer or each of the top layer, hydrophobic layer and optionally, the bottom layer. The opening can have any shape. For example, the opening can be round, oval, rectangular, square, triangular, or any combination thereof. In some aspects, the opening is the same shape as the sample inlet. In other aspects, the opening is a different shape as the sample inlet. In some aspects, when the apparatus contains an upper substrate, one or more openings can be made in the top layer and hydrophobic layer but not in the bottom layer. In other aspects, one or more openings can be made in each of the top layer, hydrophobic layer and bottom layer. Each opening in the one or more layers can be directly below the sample inlet. One or more openings in each of the top layer, hydrophobic layer and/or bottom layer can also contain one or more separation membranes positioned or placed above, below or within the opening in the layer. The separation membrane can be constructed from the same materials as used for the sample inlet or can be constructed from different materials. Additionally, one or more hydrophilic meshes or films can flank the separation membrane at the sample inlet and/or one or more openings. For example, a hydrophilic mesh or hydrophilic film can be positioned above or below the separation membrane as described previously herein.

In still another aspect, the top layer, hydrophobic layer, bottom layer, hydrophilic mesh or hydrophilic film, separation membrane, or any combination thereof is either ubiquitous for any analyte or specific for an analyte or class of analytes.

In still another aspect, the apparatus further comprises at least one agglutinating agent to agglutinate the red blood cells to form red blood cell aggregates to improve separation and produce a cleaner plasma. In some aspects, the agglutinating agent is coated or incorporated into or on one or more of the top layer, hydrophobic layer, bottom layer, upper substrate, separation membrane, hydrophilic mesh or hydrophilic film, or any combination thereof. Examples of an agglutinating agent that can be used includes, lectin (e.g., soybean lectin), Merquat-100, Concanavalin A, DEAE-Dextran, poly-L-lysine, polyvinylpyrrolidone, poly(2-(dimethylamino)ethylmethacrylate), or any combinations thereof.

In still yet another aspect, the top layer, hydrophobic layer, bottom layer, upper substrate, separation membrane, hydrophilic mesh or hydrophilic film, or any combination thereof, is coated with a coating, such as with a surfactant, hydrophilic coating or any combination thereof, to improve or increase the speed or rate of separation of the plasma and/or serum from whole blood as it passes through any of the layers, substrates, membranes, meshes, files, or any combination thereof.

The plasma produced using the apparatus disclosed herein may not be pure plasma but rather plasma depleted of one or more components of blood (e.g., red blood cells, white blood cells, platelets, and combinations thereof). In some aspects, the plasma contains about 5% by volume or less of red blood cells, white blood cells and/or platelets. In other aspects, the plasma contains about 5% or less by volume of red blood cells. In other aspects, the plasma contains about 4% or less by volume of red blood cells. In yet other aspects, the plasma contains about 3% or less by volume of red blood cells. In yet other aspects, the plasma contains about 2% or less by volume of red blood cells. In still yet further aspects, the plasma contains about 1% or less by volume of red blood cells.

Figure 11:
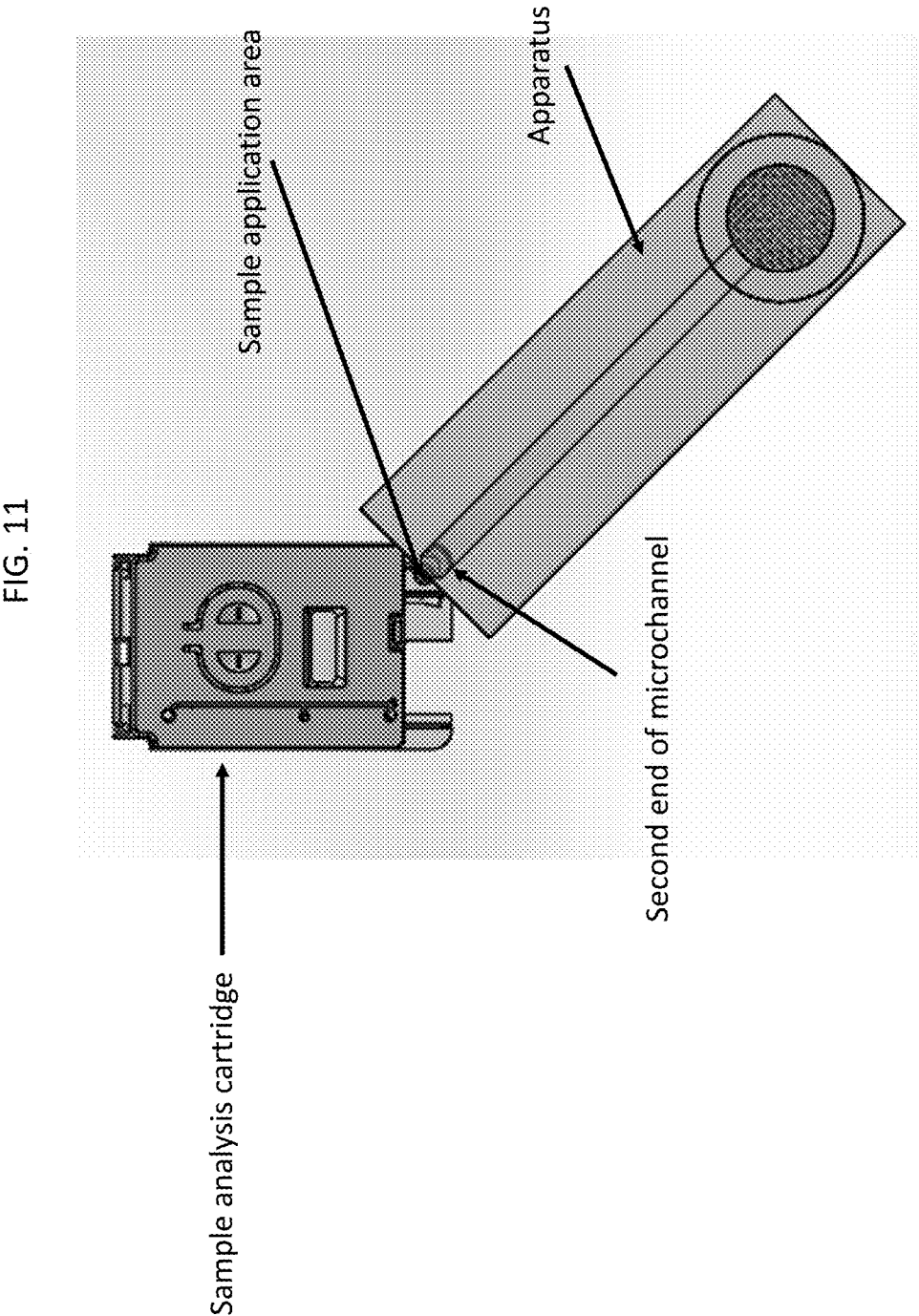
FIG. 11 shows a device comprising an apparatus that is operatively linked, removably coupled, or in fluid communication with a sample analysis cartridge. The second end of the microchannel of the apparatus is in fluid communication with a sample application area on the sample analysis cartridge.

Another aspect relates to a device. In one aspect, the device comprises the apparatus described previously herein and at least one sample analysis cartridge (e.g., a microfluidic cartridge) having a sample application area where a test sample is applied. In one aspect, the apparatus is configured with the sample analysis cartridge such that the microchannel is operably linked, removably coupled, or in fluid communication with the sample application area. Specifically, as shown in FIG. 11, the second end of the microchannel can be in operably linked, removably coupled, or in fluid communication with a sample analysis cartridge at a sample application area. In another aspect, the apparatus is included or incorporated as part of a clip, such as a moby clip, extended moby clip, etc., and configured, coupled, or integrated with the sample analysis cartridge such that the microchannel is operably linked, removably coupled, or in fluid communication with the sample application area.

In another aspect, the plasma separation apparatus comprises a pre-evacuated container or tube, having an inlet and outlet end, each of which are closed. A pressure differential exists between the inlet and outlet ends of the container or tube. The inlet end of the container or tube comprises a cap or septum which is capable of being penetrated by a needle or blood-collection needle assembly used to obtain a whole blood sample from a subject. The outlet end comprises a serum holding chamber (e.g., a filtrate container) which receives the serum and/or plasma (e.g., filtrate) produced by the apparatus.

The inlet end of the container or tube containing the cap or septum that is adapted for being pierced by a needle or standard blood-collecting needle assembly defines a first end of a blood holding chamber that is free to accept the whole blood sample from the needle or blood-collection needle assembly for filtration.

In some aspects, a filter assembly is adjacent to the second end of blood holding chamber. The filter assembly captures the cellular components of the blood (e.g., red blood cells) and allows the passage of the serum and/or plasma components through the assembly to a serum holding chamber at the outlet end. In some aspects, the filter assembly covers the entire cross-section area of the container or tube. In some aspects, the filter assembly permits the passage of particles or molecules smaller than about 0.7 microns, about 0.6 microns, about 0.5 microns, about 0.4 microns, or about 0.3 microns, and functions similar to size-exclusion chromatography (SEC, also known as gel filtration) where smaller sized particles and molecules (e.g., serum and/or plasma) pass through the filter assembly faster than larger sized molecules (e.g., red blood cells). The filter assembly can be made of any material or combination of materials that can be used to separate the components of blood based on size and allow the passage of serum and/or plasma components through the assembly and towards the serum holding chamber. For example, in some aspects, the filter assembly comprises one or more microfiber membranes and/or glass fiber filter materials (e.g., such as low-density fiber filter material). For example, Micro-Strand Glass Microfibers from Johns Manville (Fruita, CO) can be used. In some aspects, the highly hydrophilic, highly porous material such as those available from Porex Filtration Group (South Chesterfield, VA) such as, POR 410 or POR4711, can be used in the filter assembly. In yet further aspects, the filter assembly terminates and is retained and supported near the middle of the container or tube with a screen member or other perforated material.

Optionally, in some aspects, a flow regulator may be placed adjacent to the cap or septum and can be used to regulate the rate of flow of the blood to the filter assembly. In other aspects, the flow regulator can be included as part of blood-collection needle assembly.

Because the container or tube is pre-evacuated, a pressure differential exists at the area around the filter assembly. The pressure at the top of the container or tube in the blood holding chamber is higher than the pressure at the bottom of the container at the serum holding chamber. Due to this pressure differential, the whole blood sample in the blood holding chamber moves towards and through the filter assembly where the larger red blood cells are captured and entangled in the filter assembly and the serum and/or plasma (e.g., filtrate) move through the filter assembly at a much faster rate to the serum holding chamber where it is collected.

The serum holding chamber has a hollow space sized to hold the serum and/or plasma resulting from the filter assembly. The serum holding chamber is removably attached (e.g., detachable) to the container or tube and is capable of being detached from the container or tube to allow further processing and/or analysis of the serum or plasma. For example, the serum holding chamber can be detached from the container or tube by twisting or sliding the serum holding chamber in a clockwise or counter-clockwise motion to break the vacuum. Once the serum holding chamber is detached from the container or tube, the serum or plasma sample can be used for further processing and/or analysis on another device and/or apparatus. For example, the serum or plasma sample in the serum holding chamber can be pipetted into another container or device (e.g., a cartridge) for further processing and/or analysis.

In other aspects, the plasma separation can occur in a container or tube that is not pre-evacuated. In such aspects, plasma separation can be performed using any appropriate means, e.g., any means including employing size exclusion-type chromatography to separate molecules or the components in blood by differences in size as they pass through a material (e.g., filter assembly) contained within the container or tube. For instance, any material that would help preferentially slow down the movement of the red blood cells as compared to the plasma such that plasma can be retrieved could be employed (e.g., glass or porous beads, membranes, one or more filter, glass or other fiber materials, or any combination thereof). Such methods would include using other than a pressure differential, for instance, gravity-fed separation could be employed without the use of any pressure differential.

An example of pre-evacuated container or tube having the above-described components which can be used as a plasma separation apparatus in the methods described in the present disclosure include those described in U.S. Pat. No. 9,427, 707, the contents of which are herein incorporated by reference.

In yet other aspects, the above described plasma separation devices can be used in connection with a capillary blood sample which is collected (1) in a decentralized setting; (2) without the use of a syringe, standard needle, or combination thereof; (3) by a user not trained in collecting blood samples from a subject; (4) by a robot; (5) by a self- or other-administered blood collection device; or (6) any combination thereof.

In still further aspects, the above-described plasma separation devices can be used in connection with a blood sample obtained from a subject that is collected with the use of a syringe, standard needle, or combination thereof. Such a sample may be collected in a decentralized or centralized setting (e.g., in a traditional medical setting (such as a hospital, physician office, stand alone lab site, etc.), by a user trained in collecting blood or a combination thereof. In some aspects, the blood sample obtained from a subject that is collected with the use of a syringe, standard needle, or combination thereof is a venous blood sample. In other aspects, the blood sample obtained from a subject that is collected with the use of a syringe, standard needle, or combination thereof is a capillary blood sample. For example, in some aspects, a blood sample (e.g., a venous blood sample and/or a capillary blood sample) can be obtained from a subject using a syringe, standard needle, or combination thereof (and optionally, in a centralized setting and/or by a user trained in collecting blood samples from a subject) and processed prior to performing an assay for GFAP and/, using the above described plasma separation devices.

4. Microsampling Systems for Determining the Amount of GFAP Using a Capillary Blood Sample With reference to FIG. 2, a microsampling system 10 for determining the amount of GFAP is provided. The amount of GFAP can be used to aid in the diagnosis and/or evaluation of a subject that has sustained or may have sustained an injury to the head. In one aspect, the microsampling system 10 includes a microsampling device 14, a reaction vessel 22, and an instrument, such as instrument 26 (e.g., a point-of-care device). It should be noted that although the shape of the reaction vessel 22 shown in FIG. 2 is rectangular, the shape is not critical. For example, in some aspects, reaction vessel 22 may be in the shape of a tube. In further aspects, the reaction vessel 22 can be a microfluidic cartridge.

In some additional aspects, the system can further include a plasma separation device, 18 (FIG. 2). When the plasma separation device 18 is present, the microsampling device 14 collects a capillary blood sample from a subject, and the plasma separation device 18 creates a processed capillary blood sample (e.g., serum or plasma) from the capillary blood sample.

Figure 7:
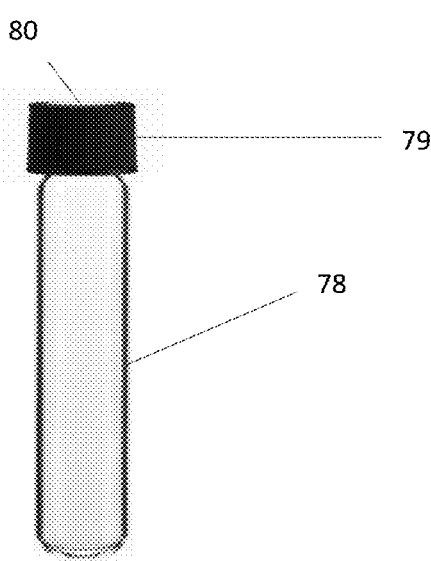
FIG. 7 shows a transfer tube for use in the system of FIG. 2.

In yet further additional aspects, the system can further include a transfer tube, 78 (FIG. 7). The transfer tube 78 can include a cap or stopper 79. The transfer tube 78 also has an aperture 80. The aperture 80 allows the reaction tube to receive a capillary blood sample or processed capillary blood sample.

In some aspects, the reaction vessel 22 or transfer tube 78 receives the processed capillary blood sample from the plasma separation device 18.

The instrument 26 analyzes the reaction vessel 22 to provide a determination of the amount of a subject's GFAP. In some aspects, the determination of the amount is communicated as a result. This result can be communicated for further analysis, interpretation, processing and/or displaying. The amount can be communicated by a computer, in a document and/or spreadsheet, on a mobile device (e.g., a smart phone), on a website, in an e-mail, or any combination thereof.

In some aspects, the communicated amount of GFAP can be displayed, such as on an instrument, such as instrument 26. For example, the amount of GFAP can be displayed as being elevated, not elevated, or that the test (e.g., assay) should be repeated). Various operating steps with the system 10 are illustrated with respect to FIGS. 3A-3E and FIG. 4A-4C are described in further detail herein.

Figures 3A, 3B, 3C, 3D, 3E:
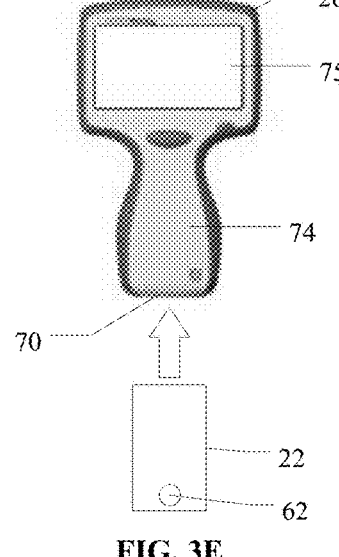
FIG. 3A-3E shows operation steps of the system of FIG. 2.

With reference to FIG. 3A, the microsampling device 14 is coupled to a subject 30 and a capillary blood sample is drawn from the subject 30. In the illustrated embodiment, the microsampling device 14 includes a housing 34 and a receptacle 38 coupled to the housing 34. In the illustrated embodiment, the capillary blood sample is collected in the receptacle 38. In other aspects, the receptacle 38 is removably coupled to the housing 34. For example, the receptacle 38 may be separated from the housing 34 once the capillary blood sample is collected. In still yet other aspects, the receptacle 38 is the reaction vessel 22. In these aspects, when the receptacle is the reaction vessel, the receptacle can be removed from the microsampling device 14 and inserted directly into instrument 26.

The microsampling device 14 further includes a microneedle, a lancet, a microlancet, a blade, a microblade, a microscrew, or any combination thereof coupled to the housing. In some aspects, the microsampling device 14 includes a plurality of microneedles. In some aspects, the microsampling device 14 further includes an actuator movable relative to the housing 34. The actuator may actuate the microneedles or similar components into a subject's skin to begin drawing a capillary blood sample from the subject 30.

With reference to FIG. 3B, the system 10 may further include a cap 42 coupled to the receptacle 38. In some embodiments, the cap 42 is attached to the receptacle 38 after the receptacle is removed from the housing 34. In aspects, the cap 42 seals the capillary blood sample within the container 38. For example, a threaded configuration may couple the cap 42 with the receptacle 38. In some embodiments, the cap 42 is part of an interface between the receptacle 38 and the plasma separation device 18.

With reference to FIG. 3C, the plasma separation device 18 includes an inlet 46 to receive the capillary blood sample from the microsampling device 14 and an outlet 50 through which the processed capillary blood sample leaves the plasma separation device 18. In the illustrated embodiment, the inlet 46 receives the capillary blood sample from the receptacle 38. In some aspects, the plasma separation device 18 is integrated within the receptacle 38 (e.g., the plasma separation device 18 is not intended to be removed from the receptacle 38 by the user).

In some other aspects, the plasma separation device 18 is separately formed from the reaction vessel 22 or transfer tube 78 (i.e., the plasma separation device 18 is movable and can be separated from the reaction vessel 22 or transfer tube 78). In other aspects, the plasma separation device 18 is integrated with the reaction vessel 22 or transfer tube 78. For example, in some aspects, the plasma separation device 18 is integrated within a housing 54 of the reaction vessel 22 (i.e., the plasma separation device 18 is not intended to be removed from the reaction vessel 22 or transfer tube 78 by a user).

The plasma separation device 18 includes a filter, a membrane, a synthetic paper, or any combinations thereof. In one aspect, the plasma separation device 18 is removably coupled to the reaction vessel 22 or transfer tube 78 with a removable coupling 58. In some aspects, the removable coupling 58 includes a threaded configuration. In other embodiments, the removable coupling 58 includes a retaining member positioned on the reaction vessel 22 or transfer tube 78 to hold the plasma separation device 18 in position once the plasma separation device 18 is installed on the reaction vessel 22 or transfer tube 78. The outlet 50 of the plasma separation device 18 is placed in fluid communication with an aperture 62 on the reaction vessel 22 or aperture 80 of the transfer tube 78. In other words, the processed capillary blood sample flows from the outlet 50 of the plasma separation device 18 into the aperture 62 of the reaction vessel 22 or aperture 80 of the transfer tube 78.

In still further aspects, the receptacle 38 is removably coupled to the plasma separation device 18 with a removable coupling 66 (FIG. 3C). In some aspects, the receptacle 38 is coupled to the plasma separation device 18 after the plasma separation device 18 is coupled to the reaction vessel 22 or transfer tube 78. In yet further aspects, the cap 42 is removed before coupling the receptacle 38 with the plasma separation device 18. In some aspects, the cap 42 remains in place as the receptacle 38 is coupled with the plasma separation device 18. In some aspects, the cap 42 is pierced as the receptacle 38 is coupled to the plasma separation device 18, permitting the capillary blood sample to flow into the plasma separation device 18.

In still further aspects, the plasma separation device 18 is removably coupled to the reaction vessel 22 or transfer tube 78 and the receptacle 38. With reference to FIG. 3D, the plasma separation device 18 is positioned between the receptacle 38 and the reaction vessel 22. In other aspects, the plasma separation device 18 is positioned between the receptacle 38 and the transfer tube 78. In some aspects, the receptacle 38 is squeezed by a user or operator to force the capillary blood sample through the plasma separation device 18 and into the reaction vessel 22 or transfer tube 78. In other aspects, the receptacle 38 includes a plunger to force the capillary blood sample through the plasma separation device 18 and into the reaction vessel 22 or transfer tube 78. In other embodiment, the capillary blood sample is gravity-fed through the plasma separation device 18 and into the reaction vessel 22 or transfer tube 78.

With reference to FIG. 3D, the reaction vessel 22 in some aspects is a microfluidic cartridge. The processed capillary blood sample flows from the plasma separation device 18 to the reaction vessel 22 in which assays are performed. In some aspects, the assay is for GFAP.

Figure 4:
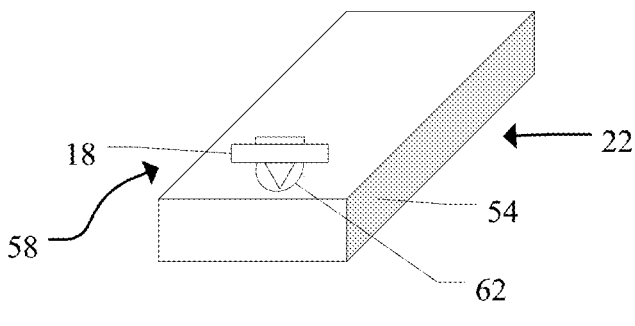
FIG. 4 shows additional and alternative aspects of the system of FIG. 2.
Figure 5:
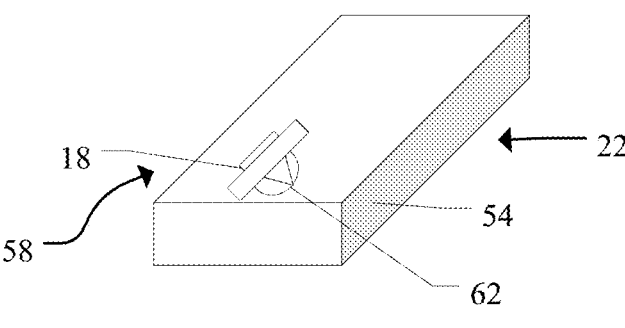
FIG. 5 shows additional and alternative aspects of the system of FIG. 2.
Figure 6:
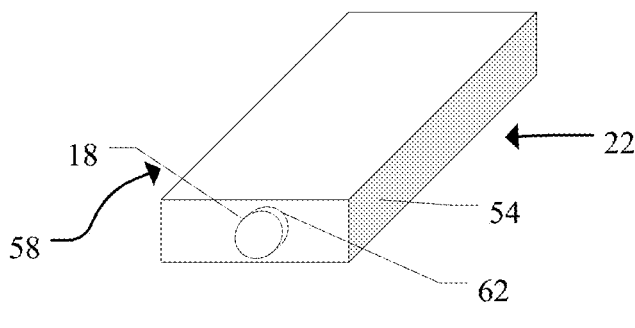
FIG. 6 shows additional and alternative aspects of the system of FIG. 2.

In still further aspects, with reference to FIG. 4, the plasma separation device 18 is placed in fluid communication with an aperture 62 at any point along the reaction vessel 22 (e.g., microfluidic cartridge). In some aspects, the plasma separation device 18 is placed in fluid communication with the aperture 62 at one end, on the side or in the middle of the reaction vessel 22 (e.g., microfluidic cartridge). In some aspects, as shown in FIG. 5, the plasma separation device 18 is placed in fluid communication with the aperture 62 (e.g., microfluidic cartridge) at an end or side of the reaction vessel 22 at an angle, such as, for example, at about 5 degrees, about 10 degrees, about 15 degrees, about 20 degrees, about 25 degrees, about 30 degrees, about 35 degrees, about 40 degrees, about 45 degrees, about 50 degrees, about 55 degrees, about 60 degrees, about 65 degrees, about 70 degrees, about 75 degrees, about 80 degrees, about 85 degrees, or at about 90 degrees (e.g., perpendicular, which forms an L or J shape). In other aspects, as shown in FIG. 6, the plasma separation device 18 is placed in fluid communication with at least one aperture 62 at one end or side of the reaction vessel 22 (e.g., microfluidic cartridge).

In one aspect, with reference to FIG. 3E, with the processed capillary blood sample loaded into the reaction vessel 22, the reaction vessel 22 is inserted into the instrument 26. In the illustrated embodiment, the reaction vessel 22 is inserted into a bottom portion 70 of a handle 74. The instrument 26 includes a display 75 configured to communicate the result of GFAP determined in the sample. For example, a display 75 on an instrument 26 may display the result as indicating that the amount of GFAP in the subject is elevated, not elevated or that the test should be repeated. In some aspects, the result is provided with visual, audio, or haptic feedback.

In some aspects, the result is communicated in about 4 minutes from the time the sample is collected (e.g., from the time of an injury or suspected injury). In some aspects, the result is communicated in about 10 minutes, about 15 minutes, about 20 minutes, about 25 minutes, about 30 minutes, about 35 minutes, or about 40 minutes from the time the sample is collected (e.g., from the time of an injury or suspected injury). In some aspects, the result is communicated within a range of about 4 minutes to about 40 minutes from the time the sample is collected (such as, for example, from the time of injury or suspected injury). In some aspects, the result is communicated within a range of about 4 minutes to about 30 minutes from the time the sample is collected (such as, for example, from the time of injury or suspected injury). In some aspects, the result is communicated within a range of about 4 minutes to about 20 minutes from the time the sample is collected (such as, for example, from the time of injury or suspected injury).

Advantageously, a portion of the system 10 is usable in a decentralized setting. In other words, the system 10 is portable. Advantageously, the system 10 or parts thereof are reusable for a plurality of samples and/or subjects. In some embodiments, the microsampling device 14, the plasma separation device 18 and the reaction vessel 22 or transfer tube 78 are single-use components (i.e., usable for a single test on a single subject); while the instrument 26 is reusable to analyze a plurality of reaction vessels 22.

5. Treatment and Monitoring of Subjects

The subject identified in the methods described above may be treated or monitored. In some embodiments, the method further includes treating the subject, such as a human subject, with an acquired brain injury or traumatic brain injury treatment, such as any treatments known in the art. For example, treatment of an acquired brain injury or traumatic brain injury can take a variety of forms depending on the severity of the injury to the head. For example, for subjects suffering from mild TBI, the treatment may include one or more of rest, abstaining from physical activities, such as sports, avoiding light or wearing sunglasses when out in the light, medication for relief of a headache or migraine, anti-nausea medication, etc. Treatment for patients suffering from moderate, severe or moderate to severe TBI might include administration of one or more appropriate medications (such as, for example, diuretics, anti-convulsant medications, medications to sedate and put an individual in a drug-induced coma, or other pharmaceutical or biopharmaceutical medications (either known or developed in the future for treatment of TBI), one or more surgical procedures (such as, for example, removal of a hematoma, repairing a skull fracture, decompressive craniectomy, etc.), protecting the airway, and one or more therapies (such as, for example one or more rehabilitation, cognitive behavioral therapy, anger management, counseling psychology, etc.). In some embodiments, the method further includes monitoring the subject, such as a human subject. In some embodiments, a subject may be monitored with CT scan or MRI procedure.

6. Methods for Measuring the Level of GFAP

In the methods described above, GFAP levels can be measured by any means, such as antibody dependent methods, such as immunoassays, protein immunoprecipitation, immunoelectrophoresis, chemical analysis, SDS-PAGE and Western blot analysis, or protein immunostaining, electrophoresis analysis, a protein assay, a competitive binding assay, a functional protein assay, or chromatography or spectrometry methods, such as high-performance liquid chromatography (HPLC) or liquid chromatography-mass spectrometry (LC/MS). Also, the assay can be employed in clinical chemistry format such as would be known by one skilled in the art.

In some embodiments, measuring the level of GFAP includes contacting the sample with a first specific binding member and second specific binding member. In some embodiments the first specific binding member is a capture antibody and the second specific binding member is a detection antibody. In some embodiments, measuring the level of GFAP includes contacting the sample, either simultaneously or sequentially, in any order: (1) a capture antibody (e.g., GFAP-capture antibody), which binds to an epitope on GFAP or GFAP fragment to form a capture antibody-GFAP antigen complex (e.g., GFAP-capture antibody-GFAP antigen complex), and (2) a detection antibody (e.g., GFAP-detection antibody), which includes a detectable label and binds to an epitope on GFAP that is not bound by the capture antibody, to form a GFAP antigen-detection antibody complex (e.g., GFAP antigen-GFAP-detection antibody complex), such that a capture antibody-GFAP antigen-detection antibody complex (e.g., GFAP-capture antibody-GFAP antigen-GFAP-detection antibody complex) is formed, and measuring the amount or concentration of GFAP in the sample based on the signal generated by the detectable label in the capture antibody-GFAP antigen-detection antibody complex.

In some embodiments, the first specific binding member is immobilized on a solid support. In some embodiments, the second specific binding member is immobilized on a solid support. In some embodiments, the first specific binding member is a GFAP antibody as described below.

In some embodiments, the sample is diluted or undiluted. The sample can be from about 1 to about 25 microliters, about 1 to about 24 microliters, about 1 to about 23 microliters, about 1 to about 22 microliters, about 1 to about 21 microliters, about 1 to about 20 microliters, about 1 to about 18 microliters, about 1 to about 17 microliters, about 1 to about 16 microliters, about 15 microliters or about 1 microliter, about 2 microliters, about 3 microliters, about 4 microliters, about 5 microliters, about 6 microliters, about 7 microliters, about 8 microliters, about 9 microliters, about 10 microliters, about 11 microliters, about 12 microliters, about 13 microliters, about 14 microliters, about 15 microliters, about 16 microliters, about 17 microliters, about 18 microliters, about 19 microliters, about 20 microliters, about 21 microliters, about 22 microliters, about 23 microliters, about 24 microliters or about 25 microliters. In some embodiments, the sample is from about 1 to about 150 microliters or less or from about 1 to about 25 microliters or less.

Some instruments (such as, for example the Abbott Laboratories instrument ARCHITECT®, and other core laboratory instruments) other than a point-of-care device may be capable of measuring levels of GFAP in a sample higher or greater than 25,000 pg/mL.

Other methods of detection include the use of or can be adapted for use on a nanopore device or nanowell device. Examples of nanopore devices are described in International Patent Publication No. WO 2016/161402, which is hereby incorporated by reference in its entirety. Examples of nanowell device are described in International Patent Publication No. WO 2016/161400, which is hereby incorporated by reference in its entirety

7. GFAP Antibodies

The methods described herein may use an isolated antibody that specifically binds to Glial fibrillary acidic protein ("GFAP") (or fragments thereof), referred to as "GFAP antibody." The GFAP antibodies can be used to assess the GFAP status as a measure of traumatic brain injury, detect the presence of GFAP in a sample, quantify the amount of GFAP present in a sample, or detect the presence of and quantify the amount of GFAP in a sample.

a. Glial Fibrillary Acidic Protein (GFAP)

Glial fibrillary acidic protein (GFAP) is a 50 kDa intra-cytoplasmic filamentous protein that constitutes a portion of the cytoskeleton in astrocytes, and it has proved to be the most specific marker for cells of astrocytic origin. GFAP protein is encoded by the GFAP gene in humans. GFAP is the principal intermediate filament of mature astrocytes. In the central rod domain of the molecule, GFAP shares considerable structural homology with the other intermediate filaments. GFAP is involved in astrocyte motility and shape by providing structural stability to astrocytic processes. Glial fibrillary acidic protein and its breakdown products (GFAP-BDP) are brain-specific proteins released into the blood as part of the pathophysiological response after traumatic brain injury (TBI). Following injury to the human CNS caused by trauma, genetic disorders, or chemicals, astrocytes proliferate and show extensive hypertrophy of the cell body and processes, and GFAP is markedly upregulated. In contrast, with increasing astrocyte malignancy, there is a progressive loss of GFAP production. GFAP can also be detected in Schwann cells, enteric glia cells, salivary gland neoplasms, metastasizing renal carcinomas, epiglottic cartilage, pituicytes, immature oligodendrocytes, papillary meningiomas, and myoepithelial cells of the breast.

Human GFAP may have the following amino acid sequence:

(SEQ ID NO: 2)
MERRRITSAARRSYVSSGEMMVGGLAPGRRLGPGTRLSLARMPPPLPTRV

DFSLAGALNAGFKETRASERAEMMELNDRFASYIEKVRFLEQQNKALAAE

LNQLRAKEPTKLADVYQAELRELRLRLDQLTANSARLEVERDNLAQDLAT

VRQKLQDETNLRLEAENNLAAYRQEADEATLARLDLERKIESLEEEIRFL

-continued
RKIHEEEVRELQEQLARQQVHVELDVAKPDLTAALKEIRTQYEAMASSNM

HEAEEWYRSKFADLTDAAARNAELLRQAKHEANDYRRQLQSLTCDLESLR

GTNESLERQMREQEERHVREAASYQEALARLEEEGQSLKDEMARHLQEYQ

DLLNVKLALDIEIATYRKLLEGEENRITIPVQTFSNLQIRETSLDTKSVS

EGHLKRNIVVKTVEMRDGEVIKESKQEHKDVM.

The human GFAP may be a fragment or variant of SEQ ID NO: 2. The fragment of GFAP may be between 5 and 400 amino acids, between 10 and 400 amino acids, between 50 and 400 amino acids, between 60 and 400 amino acids, between 65 and 400 amino acids, between 100 and 400 amino acids, between 150 and 400 amino acids, between 100 and 300 amino acids, or between 200 and 300 amino acids in length. The fragment may comprise a contiguous number of amino acids from SEQ ID NO: 2. The human GFAP fragment or variant of SEQ ID NO: 2 may be a GFAP breakdown product (BDP). The GFAP BDP may be 38 kDa, 42 kDa (fainter 41 kDa), 47 kDa (fainter 45 kDa); 25 kDa (fainter 23 kDa); 19 kDa, or 20 kDa. In some embodiments, the human GFAP fragment or variant can be a GFAP BDP comprising between 5 to 25 amino acids, between 5 to 50 amino acids, between 5 to 100 amino acids or 5 to 200 amino acids.

b. GFAP-Recognizing Antibody

The antibody is an antibody that binds to GFAP, a fragment thereof, an epitope of GFAP, or a variant thereof. The antibody may be a fragment of the anti-GFAP antibody or a variant or a derivative thereof. The antibody may be a polyclonal or monoclonal antibody. The antibody may be a chimeric antibody, a single chain antibody, an affinity matured antibody, a human antibody, a humanized antibody, a fully human antibody or an antibody fragment, such as a Fab fragment, or a mixture thereof. Antibody fragments or derivatives may comprise $F(ab')_2$, Fv or scFv fragments. The antibody derivatives can be produced by peptidomimetics. Further, techniques described for the production of single chain antibodies can be adapted to produce single chain antibodies.

The anti-GFAP antibodies may be a chimeric anti-GFAP or humanized anti-GFAP antibody. In one embodiment, both the humanized antibody and chimeric antibody are monovalent. In one embodiment, both the humanized antibody and chimeric antibody comprise a single Fab region linked to an Fc region.

Human antibodies may be derived from phage-display technology or from transgenic mice that express human immunoglobulin genes. The human antibody may be generated as a result of a human in vivo immune response and isolated. See, for example, Funaro et al., BMC Biotechnology, 2008(8):85. Therefore, the antibody may be a product of the human and not animal repertoire. Because it is of human origin, the risks of reactivity against self-antigens may be minimized. Alternatively, standard yeast display libraries and display technologies may be used to select and isolate human anti-GFAP antibodies. For example, libraries of naïve human single chain variable fragments (scFv) may be used to select human anti-GFAP antibodies. Transgenic animals may be used to express human antibodies.

Humanized antibodies may be antibody molecules from non-human species antibody that binds the desired antigen having one or more complementarity determining regions (CDRs) from the non-human species and framework regions from a human immunoglobulin molecule.

The antibody is distinguishable from known antibodies in that it possesses different biological function(s) than those known in the art.

(1) Epitope

The antibody may immunospecifically bind to GFAP (SEQ ID NO: 2), a fragment thereof, or a variant thereof. The antibody may immunospecifically recognize and bind at least three amino acids, at least four amino acids, at least five amino acids, at least six amino acids, at least seven amino acids, at least eight amino acids, at least nine amino acids, or at least ten amino acids within an epitope region. The antibody may immunospecifically recognize and bind to an epitope that has at least three contiguous amino acids, at least four contiguous amino acids, at least five contiguous amino acids, at least six contiguous amino acids, at least seven contiguous amino acids, at least eight contiguous amino acids, at least nine contiguous amino acids, or at least ten contiguous amino acids of an epitope region.

c. Antibody Preparation/Production

Antibodies may be prepared by any of a variety of techniques, including those well known to those skilled in the art. In general, antibodies can be produced by cell culture techniques, including the generation of monoclonal antibodies via conventional techniques, or via transfection of antibody genes, heavy chains, and/or light chains into suitable bacterial or mammalian cell hosts, in order to allow for the production of antibodies, wherein the antibodies may be recombinant. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies include Chinese Hamster Ovary (CHO cells) (including dhfr-CHO cells, described in Urlaub and Chasin, *Proc. Natl. Acad. Sci. USA,* 77: 4216-4220 (1980)), used with a DHFR selectable marker, e.g., as described in Kaufman and Sharp, *J. Mol. Biol.,* 159: 601-621 (1982), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure may be performed. For example, it may be desirable to transfect a host cell with DNA encoding functional fragments of either the light chain and/or the heavy chain of an antibody. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies. In addition, bifunctional antibodies may be produced in which one heavy and one light chain are an antibody (i.e., binds human GFAP) and the other heavy and light chain are specific for an antigen other than human GFAP by crosslinking an antibody to a second antibody by standard chemical crosslinking methods.

In a preferred system for recombinant expression of an antibody, or antigen-binding portion thereof, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. Still further, the method of synthesizing a recombinant antibody may be by culturing a host cell in a suitable culture medium until a recombinant antibody is synthesized. The method can further comprise isolating the recombinant antibody from the culture medium.

Methods of preparing monoclonal antibodies involve the preparation of immortal cell lines capable of producing antibodies having the desired specificity. Such cell lines may be produced from spleen cells obtained from an immunized animal. The animal may be immunized with GFAP or a fragment and/or variant thereof. The peptide used to immunize the animal may comprise amino acids encoding human Fc, for example the fragment crystallizable region or tail region of human antibody. The spleen cells may then be immortalized by, for example, fusion with a myeloma cell fusion partner. A variety of fusion techniques may be employed. For example, the spleen cells and myeloma cells may be combined with a nonionic detergent for a few minutes and then plated at low density on a selective medium that supports that growth of hybrid cells, but not myeloma cells. One such technique uses hypoxanthine, aminopterin, thymidine (HAT) selection. Another technique includes electrofusion. After a sufficient time, usually about 1 to 2 weeks, colonies of hybrids are observed. Single colonies are selected and their culture supernatants tested for binding activity against the polypeptide. Hybridomas having high reactivity and specificity may be used.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. Affinity chromatography is an example of a method that can be used in a process to purify the antibodies.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites.

The Fv fragment can be produced by preferential proteolytic cleavage of an IgM, and on rare occasions IgG or IgA immunoglobulin molecules. The Fv fragment may be derived using recombinant techniques. The Fv fragment includes a non-covalent VH:VL heterodimer including an antigen-binding site that retains much of the antigen recognition and binding capabilities of the native antibody molecule.

The antibody, antibody fragment, or derivative may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, yeast or the like, display library); e.g., as available from various commercial vendors such as Cambridge Antibody Technologies (Cambridgeshire, UK), MorphoSys (Martinsreid/Planegg, Del.), Biovation (Aberdeen, Scotland, UK) BioInvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1997) *Microbiol. Immunol.* 41:901-907; Sandhu et al. (1996) *Crit. Rev. Biotechnol.* 16:95-118; Eren et al. (1998) *Immunol.* 93:154-161) that are capable of producing a repertoire of human antibodies, as known in the art and/or as described herein. Such techniques, include, but are not limited to, ribosome display (Hanes et al. (1997) *Proc. Natl. Acad. Sci. USA,* 94:4937-4942; Hanes et al. (1998) *Proc. Natl. Acad. Sci. USA,* 95:14130-14135); single cell antibody producing technologies (e.g., selected lymphocyte antibody method ("SLAM") (U.S. Pat. No. 5,627,052, Wen et al. (1987) *J. Immunol.* 17:887-892; Babcock et al. (1996) *Proc. Natl. Acad. Sci. USA* 93:7843-7848); gel microdroplet and flow cytometry (Powell et al. (1990) *Biotechnol.* 8:333-337; One Cell Systems, (Cambridge, Mass); Gray et al. (1995) J. Imm. Meth. 182:155-163; Kenny et al. (1995) Bio/Technol. 13:787-790); B-cell selection (Steenbakkers et al. (1994) *Molec. Biol. Reports* 19:125-134 (1994)).

An affinity matured antibody may be produced by any one of a number of procedures that are known in the art. For example, see Marks et al., *BioTechnology,* 10: 779-783 (1992) describes affinity maturation by VH and VL domain shuffling. Random mutagenesis of CDR and/or framework residues is described by Barbas et al., *Proc. Nat. Acad. Sci. USA,* 91: 3809-3813 (1994); Schier et al., Gene, 169: 147-155 (1995); Yelton et al., *J. Immunol.,* 155: 1994-2004 (1995); Jackson et al., *J. Immunol.,* 154(7): 3310-3319 (1995); Hawkins et al, *J. Mol. Biol.,* 226: 889-896 (1992). Selective mutation at selective mutagenesis positions and at contact or hypermutation positions with an activity enhancing amino acid residue is described in U.S. Pat. No. 6,914, 128 B1.

Antibody variants can also be prepared using delivering a polynucleotide encoding an antibody to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

Antibody variants also can be prepared by delivering a polynucleotide to provide transgenic plants and cultured plant cells (e.g., but not limited to tobacco, maize, and duckweed) that produce such antibodies, specified portions or variants in the plant parts or in cells cultured therefrom. For example, Cramer et al. (1999) *Curr. Top. Microbiol. Immunol.* 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al., *Adv. Exp. Med. Biol.* (1999) 464:127-147 and references cited therein. Antibody variants have also been produced in large amounts from transgenic plant seeds including antibody fragments, such as single chain antibodies (scFvs), including tobacco seeds and potato tubers. See, e.g., Conrad et al. (1998) *Plant Mol. Biol.* 38:101-109 and reference cited therein. Thus, antibodies can also be produced using transgenic plants, according to known methods.

Antibody derivatives can be produced, for example, by adding exogenous sequences to modify immunogenicity or reduce, enhance or modify binding, affinity, on-rate, off-rate, avidity, specificity, half-life, or any other suitable characteristic. Generally, part or all of the non-human or human CDR sequences are maintained while the non-human sequences of the variable and constant regions are replaced with human or other amino acids.

Small antibody fragments may be diabodies having two antigen-binding sites, wherein fragments comprise a heavy chain variable domain (VH) connected to a light chain variable domain (VL) in the same polypeptide chain (VH VL). See for example, EP 404,097; WO 93/11161; and Hollinger et al., (1993) *Proc. Natl. Acad. Sci. USA* 90:6444-6448. By using a linker that is too short to allow pairing between the two domains on the same chain, the domains are forced to pair with the complementary domains of another chain and create two antigen-binding sites. See also, U.S. Pat. No. 6,632,926 to Chen et al. which is hereby incorporated by reference in its entirety and discloses antibody variants that have one or more amino acids inserted into a hypervariable region of the parent antibody and a binding affinity for a target antigen which is at least about two fold stronger than the binding affinity of the parent antibody for the antigen.

The antibody may be a linear antibody. The procedure for making a linear antibody is known in the art and described in Zapata et al. (1995) *Protein Eng.* 8(10):1057-1062. Briefly, these antibodies comprise a pair of tandem Fd segments (VH-CH1-VH-CH1) which form a pair of antigen binding regions. Linear antibodies can be bispecific or monospecific.

The antibodies may be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

It may be useful to detectably label the antibody. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 (131I), yttrium-90 (90Y), bismuth-212 (212Bi), bismuth-213 (213Bi), technetium-99m (99mTc), rhenium-186 (186Re), and rhenium-188 (188Re); antibiotics, such as doxorubicin, adriamycin, daunorubicin, methotrexate, daunomycin, neocarzinostatin, and carboplatin; bacterial, plant, and other toxins, such as diphtheria toxin, pseudomonas exotoxin A, staphylococcal enterotoxin A, abrin-A toxin, ricin A (deglycosylated ricin A and native ricin A), TGF-alpha toxin, cytotoxin from chinese cobra (Naja atra), and gelonin (a plant toxin); ribosome inactivating proteins from plants, bacteria and fungi, such as restrictocin (a ribosome inactivating protein produced by Aspergillus restrictus), saporin (a ribosome inactivating protein from Saponaria officinalis), and RNase; tyrosine kinase inhibitors; ly207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

Antibody production via the use of hybridoma technology, the selected lymphocyte antibody method (SLAM), transgenic animals, and recombinant antibody libraries is described in more detail below.

(1) Anti-GFAP Monoclonal Antibodies Using Hybridoma Technology

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, second edition, (Cold Spring Harbor Laboratory Press, Cold Spring Harbor, 1988); Hammerling, et al., In Monoclonal Antibodies and T-Cell Hybridomas, (Elsevier, N.Y., 1981). It is also noted that the term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods of generating monoclonal antibodies as well as antibodies produced by the method may comprise culturing a hybridoma cell secreting an antibody of the disclosure wherein, preferably, the hybridoma is generated by fusing splenocytes isolated from an animal, e.g., a rat or a mouse, immunized with GFAP with myeloma cells and then screening the hybridomas resulting from the fusion for hybridoma clones that secrete an antibody able to bind a polypeptide of the disclosure. Briefly, rats can be immunized with a GFAP antigen. In a preferred embodiment, the GFAP antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks; however, a single administration of the polypeptide may also be used.

After immunization of an animal with a GFAP antigen, antibodies and/or antibody-producing cells may be obtained from the animal. An anti-GFAP antibody-containing serum is obtained from the animal by bleeding or sacrificing the animal. The serum may be used as it is obtained from the animal, an immunoglobulin fraction may be obtained from the serum, or the anti-GFAP antibodies may be purified from the serum. Serum or immunoglobulins obtained in this manner are polyclonal, thus having a heterogeneous array of properties.

Once an immune response is detected, e.g., antibodies specific for the antigen GFAP are detected in the rat serum, the rat spleen is harvested and splenocytes isolated. The splenocytes are then fused by well-known techniques to any suitable myeloma cells, for example, cells from cell line SP20 available from the American Type Culture Collection (ATCC, Manassas, Va., US). Hybridomas are selected and cloned by limited dilution. The hybridoma clones are then assayed by methods known in the art for cells that secrete antibodies capable of binding GFAP. Ascites fluid, which generally contains high levels of antibodies, can be generated by immunizing rats with positive hybridoma clones.

In another embodiment, antibody-producing immortalized hybridomas may be prepared from the immunized animal. After immunization, the animal is sacrificed, and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using GFAP, or a portion thereof, or a cell expressing GFAP. In a preferred embodiment, the initial screening is performed using an enzyme-linked immunosorbent assay (ELISA) or a radioimmunoassay (RIA), preferably an ELISA. An example of ELISA screening is provided in PCT Publication No. WO 00/37504.

Anti-GFAP antibody-producing hybridomas are selected, cloned, and further screened for desirable characteristics, including robust hybridoma growth, high antibody production, and desirable antibody characteristics. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, hybridomas are rat hybridomas. In another embodiment, hybridomas are produced in a non-human, non-rat species such as mice, sheep, pigs, goats, cattle, or horses. In yet another preferred embodiment, the hybridomas are human hybridomas, in which a human non-secretory myeloma is fused with a human cell expressing an anti-GFAP antibody.

Antibody fragments that recognize specific epitopes may be generated by known techniques. For example, Fab and F(ab')$_2$ fragments of the disclosure may be produced by proteolytic cleavage of immunoglobulin molecules, using enzymes such as papain (to produce two identical Fab fragments) or pepsin (to produce an F(ab')$_2$ fragment). A F(ab')$_2$ fragment of an IgG molecule retains the two antigen-binding sites of the larger ("parent") IgG molecule, including both light chains (containing the variable light chain and constant light chain regions), the CH1 domains of the heavy chains, and a disulfide-forming hinge region of the parent IgG molecule. Accordingly, an F(ab')$_2$ fragment is still capable of crosslinking antigen molecules like the parent IgG molecule.

(2) Anti-GFAP Monoclonal Antibodies Using SLAM

In another aspect of the disclosure, recombinant antibodies are generated from single, isolated lymphocytes using a procedure referred to in the art as the selected lymphocyte antibody method (SLAM), as described in U.S. Pat. No. 5,627,052; PCT Publication No. WO 92/02551; and Babcook et al., *Proc. Natl. Acad. Sci. USA,* 93: 7843-7848 (1996). In this method, single cells secreting antibodies of interest, e.g., lymphocytes derived from any one of the immunized animals are screened using an antigen-specific hemolytic plaque assay, wherein the antigen GFAP, a subunit of GFAP, or a fragment thereof, is coupled to sheep red blood cells using a linker, such as biotin, and used to identify single cells that secrete antibodies with specificity for GFAP. Following identification of antibody-secreting cells of interest, heavy- and light-chain variable region cDNAs are rescued from the cells by reverse transcriptase-PCR (RT-PCR) and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example, by panning the transfected cells to isolate cells expressing antibodies to GFAP. The amplified immunoglobulin sequences further can be manipulated in vitro, such as by in vitro affinity maturation method. See, for example, PCT Publication No. WO 97/29131 and PCT Publication No. WO 00/56772.

(3) Anti-GFAP Monoclonal Antibodies Using Transgenic Animals

In another embodiment of the disclosure, antibodies are produced by immunizing a non-human animal comprising some, or all, of the human immunoglobulin locus with a GFAP antigen. In an embodiment, the non-human animal is a XENOMOUSE® transgenic mouse, an engineered mouse strain that comprises large fragments of the human immunoglobulin loci and is deficient in mouse antibody production. See, e.g., Green et al., *Nature Genetics,* 7: 13-21 (1994) and U.S. Pat. Nos. 5,916,771; 5,939,598; 5,985,615; 5,998, 209; 6,075,181; 6,091,001; 6,114,598; and 6,130,364. See also PCT Publication Nos. WO 91/10741; WO 94/02602; WO 96/34096; WO 96/33735; WO 98/16654; WO 98/24893; WO 98/50433; WO 99/45031; WO 99/53049; WO 00/09560; and WO 00/37504. The XENOMOUSE® transgenic mouse produces an adult-like human repertoire of fully human antibodies, and generates antigen-specific human monoclonal antibodies. The XENOMOUSE® transgenic mouse contains approximately 80% of the human antibody repertoire through introduction of megabase sized, germline configuration YAC fragments of the human heavy chain loci and x light chain loci. See Mendez et al., *Nature Genetics,* 15: 146-156 (1997), Green and Jakobovits, *J. Exp. Med.,* 188: 483-495 (1998), the disclosures of which are hereby incorporated by reference.

(4) Anti-GFAP Monoclonal Antibodies Using Recombinant Antibody Libraries

In vitro methods also can be used to make the antibodies of the disclosure, wherein an antibody library is screened to identify an antibody having the desired GFAP-binding specificity. Methods for such screening of recombinant antibody libraries are well known in the art and include methods described in, for example, U.S. Pat. No. 5,223,409 (Ladner et al.); PCT Publication No. WO 92/18619 (Kang et al.); PCT Publication No. WO 91/17271 (Dower et al.); PCT Publication No. WO 92/20791 (Winter et al.); PCT Publication No. WO 92/15679 (Markland et al.); PCT Publication No. WO 93/01288 (Breitling et al.); PCT Publication No. WO 92/01047 (McCafferty et al.); PCT Publication No. WO 92/09690 (Garrard et al.); Fuchs et al., *Bio/Technology,* 9: 1369-1372 (1991); Hay et al., *Hum. Antibod. Hybridomas,* 3: 81-85 (1992); Huse et al., *Science,* 246: 1275-1281 (1989); McCafferty et al., *Nature,* 348: 552-554 (1990); Griffiths et al., *EMBO J.,* 12: 725-734 (1993); Hawkins et al., *J. Mol. Biol.,* 226: 889-896 (1992); Clackson et al., *Nature,* 352: 624-628 (1991); Gram et al., *Proc. Natl. Acad. Sci. USA,* 89: 3576-3580 (1992); Garrard et al., *Bio/Technology,* 9: 1373-1377 (1991); Hoogenboom et al., *Nucl. Acids Res.,* 19: 4133-4137 (1991); Barbas et al., *Proc. Natl. Acad. Sci. USA,* 88: 7978-7982 (1991); U.S. Patent Application Publication No. 2003/0186374; and PCT Publication No. WO 97/29131, the contents of each of which are incorporated herein by reference.

The recombinant antibody library may be from a subject immunized with GFAP, or a portion of GFAP. Alternatively, the recombinant antibody library may be from a naive subject, i.e., one who has not been immunized with GFAP, such as a human antibody library from a human subject who has not been immunized with human GFAP. Antibodies of the disclosure are selected by screening the recombinant antibody library with the peptide comprising human GFAP to thereby select those antibodies that recognize GFAP. Methods for conducting such screening and selection are well known in the art, such as described in the references in the preceding paragraph. To select antibodies of the disclosure having particular binding affinities for GFAP, such as those that dissociate from human GFAP with a particular $K_{off}$ rate constant, the art-known method of surface plasmon resonance can be used to select antibodies having the desired $K_{off}$ rate constant. To select antibodies of the disclosure having a particular neutralizing activity for GFAP, such as those with a particular $IC_{50}$, standard methods known in the art for assessing the inhibition of GFAP activity may be used.

In one aspect, the disclosure pertains to an isolated antibody, or an antigen-binding portion thereof, that binds human GFAP. Preferably, the antibody is a neutralizing antibody. In various embodiments, the antibody is a recombinant antibody or a monoclonal antibody.

For example, antibodies can also be generated using various phage display methods known in the art. In phage display methods, functional antibody domains are displayed on the surface of phage particles which carry the polynucleotide sequences encoding them. Such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv, or disulfide stabilized Fv antibody domains recombinantly fused to either the phage gene III or gene VIII protein. Examples of phage display methods that can be used to make the antibodies include those disclosed in Brinkmann et al., *J. Immunol. Methods,* 182: 41-50 (1995); Ames et al., J. Immunol. Methods, 184:177-186 (1995); Kettleborough et al., *Eur. J. Immunol.,* 24: 952-958 (1994); Persic et al., *Gene,* 187: 9-18 (1997); Burton et al., Advances in *Immunology,* 57: 191-280 (1994); PCT Publication No. WO 92/01047; PCT Publication Nos. WO 90/02809, WO 91/10737, WO 92/01047, WO 92/18619, WO 93/11236, WO 95/15982, WO 95/20401, and U.S. Pat. Nos. 5,698,426, 5,223,40, 5,403,484, 5,580,717, 5,427,908, 5,750,753, 5,821,047, 5,571,698, 5,427,908, 5,516,637, 5,780,225, 5,658,727, 5,733,743, and 5,969,108.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab', and F(ab')$_2$ fragments can also be employed using methods known in the art such as those disclosed in PCT publication No. WO 92/22324; Mullinax et al., *BioTechniques,* 12(6): 864-869 (1992); Sawai et al., *Am. J. Reprod. Immunol.,* 34: 26-34 (1995); and Better et al., *Science,* 240: 1041-1043 (1988). Examples of techniques which can be used to produce single-chain Fvs and antibodies include those described in U.S. Pat. Nos. 4,946,778 and 5,258,498; Huston et al., Methods in Enzymology, 203: 46-88 (1991); Shu et al., *Proc. Natl. Acad. Sci. USA,* 90: 7995-7999 (1993); and Skerra et al., *Science,* 240: 1038-1041 (1988).

Alternative to screening of recombinant antibody libraries by phage display, other methodologies known in the art for screening large combinatorial libraries can be applied to the identification of antibodies of the disclosure. One type of alternative expression system is one in which the recombinant antibody library is expressed as RNA-protein fusions, as described in PCT Publication No. WO 98/31700 (Szostak and Roberts), and in Roberts and Szostak, *Proc. Natl. Acad. Sci. USA,* 94: 12297-12302 (1997). In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above. A preferred example of this methodology is PROfusion display technology.

In another approach, the antibodies can also be generated using yeast display methods known in the art. In yeast display methods, genetic methods are used to tether antibody domains to the yeast cell wall and display them on the surface of yeast. Such yeast can be utilized to display antigen-binding domains expressed from a repertoire or combinatorial antibody library (e.g., human or murine). Examples of yeast display methods that can be used to make the antibodies include those disclosed in U.S. Pat. No. 6,699,658 (Wittrup et al.) incorporated herein by reference.

d. Production of Recombinant GFAP Antibodies

Antibodies may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection, and the like. Although it is possible to express the antibodies of the disclosure in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies of the disclosure include Chinese Hamster Ovary (CHO cells) (including dhfr-CHO cells, described in Urlaub and Chasin, *Proc. Natl. Acad. Sci. USA,* 77: 4216-4220 (1980), used with a DHFR selectable marker, e.g., as described in Kaufman and Sharp, *J. Mol. Biol.,* 159: 601-621 (1982), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure may be performed. For example, it may be desirable to transfect a host cell with DNA encoding functional fragments of either the light chain and/or the heavy chain of an antibody of this disclosure. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the disclosure. In addition, bifunctional antibodies may be produced in which one heavy and one light chain are an antibody of the disclosure (i.e., binds human GFAP) and the other heavy and light chain are specific for an antigen other than human GFAP by crosslinking an antibody of the disclosure to a second antibody by standard chemical crosslinking methods.

In a preferred system for recombinant expression of an antibody, or antigen-binding portion thereof, of the disclosure, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. Still further, the disclosure provides a method of synthesizing a recombinant antibody of the disclosure by culturing a host cell of the disclosure in a suitable culture medium until a recombinant antibody of the disclosure is synthesized. The method can further comprise isolating the recombinant antibody from the culture medium.

(1) Humanized Antibody

The humanized antibody may be an antibody or a variant, derivative, analog or portion thereof which immunospecifically binds to an antigen of interest and which comprises a framework (FR) region having substantially the amino acid sequence of a human antibody and a complementary determining region (CDR) having substantially the amino acid sequence of a non-human antibody. The humanized antibody may be from a non-human species antibody that binds the desired antigen having one or more complementarity determining regions (CDRs) from the non-human species and framework regions from a human immunoglobulin molecule.

As used herein, the term "substantially" in the context of a CDR refers to a CDR having an amino acid sequence at least 90%, at least 95%, at least 98% or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. According to one aspect, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or of a heavy chain.

The humanized antibody can be selected from any class of immunoglobulins, including IgM, IgG, IgD, IgA and IgE, and any isotype, including without limitation IgG1, IgG2, IgG3, and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In one embodiment, such mutations, however, will not be extensive. Usually, at least 90%, at least 95%, at least 98%, or at least 99% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, *From Genes to Clones* (Verlagsgesellschaft, Weinheim, Germany 1987)). In a family of immunoglobulins, each position in the consensus sequence is occupied by the amino acid occurring most frequently at that position in the family. If two amino acids occur equally frequently, either can be included in the consensus sequence.

The humanized antibody may be designed to minimize unwanted immunological response toward rodent anti-human antibodies, which limits the duration and effectiveness of therapeutic applications of those moieties in human recipients. The humanized antibody may have one or more amino acid residues introduced into it from a source that is non-human. These non-human residues are often referred to as "import" residues, which are typically taken from a variable domain. Humanization may be performed by substituting hypervariable region sequences for the corresponding sequences of a human antibody. Accordingly, such "humanized" antibodies are chimeric antibodies wherein substantially less than an intact human variable domain has been substituted by the corresponding sequence from a non-human species. For example, see U.S. Pat. No. 4,816,567, the contents of which are herein incorporated by reference. The humanized antibody may be a human antibody in which some hypervariable region residues, and possibly some FR residues are substituted by residues from analogous sites in rodent antibodies. Humanization or engineering of antibodies of the present disclosure can be performed using any known method, such as but not limited to those described in U.S. Pat. Nos. 5,723,323, 5,976,862, 5,824,514, 5,817,483; 5,814,476, 5,763,192, 5,723,323, 5,766,886, 5,714,352, 6,204,023, 6,180,370, 5,693,762, 5,530,101, 5,585,089, 5,225,539, and 4,816,567.

The humanized antibody may retain high affinity for GFAP and other favorable biological properties. The humanized antibody may be prepared by a process of analysis of the parental sequences and various conceptual humanized products using three-dimensional models of the parental and humanized sequences. Three-dimensional immunoglobulin models are commonly available. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristics, such as increased affinity for GFAP, is achieved. In general, the hypervariable region residues may be directly and most substantially involved in influencing antigen binding.

As an alternative to humanization, human antibodies (also referred to herein as "fully human antibodies") can be generated. For example, it is possible to isolate human antibodies from libraries via PROfusion and/or yeast related technologies. It is also possible to produce transgenic animals (e.g. mice that are capable, upon immunization, of producing a full repertoire of human antibodies in the absence of endogenous immunoglobulin production. For example, the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. The humanized or fully human antibodies may be prepared according to the methods described in U.S. Pat. Nos. 5,770,429, 5,833,985, 5,837,243, 5,922,845, 6,017,517, 6,096,311, 6,111,166, 6,270,765, 6,303,755, 6,365,116, 6,410,690, 6,682,928, and 6,984,720, the contents each of which are herein incorporated by reference.

e. Anti-GFAP Antibodies

Anti-GFAP antibodies may be generated using the techniques described above as well as using routine techniques known in the art. In some embodiments, the anti-GFAP antibody may be an unconjugated GFAP antibody, such as GFAP antibodies available from Dako (Catalog Number: M0761), ThermoFisher Scientific (Catalog Numbers: MA5-12023, A-21282, 13-0300, MA1-19170, MA1-19395, MA5-15086, MA5-16367, MA1-35377, MA1-06701, or MA1-20035), AbCam (Catalog Numbers: ab10062, ab4648, ab68428, ab33922, ab207165, ab190288, ab115898, or ab21837), EMD Millipore (Catalog Numbers: FCMAB257P, MAB360, MAB3402, 04-1031, 04-1062, MAB5628), Santa Cruz (Catalog Numbers: sc-166481, sc-166458, sc-58766, sc-56395, sc-51908, sc-135921, sc-71143, sc-65343, or sc-33673), Sigma-Aldrich (Catalog Numbers: G3893 or G6171) or Sino Biological Inc. (Catalog Number: 100140-R012-50). The anti-GFAP antibody may be conjugated to a fluorophore, such as conjugated GFAP antibodies available from ThermoFisher Scientific (Catalog Numbers: A-21295 or A-21294), EMD Millipore (Catalog Numbers: MAB3402X, MAB3402B, MAB3402B, or MAB3402(C3) or AbCam (Catalog Numbers: ab49874 or ab194325).

Alternatively, the antibodies described in WO 2018/067474, WO2018/081649, U.S. Pat. No. 11,078,298, U.S. Patent Publication No. 2019/0502127, and/or Bazarian et al., "Accuracy of a rapid GFAP/UCH-L1 test for the prediction of intracranial injuries on head CT after mild traumatic brain injury", *Acad. Emerg. Med.*, (Aug. 6, 2021), the contents of which are herein incorporated by reference, can also be used.

8. Methods for Measuring the Level of Analytes Other than GFAP (e.g., UCH-L1)

In the methods described above, the magnetic point-of-care assays for GFAP can be combined with other (i.e., non-magnetic point-of-care assays) for other analytes, e.g., including UCH-L1. UCH-L1 levels can be measured by any means, such as antibody dependent methods, such as immunoassays, protein immunoprecipitation, immunoelectrophoresis, chemical analysis, SDS-PAGE and Western blot analysis, protein immunostaining, electrophoresis analysis, a protein assay, a competitive binding assay, a functional protein assay, or chromatography or spectrometry methods, such as high-performance liquid chromatography (HPLC) or liquid chromatography-mass spectrometry (LC/MS). Also, the assay can be employed in clinical chemistry format such as would be known by one skilled in the art. For example, such methods for measuring UCH-L1 are described for example, in U.S. Pat. Nos. 10,877,038, 10,877,048, 10,849, 548, 11,016,105 and 11,022,617, the contents of which are herein incorporated by reference.

In some embodiments, measuring the level of UCH-L1 includes contacting the sample with a first specific binding member and second specific binding member. In some embodiments the first specific binding member is a capture antibody and the second specific binding member is a detection antibody. In some embodiments, measuring the level of UCH-L1 includes contacting the sample, either simultaneously or sequentially, in any order: (1) a capture antibody (e.g., UCH-L1-capture antibody), which binds to an epitope on UCH-L1 or UCH-L1 fragment to form a capture antibody-UCH-L1 antigen complex (e.g., UCH-L1-capture antibody-UCH-L1 antigen complex), and (2) a detection antibody (e.g., UCH-L1-detection antibody), which includes a detectable label and binds to an epitope on UCH-L1 that is not bound by the capture antibody, to form a UCH-L1 antigen-detection antibody complex (e.g., UCH-L1 antigen-UCH-L1-detection antibody complex), such that a capture antibody-UCH-L1 antigen-detection antibody complex (e.g., UCH-L1-capture antibody-UCH-L1 antigen-UCH-L1-detection antibody complex) is formed, and measuring the amount or concentration of UCH-L1 in the sample based on the signal generated by the detectable label in the capture antibody-UCH-L1 antigen-detection antibody complex.

In some embodiments, the first specific binding member is immobilized on a solid support. In some embodiments, the second specific binding member is immobilized on a solid support. In some embodiments, the first specific binding member is a UCH-L1 antibody as described below.

In some embodiments, the sample is diluted or undiluted. The sample can be from about 1 to about 25 microliters, about 1 to about 24 microliters, about 1 to about 23 microliters, about 1 to about 22 microliters, about 1 to about 21 microliters, about 1 to about 20 microliters, about 1 to about 18 microliters, about 1 to about 17 microliters, about 1 to about 16 microliters, about 15 microliters or about 1 microliter, about 2 microliters, about 3 microliters, about 4 microliters, about 5 microliters, about 6 microliters, about 7 microliters, about 8 microliters, about 9 microliters, about 10 microliters, about 11 microliters, about 12 microliters, about 13 microliters, about 14 microliters, about 15 microliters, about 16 microliters, about 17 microliters, about 18 microliters, about 19 microliters, about 20 microliters, about 21 microliters, about 22 microliters, about 23 microliters, about 24 microliters or about 25 microliters. In some embodiments, the sample is from about 1 to about 150 microliters or less or from about 1 to about 25 microliters or less.

9. UCH-L1 Antibodies

The methods described herein may use an isolated antibody that specifically binds to ubiquitin carboxy-terminal hydrolase L1 ("UCH-L1") (or fragments thereof), referred to as "UCH-L1 antibody." The UCH-L1 antibodies can be used to assess the UCH-L1 status as a measure of traumatic brain injury, detect the presence of UCH-L1 in a sample, quantify the amount of UCH-L1 present in a sample, or detect the presence of and quantify the amount of UCH-L1 in a sample.

a. Ubiquitin Carboxy-Terminal Hydrolase L1 (UCH-L1)

Ubiquitin carboxy-terminal hydrolase L1 ("UCH-L1"), which is also known as "ubiquitin C-terminal hydrolase," is a deubiquitinating enzyme. UCH-L1 is a member of a gene family whose products hydrolyze small C-terminal adducts of ubiquitin to generate the ubiquitin monomer. Expression of UCH-L1 is highly specific to neurons and to cells of the diffuse neuroendocrine system and their tumors. It is abundantly present in all neurons (accounts for 1-2% of total brain protein), expressed specifically in neurons and testis/ovary. The catalytic triad of UCH-L1 contains a cysteine at position 90, an aspartate at position 176, and a histidine at position 161 that are responsible for its hydrolase activity.

Human UCH-L1 may have the following amino acid sequence:

(SEQ ID NO: 1)
MQLKPMEINPEMLNKVLSRLGVAGQWRFVDVLGLEEESLGSVPAPACALL

LLFPLTAQHENFRKKQIEELKGQEVSPKVYFMKQTIGNSCGTIGLIHAVA

NNQDKLGFEDGSVLKQFLSETEKMSPEDRAKCFEKNEAIQAAHDAVAQEG

QCRVDDKVNFHFILFNNVDGHLYELDGRMPFPVNHGASSEDTLLKDAAKV

CREFTEREQGEVRFSAVALCKAA.

The human UCH-L1 may be a fragment or variant of SEQ ID NO: 1. The fragment of UCH-L1 may be between 5 and 225 amino acids, between 10 and 225 amino acids, between 50 and 225 amino acids, between 60 and 225 amino acids, between 65 and 225 amino acids, between 100 and 225 amino acids, between 150 and 225 amino acids, between 100 and 175 amino acids, or between 175 and 225 amino acids in length. The fragment may comprise a contiguous number of amino acids from SEQ ID NO: 1.

b. UCH-L1-Recognizing Antibody

The antibody is an antibody that binds to UCH-L1, a fragment thereof, an epitope of UCH-L1, or a variant thereof. The antibody may be a fragment of the anti-UCH-L1 antibody or a variant or a derivative thereof. The antibody may be a polyclonal or monoclonal antibody. The antibody may be a chimeric antibody, a single chain antibody, an affinity matured antibody, a human antibody, a humanized antibody, a fully human antibody or an antibody fragment, such as a Fab fragment, or a mixture thereof. Antibody fragments or derivatives may comprise F(ab')$_2$, Fv or scFv fragments. The antibody derivatives can be produced by peptidomimetics. Further, techniques described for the production of single chain antibodies can be adapted to produce single chain antibodies.

The anti-UCH-L1 antibodies may be a chimeric anti-UCH-L1 or humanized anti-UCH-L1 antibody. In one embodiment, both the humanized antibody and chimeric antibody are monovalent. In one embodiment, both the humanized antibody and chimeric antibody comprise a single Fab region linked to an Fc region.

Human antibodies may be derived from phage-display technology or from transgenic mice that express human immunoglobulin genes. The human antibody may be generated as a result of a human in vivo immune response and isolated. See, for example, Funaro et al., *BMC Biotechnology*, 2008(8):85. Therefore, the antibody may be a product of the human and not animal repertoire. Because it is of human origin, the risks of reactivity against self-antigens may be minimized. Alternatively, standard yeast display libraries and display technologies may be used to select and isolate human anti-UCH-L1 antibodies. For example, libraries of naïve human single chain variable fragments (scFv) may be used to select human anti-UCH-L1 antibodies. Transgenic animals may be used to express human antibodies.

Humanized antibodies may be antibody molecules from non-human species antibody that binds the desired antigen having one or more complementarity determining regions (CDRs) from the non-human species and framework regions from a human immunoglobulin molecule.

The antibody is distinguishable from known antibodies in that it possesses different biological function(s) than those known in the art.

(1) Epitope

The antibody may immunospecifically bind to UCH-L1 (SEQ ID NO: 1), a fragment thereof, or a variant thereof. The antibody may immunospecifically recognize and bind at least three amino acids, at least four amino acids, at least five amino acids, at least six amino acids, at least seven amino acids, at least eight amino acids, at least nine amino acids, or at least ten amino acids within an epitope region. The antibody may immunospecifically recognize and bind to an epitope that has at least three contiguous amino acids, at least four contiguous amino acids, at least five contiguous amino acids, at least six contiguous amino acids, at least seven contiguous amino acids, at least eight contiguous amino acids, at least nine contiguous amino acids, or at least ten contiguous amino acids of an epitope region.

c. Antibody Preparation and Production and Anti-UCH-L1 Antibodies

Anti-UCH-L1 antibodies may be generated or prepared using routine techniques and methods known in the art, such as those described in U.S. Pat. Nos. 10,877,038, 10,877,048, 10,849,548, 11,016,105 and 11,022,617, the contents of each of which are herein incorporated by reference In some embodiments, the anti-UCH-L1 antibody may be an unconjugated UCH-L1 antibody, such as UCH-L1 antibodies available from United State Biological (Catalog Number: 031320), Cell Signaling Technology (Catalog Number: 3524), Sigma-Aldrich (Catalog Number: HPA005993), Santa Cruz Biotechnology, Inc. (Catalog Numbers: sc-58593 or sc-58594), R&D Systems (Catalog Number: MAB6007), Novus Biologicals (Catalog Number: NB600-1160), Biorbyt (Catalog Number: orb33715), Enzo Life Sciences, Inc. (Catalog Number: ADI-905-520-1), Bio-Rad (Catalog Number: VMA00004), BioVision (Catalog Number: 6130-50), Abcam (Catalog Numbers: ab75275 or ab104938), Invitrogen Antibodies (Catalog Numbers: 480012), ThermoFisher Scientific (Catalog Numbers: MA1-46079, MA5-17235, MA1-90008, or MA1-83428), EMD Millipore (Catalog Number: MABN48), or Sino Biological Inc. (Catalog Number: 50690-R011). The anti-UCH-L1 antibody may be conjugated to a fluorophore, such as conjugated UCH-L1 antibodies available from BioVision (Catalog Number: 6960-25) or Aviva Systems Biology (Cat. Nos. OAAF01904-FITC).

10. Other Factors

The methods of diagnosing, prognosticating, and/or assessing, as described above, can further include using other factors for the diagnosis, prognostication, and assessment. In some embodiments, traumatic brain injury may be diagnosed using the Glasgow Coma Scale. Other tests, scales or indices can also be used either alone or in combination with the Glasgow Coma Scale. An example is the Ranchos Los Amigos Scale. The Ranchos Los Amigos Scale measures the levels of awareness, cognition, behavior and interaction with the environment. The Ranchos Los Amigos Scale includes: Level I: No Response; Level II: Generalized Response; Level III: Localized Response; Level IV: Confused-agitated; Level V: Confused-inappropriate; Level VI: Confused-appropriate; Level VII: Automatic-appropriate; and Level VIII: Purposeful-appropriate. Another example is the Rivermead Post-Concussion Symptoms Questionairre, a self-report scale to measure the severity of post-concussive symptoms following TBI. Patients are asked to rate how severe each of 16 symptoms (e.g., headache, dizziness, nausea, vomiting) has been over the past 24 hours. In each case, the symptom is compared with how severe it was before the injury occurred (premorbid). These symptoms are reported by severity on a scale from 0 to 4: not experienced, no more of a problem, mild problem, moderate problem, and severe problem.

11. Samples

In some embodiments, the sample is obtained after the subject, such as a human subject, sustained an injury to the head caused by physical shaking, blunt impact by an external mechanical or other force that results in a closed or open head trauma, one or more falls, explosions or blasts or other types of blunt force trauma. In some embodiments, the sample is obtained after the subject, such as a human subject, has ingested or been exposed to a fire, chemical, toxin or combination of a fire, chemical and toxin. Examples of such chemicals and/or toxins include, molds, asbestos, pesticides and insecticides, organic solvents, paints, glues, gases (such as carbon monoxide, hydrogen sulfide, and cyanide), organic metals (such as methyl mercury, tetraethyl lead and organic tin) and/or one or more drugs of abuse. In some embodiments, the sample is obtained from a subject, such as a human subject, that suffers from an autoimmune disease, a metabolic disorder, a brain tumor, hypoxia, a viral infection (e.g., SARS-CoV-2), a fungal infection, a bacterial infection, meningitis, hydrocephalus, or any combinations thereof.

In yet another embodiment, the methods described herein use samples that also can be used to determine whether or not a subject has or is at risk of developing a TBI (such as a mild TBI, moderate TBI, severe TBI, or moderate to severe TBI) by determining the levels of UCH-L1 and/or GFAP in a subject using the anti-UCH-L1 and/or anti-GFAP antibodies described below, or antibody fragments thereof. Thus, in particular embodiments, the disclosure also provides a method for determining whether a subject having, or at risk for, traumatic brain injuries, discussed herein and known in the art, is a candidate for therapy or treatment. Generally, the subject is at least one who: (i) has experienced an injury to the head; (ii) ingested and/or been exposed to one or more chemicals and/or toxins; (iii) suffers from an autoimmune disease, a metabolic disorder, a brain tumor, hypoxia, a viral infection (e.g., SARS-CoV-2), a fungal infection, a bacterial infection, meningitis, hydrocephalus, or any combinations thereof; or (iv) any combinations of (i)-(iii); or, who has actually been diagnosed as having, or being at risk for TBI (such as, for example, subjects suffering from an autoimmune disease, a metabolic disorder, a brain tumor, hypoxia, a viral infection (e.g., SARS-CoV-2), a fungal infection, a bacterial infection, meningitis, hydrocephalus, or any combinations thereof), and/or who demonstrates an unfavorable (i.e., clinically undesirable) concentration or amount of UCH-L1 and/or GFAP or UCH-L1 and/or GFAP fragment, as described herein.

a. Controls

It may be desirable to include a control sample. The control sample may be analyzed concurrently with the sample from the subject as described above. The results obtained from the subject sample can be compared to the results obtained from the control sample. Standard curves may be provided, with which assay results for the sample may be compared. Such standard curves present levels of marker as a function of assay units, i.e., fluorescent signal intensity, if a fluorescent label is used. Using samples taken from multiple donors, standard curves can be provided for reference levels of GFAP in normal healthy tissue, as well as for "at-risk" levels of the GFAP in tissue taken from donors, who may have one or more of the characteristics set forth above.

Thus, in view of the above, a method for determining the presence, amount, or concentration of GFAP in a test sample is provided. The method comprises assaying the test sample for GFAP by an immunoassay, for example, employing at least one capture antibody that binds to an epitope on GFAP and at least one detection antibody that binds to an epitope on GFAP which is different from the epitope for the capture antibody and optionally includes a detectable label, and comprising comparing a signal generated by the detectable label as a direct or indirect indication of the presence, amount or concentration of GFAP in the test sample to a signal generated as a direct or indirect indication of the presence, amount or concentration of GFAP in a calibrator. The calibrator is optionally, and is preferably, part of a series of calibrators in which each of the calibrators differs from the other calibrators in the series by the concentration of GFAP.

The present disclosure has multiple aspects, illustrated by the following non-limiting examples.

EXAMPLES

Example 1

Figure 1:
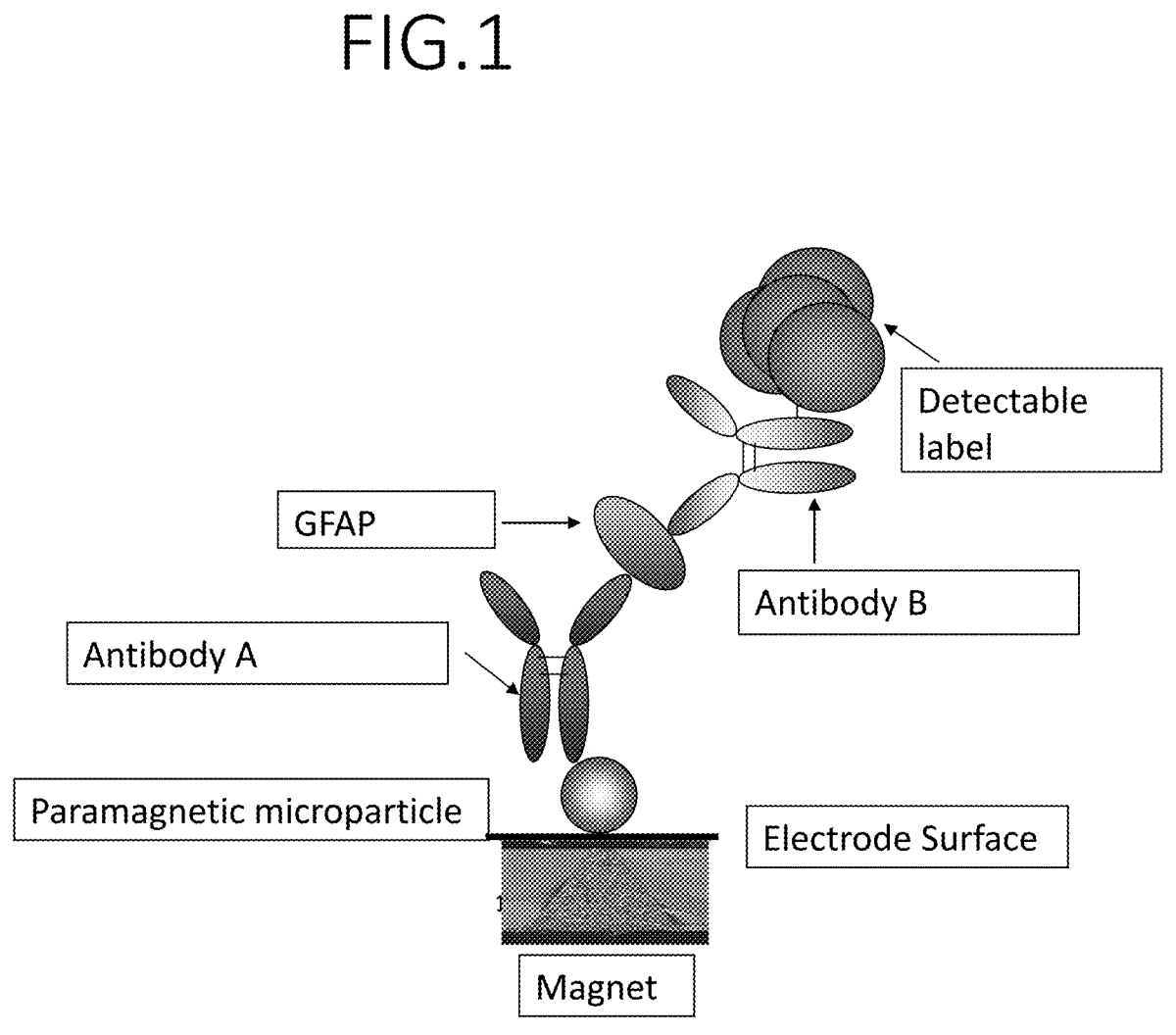

FIG. 1 shows a GFAP assay using a paramagnetic microparticle (e.g., a magnetically susceptible bead) that is magnetically captured and retained on a magnet (e.g., a magnetic immunosensor). Monoclonal antibody pairs, such as Antibody A, as a capture monoclonal antibody, and Antibody B, as a detection monoclonal antibody, were used. Antibody A and Antibody B are exemplary anti-GFAP antibodies that were internally developed at Abbott Laboratories (Abbott Park, IL). A biotin linker is conjugated to Antibody A using routine techniques known in the art. Antibody A comprising the biotin linker is coated (e.g., immobilized) on the paramagnetic particle also using routine techniques known in the art. The paramagnetic particles used were Invitrogen Dynabeads™ MyOne™ Streptavidin T1 available from ThermoFisher (Waltham, MA), which are uniform and superparatmagnetic beads which contain a monolayer of recombinant streptavidin covalently coupled on the surface of the beads. The paramagnetic particles coated with Antibody A were printed and dried on a sensor chip in a cartridge for use in a point-of-care device. Antibody B was labeled with a detectable label (e.g., alkaline phosphatase) using routine techniques known in the art. At least one detectably labeled Antibody B was printed and dried on the same sensor chip that contained the printed and dried paramagnetic particles coated with Antibody A.

Fingerstick blood samples (whole blood) were obtained from normal subjects. The samples were inserted into a cartridge for use with a point-of-care device. The printed paramagnetic particles coated with Antibody A and biotin linker and the detectably labeled Antibody B were reconstituted and mixed with the whole blood sample. Complexes comprising paramagnetic particles coated with Antibody A-GFAP-detectably labeled Antibody B were formed. A magnet contained on the sensor chip (i.e., under the chip, that collectively comprises the magnetic immunosensor) captured and retained the complexes and the amount of GFAP was determined using an i-STAT Alinity instrument (or i-STAT1 instrument). The techniques described in U.S.

Pat. Nos. 9,233,370, 9,958,440, 10,145,843 and International Patent Publication Nos.: WO18107016, WO18107015, WO18107007, WO18107009, WO18107012, WO18107013, WO21211331, and WO21211332, the contents of which are herein incorporated by reference. also were employed, the contents of which are herein incorporated by reference. The total assay time was about 10 minutes. The limit of quantification of the magnetic GFAP assay was ≤10 pg/mL. In contrast, the limit of quantification of the commercially available i-STAT® IBI Plasma test (Abbott Laboratories) for use on the i-STAT® Alinity instrument is about 23 pg/mL.

Example 2

Figure 10:
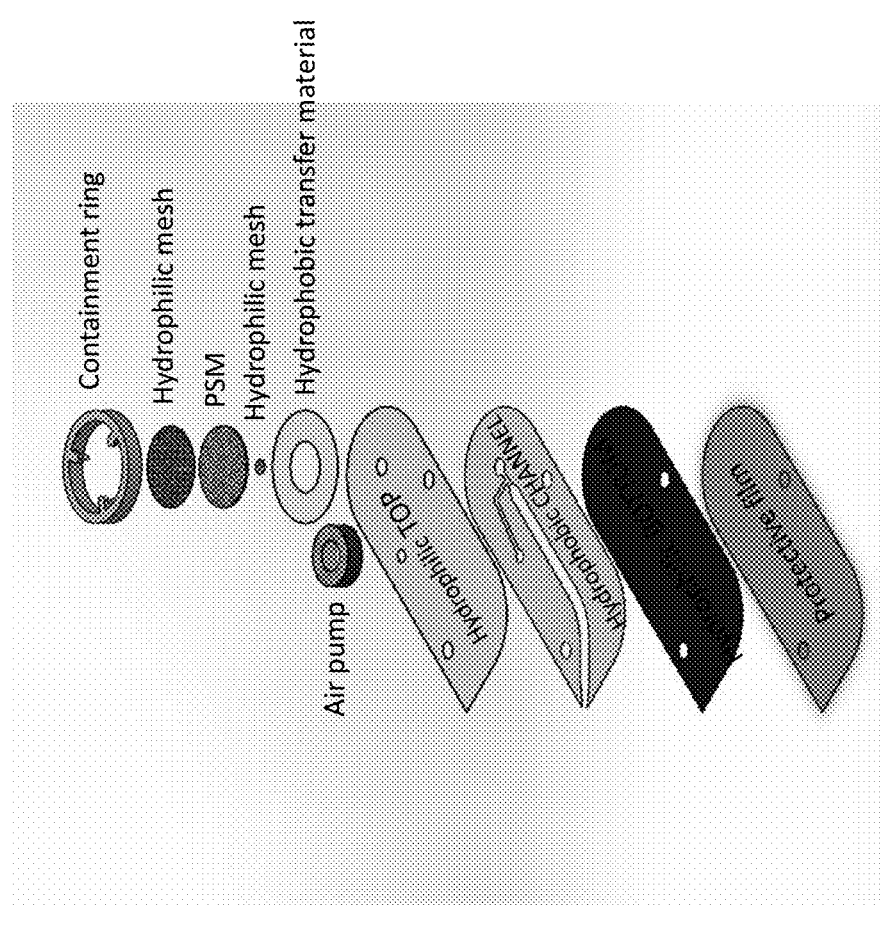
FIG. 10 shows an apparatus that can be used as a plasma separation device as described in Example 2.

FIG. 10 shows an apparatus that can be used as a plasma separation device in the methods and systems described herein. The apparatus comprises a hydrophilic top layer, a hydrophobic layer with a microchannel having a first and second end, a hydrophilic bottom layer and a protection film. The hydrophilic top layer is adherent to the hydrophobic layer and the protection film is adherent to the bottom hydrophilic layer which is adherent to the hydrophobic layer. The top layer comprises a sample inlet. The sample inlet is surrounded by a circular hydrophobic transfer tape. On top of the hydrophobic transfer tape is a plasma separation membrane (PSM) which is flanked on both its top and bottom surfaces with a hydrophilic mesh. The hydrophilic mesh positioned above or on top of the PSM assists in spreading the sample. The hydrophilic mesh positioned beneath or below the PSM assists facilitating the processing of the blood sample or blood product to the hydrophobic layer. A containment ring, to assist in containing the sample encompasses the PSM, the hydrophilic meshes and the transfer tape. The hydrophobic layer contains an opening (e.g., first opening) directly underneath the sample inlet. The opening on the hydrophobic layer is connected to a first end of the microchannel. Plasma flows from the opening (e.g., first opening) at the first towards the second opening at the second (e.g., opposite) end. The apparatus also contains an air pump for circulating air through the device.

Example 3

Blood samples were obtained from 6 donors over 4 different test days. Each blood sample was manipulated to provide several different samples. Specifically, the samples were:

1. Tested without any manipulation.
2. Augmented with native GFAP antigen.
3. Spiked with recombinant GFAP antigen.

The samples were tested at nominal hematocrit (37-45% Packed Cell Volume (PCV)) and modified hematocrit (low: 30, 33% PCV; high: 44, 50, 52, 54 and 55% PCV)

The samples were drawn into 6 mL $K_2$-EDTA tubes and the plasma was separated by:

1. Centrifugation; or
2. Using a pre-evacuated tube having an inlet and outlet end. The tube had a blood holding chamber at the inlet end and a serum holding chamber at the outlet end. The tube also had a filter assembly between the blood holding chamber at the inlet end and the serum holding chamber at the outlet end. An example of such a device that can be used is described in U.S. Pat. No. 9,427,707.

Once plasma was obtained it was placed in the sample well of a cartridge and tested in a point-of-care device, such as the i-STAT® device of Abbott Laboratories (Abbott Park, IL).

The results confirmed that both native and recombinant GFAP could be detected by the point-of-care device using plasma produced using the pre-evacuated tube.

Example 4

This study was designed to compare the levels of GFAP in capillary and venous blood samples obtained from normal subjects. Five (5) subjects were enrolled in this study. Each subject experienced two (2) blood draws. The first draw was a venous blood draw performed by a phlebotomist using routine venous blood collection techniques known in the art. The second blood draw was a capillary blood draw and was performed using the TAP II sample collection device which is commercially available from YourBio Health (Medford, MA), pursuant to the manufacturer's instructions. The TAP II sample collection device is described in WO 2020/223710, the contents of which are herein incorporated by reference.

A portion of each of the venous and capillary samples obtained from every subject was centrifuged to obtain plasma. For each subject, venous whole blood and plasma samples and capillary whole blood and plasma samples were tested.

The venous whole blood and plasma samples and the capillary whole blood and plasma samples for each of the five (5) subjects were tested using the magnetic GFAP assay described in Example 1 and shown in FIG. 1.

Figure 12:
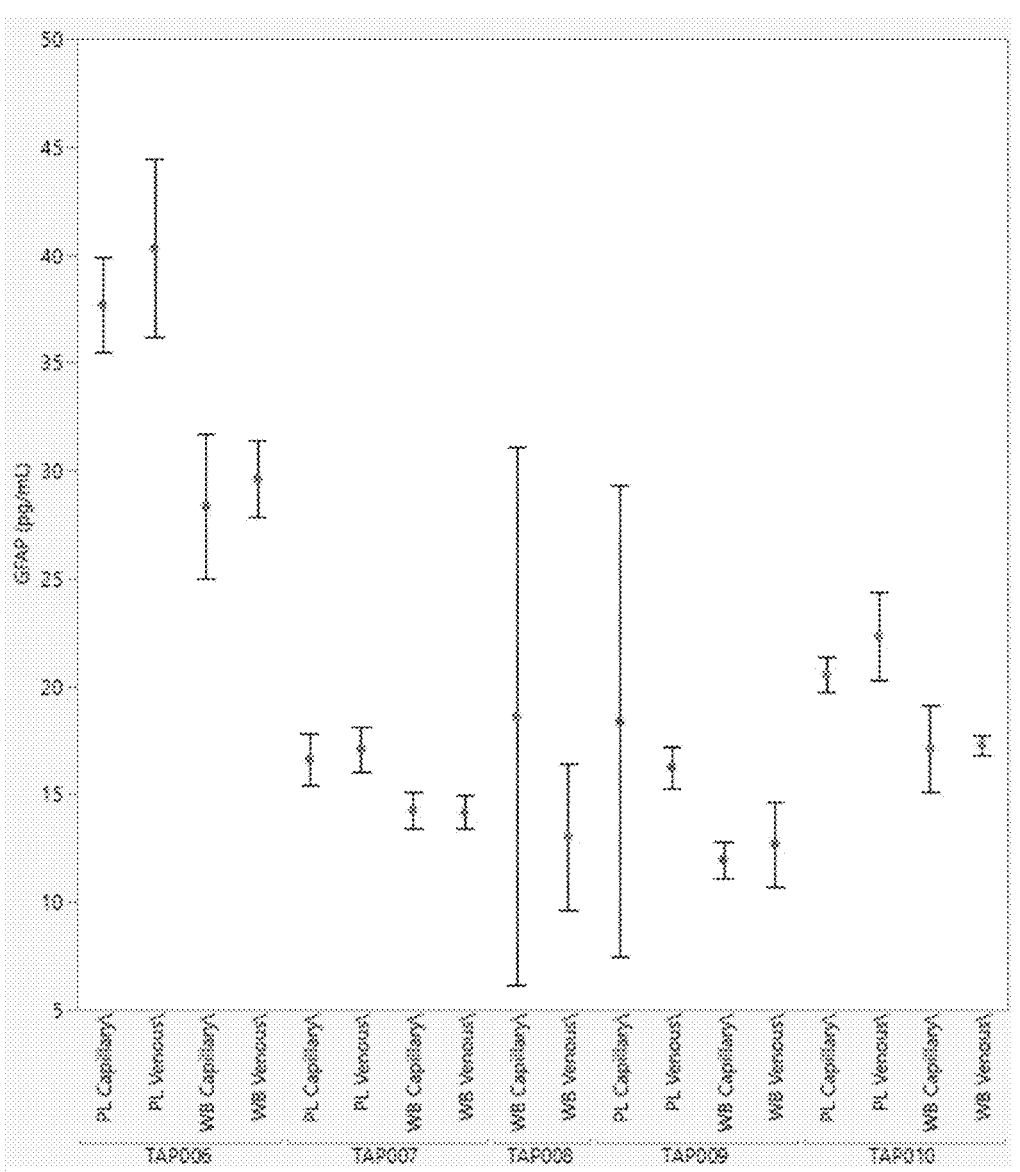
FIG. 12 shows the mean GFAP (pg/mL) concentration readings with 95% confidence intervals by donor and source as described in Example 4.

As shown in FIG. 12, the levels of GFAP in the venous whole blood and plasma samples read similar to the levels of GFAP in capillary whole blood and plasma samples (e.g., exhibited about a 1.0 to about a 0.85 (1.0:0.85) correlation between venous whole blood and plasma to capillary whole blood and plasma).

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the non-limiting examples described herein.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

For reasons of completeness, various aspects of the disclosure are set out in the following numbered clauses:

Clause 1. An assay for measuring an amount of glial fibrillary acid protein (GFAP) in a biological sample obtained from a subject, comprising:

performing an assay for GFAP, wherein the assay comprises:

(a) contacting the sample with a cartridge comprising at least one magnetic immunosensor and: (i) at least one first specific binding partner comprising at least one anti-GFAP antibody which specifically binds to GFAP in the sample that is printed on the cartridge, wherein said at least one first specific binding partner is immobilized on at least one magnetically susceptible bead; and (ii) at least one second specific binding partner comprising a detectable label that is printed on the cartridge, thereby producing one or more complexes comprising the first specific binding partner-GFAP-second specific binding partner;

(b) magnetically capturing and retaining the bead containing the complexes on at least one magnetic immunosensor in a cartridge contained in a point-of-care device; and (c) assessing a signal from the complexes, wherein the amount of detectable signal from the detectable label indicates the amount of GFAP in the sample, wherein the cartridge is used in a point-of-care device, and further wherein the assay exhibits at least a 5-fold increase in sensitivity compared to an assay that does not immobilize the first specific binding partner on a magnetically susceptible bead and magnetically capture and retain the bead containing the complexes on at least one magnetic immunosensor in a cartridge contained in a point-of-care device.

Clause 2. The assay of clause 1, wherein the assay further comprises the step of washing unbound sample that is not magnetically captured and retained on the at least one magnetic immunosensor.

Clause 3. The assay of clause 1 or clause 2, wherein the magnetic immunosensor comprises a sensing electrode on a substantially planar chip and a magnetic layer on the chip.

Clause 4. The assay of clause 3, wherein the magnetic layer comprises high-field magnetic particles.

Clause 5. The assay of any of clauses 1-4, wherein the assay further comprises measuring an amount of ubiquitin carboxy-terminal hydrolase L1 (UCH-L1) in the sample using a non-magnetic assay.

Clause 6. The assay of any of clauses 1-5, wherein the assay exhibits at least a 7-fold, at least an 8-fold, at least a 9-fold, at least a 10-fold, at least a 11-fold, at least a 12-fold, at least a 13-fold, at least a 14-fold, or at least a 15-fold increase in sensitivity compared to an assay that does not immobilize the first specific binding partner on a magnetically susceptible bead and magnetically capture and retain the bead containing the complexes on at least one magnetic immunosensor in a cartridge contained in a point-of-care device.

Clause 7. The assay of any of clauses 1-6, wherein the assay is used to aid in a diagnosis and evaluation of a subject that has sustained or may have sustained an injury to the head.

Clause 8. The assay of clause 7, wherein the subject is diagnosed as having an acquired brain injury, or an acquired brain injury that is a traumatic brain injury.

Clause 9. The assay of clause 8, wherein the subject is treated for the acquired brain injury, or acquired brain injury that is a traumatic brain injury.

Clause 10. The assay of any of clauses 1-9, wherein the sample is collected using a microsampling device or a fingerstick device.

Clause 11. The assay of any of clauses 1-10, wherein the sample is venous blood, capillary blood, fingerstick blood, or a combination thereof.

Clause 12. The assay of any of clauses 1-11, wherein the sample is processed prior to performing the assay.

Clause 13. The assay of clause 12, wherein the sample is processed by plasma separation.

Clause 14. The assay of clause 13, wherein the sample is processed using a plasma separation device.

Clause 15. The assay of clause 14, wherein the plasma separation device is: (a) incorporated into or operably linked to the point-of-care device; or (b) separate from the point-of-care device.

Clause 16. The assay of any of clauses 5-15, wherein the amount of GFAP is communicated by displaying on the device.

Clause 17. A system comprising:

an assay for glial fibrillary acidic protein (GFAP), wherein the assay comprises contacting a biological sample from a subject with: (i) at least one first specific binding partner comprising at least one anti-GFAP antibody which specifically binds to GFAP in the sample that is printed on the cartridge, wherein said at least one first specific binding partner is immobilized on at least one magnetically susceptible bead; and (ii) at least one second specific binding partner comprising a detectable label that is printed on the cartridge, thereby producing one or more complexes comprising the first specific binding partner-GFAP-second specific binding partner;

a point-of-care device comprising a cartridge comprising at least one magnetic immunosensor, wherein the device (a) determines an amount of GFAP in a sample obtained from the subject by magnetically capturing and retaining the bead containing the complexes on the at least one magnetic immunosensor; and (b) assesses a signal from the complexes, wherein the amount of detectable signal from the detectable label indicates the amount of GFAP in the sample, wherein the assay exhibits at least a 5-fold increase in sensitivity compared to an assay that does not immobilize the first specific binding partner on a magnetically susceptible bead and magnetically capture and retain the bead containing the complexes on at least one magnetic immunosensor in a cartridge contained in a point-of-care device.

Clause 18. The system of clause 17, wherein the magnetic immunosensor comprises a sensing electrode on a substantially planar chip and a magnetic layer on the chip.

Clause 19. The system of clause 18, wherein the magnetic layer comprises high-field magnetic particles. Clause 20. The system of any of clauses 17-19, wherein the system further comprises an assay for measuring an amount of ubiquitin carboxy-terminal hydrolase L1 (UCH-L1) in the sample using a non-magnetic assay.

Clause 21. The system of any of clauses 17-20, wherein the assay exhibits at least a 7-fold, at least an 8-fold, at least a 9-fold, at least a 10-fold, at least a 11-fold, at least a 12-fold, at least a 13-fold, at least a 14-fold, or at least a 15-fold increase in sensitivity compared to an assay that does not immobilize the first specific binding partner on a magnetically susceptible bead and magnetically capture and retain the bead containing the complexes on at least one magnetic immunosensor in a cartridge contained in a point-of-care device.

Clause 22. The system of any of clauses 17-21, wherein the assay is used to aid in a diagnosis and evaluation of a subject that has sustained or may have sustained an injury to the head.

Clause 23. The system of clause 22, wherein the subject is diagnosed as having a traumatic brain injury.

Clause 24. The system of clause 23, wherein the subject is treated for the traumatic brain injury.

Clause 25. The system of any of clauses 17-24, wherein the sample is collected using a microsampling device or a fingerstick device.

Clause 26. The system of any of clauses 17-25, wherein the sample is venous blood, capillary blood, fingerstick blood, or a combination thereof.

Clause 27. The system of any of clauses 17-26, wherein the sample is processed prior to performing the assay.

Clause 28. The assay of clause 27, wherein the sample is processed by plasma separation.

Clause 29. The system of clause 28, wherein the sample is processed using a plasma separation device.

Clause 30. The system of clause 29, wherein the plasma separation device is: (a) incorporated into or operably linked to the point-of-care device; or (b) separate from the point-of-care device.

Clause 31. The system of any of clauses 20-30, wherein the amount of GFAP is communicated by displaying on the device.

Clause 32. A cartridge comprising:

a magnet;

an area comprising printed paramagnetic particles coated with an anti-GFAP antibody; and an area comprising a plurality of printed detectably labeled anti-GFAP antibodies, wherein the cartridge is used in a point-of-care device.

Clause 33. The cartridge of clause 32, wherein the area comprising the plurality of detectably labeled anti-GFAP antibodies is in the same area containing the printed paramagnetic particles coated with the anti-GFAP antibody.

Clause 34. The cartridge of clause 32, wherein the area comprising the plurality of detectably labeled anti-GFAP antibodies is adjacent to the area containing the printed paramagnetic particles coated with the anti-GFAP antibody.

Clause 35. The assay of clause 16, wherein the assay, prior to displaying the amount of the GFAP on the device, further comprises:

a. determining the amount or of GFAP in the capillary blood sample;

b. selecting a conversion factor for comparing the amount of GFAP in the sample with the amount of the GFAP in venous blood, wherein the conversion factor is a static correlation ratio, a dynamic ratio or a combination thereof; and c. normalizing the amount of GFAP in the sample with the amount of GFAP from venous blood by applying the conversion factor selected in step b) to the amount of GFAP in the sample.

Clause 36. The assay of clause 35, wherein the normalized amount of GFAP is displayed by the device.

Clause 37. The assay of any of clause 35 or clause 36, wherein the conversion factor is from about 1.2:1.0 to about 1.0:0.5.

Clause 38. The assay of clause 35 or clause 26, wherein the conversion factor is from about 1.0:0.85.

---

SEQUENCE LISTING

```
Sequence total quantity: 5
SEQ ID NO: 1              moltype = AA  length = 223
FEATURE                  Location/Qualifiers
REGION                   1..223
                         note = Synthetic
source                   1..223
                         mol_type = protein
                         organism = synthetic construct
SEQUENCE: 1
MQLKPMEINP EMLNKVLSRL GVAGQWRFVD VLGLEEESLG SVPAPACALL LLFPLTAQHE   60
NFRKKQIEEL KGQEVSPKVY FMKQTIGNSC GTIGLIHAVA NNQDKLGFED GSVLKQFLSE  120
TEKMSPEDRA KCFEKNEAIQ AAHDAVAQEG QCRVDDKVNF HFILFNNVDG HLYELDGRMP  180
FPVNHGASSE DTLLKDAAKV CREFTEREQG EVRFSAVALC KAA                    223

SEQ ID NO: 2              moltype = AA  length = 432
FEATURE                  Location/Qualifiers
REGION                   1..432
                         note = Synthetic
source                   1..432
                         mol_type = protein
                         organism = synthetic construct
SEQUENCE: 2
MERRRITSAA RRSYVSSGEM MVGGLAPGRR LGPGTRLSLA RMPPPLPTRV DFSLAGALNA   60
GFKETRASER AEMMELNDRF ASYIEKVRFL EQQNKALAAE LNQLRAKEPT KLADVYQAEL  120
RELRLRLDQL TANSARLEVE RDNLAQDLAT VRQKLQDETN LRLEAENNLA AYRQEADEAT  180
LARLDLERKI ESLEEEIRFL RKIHEEEVRE LQEQLARQQV HVELDVAKPD LTAALKEIRT  240
QYEAMASSNM HEAEEWYRSK FADLTDAAAR NAELLRQAKH EANDYRRQLQ SLTCDLESLR  300
GTNESLERQM REQEERHVRE AASYQEALAR LEEEGQSLKD EMARHLQEYQ DLLNVKLALD  360
IEIATYRKLL EGEENRITIP VQTFSNLQIR ETSLDTKSVS EGHLKRNIVV KTVEMRDGEV  420
IKESKQEHKD VM                                                     432

SEQ ID NO: 3              moltype = AA  length = 6
FEATURE                  Location/Qualifiers
REGION                   1..6
                         note = Synthetic
source                   1..6
```

-continued

```
                        mol_type = protein
                        organism = synthetic construct
SEQUENCE: 3
HHHHHH                                                                    6

SEQ ID NO: 4           moltype = AA  length = 5
FEATURE                Location/Qualifiers
REGION                 1..5
                       note = Synthetic
source                 1..5
                       mol_type = protein
                       organism = synthetic construct
SEQUENCE: 4
DDDDK                                                                     5

SEQ ID NO: 5           moltype = AA  length = 6
FEATURE                Location/Qualifiers
REGION                 1..6
                       note = Synthetic
source                 1..6
                       mol_type = protein
                       organism = synthetic construct
SEQUENCE: 5
ADDDDK                                                                    6
```

What is claimed is:

1. An assay for measuring an amount of glial fibrillary acid protein (GFAP) in a biological sample obtained from a subject, comprising:

performing an assay for GFAP, wherein the assay comprises: (a) contacting the sample with a cartridge comprising at least one magnetic immunosensor and (i) at least one first specific binding partner comprising at least one anti-GFAP antibody which is configured to specifically bind to GFAP in the sample, wherein the anti-GFAP antibody that is configured to be printed on the cartridge, wherein said at least one first specific binding partner is configured to be immobilized on at least one magnetically susceptible bead;

and (ii) at least one second specific binding partner comprising a detectable label that is configured to be printed on the cartridge, thereby producing one or more complexes comprising the first specific binding partner-GFAP-second specific binding partner;

(b) said assay configured for magnetically capturing and retaining the bead containing the complexes using the at least one magnetic immunosensor; and (c)) said assay configured for assessing a signal from the complexes, wherein the amount of detectable signal from the detectable label is configured to indicate the amount of GFAP in the sample, wherein the cartridge is used in a point-of-care device, and further wherein the assay is configured to exhibit at least a 5-fold increase in sensitivity compared to an assay that does not immobilize the first specific binding partner on a magnetically susceptible bead and magnetically capture and retain the bead containing the complexes on at least one magnetic immunosensor in a cartridge used in a point-of-care device.

2. The assay of claim 1, wherein the assay further comprises the step of washing unbound sample that is not magnetically captured and retained on the at least one magnetic immunosensor.

3. The assay of claim 1, wherein the magnetic immunosensor comprises a sensing electrode on a substantially planar chip and a magnetic layer on the chip.

4. The assay of claim 3, wherein the magnetic layer comprises high-field magnetic particles.

5. The assay of claim 1, wherein the assay further comprises measuring an amount of ubiquitin carboxy-terminal hydrolase L1 (UCH-L1) in the sample using a non-magnetic assay.

6. The assay of claim 1, wherein the assay exhibits at least a 7-fold, at least an 8-fold, at least a 9-fold, at least a 10-fold, at least a 11-fold, at least a 12-fold, at least a 13-fold, at least a 14-fold, or at least a 15-fold increase in sensitivity compared to an assay that does not immobilize the first specific binding partner on a magnetically susceptible bead and magnetically capture and retain the bead containing the complexes on at least one magnetic immunosensor in a cartridge contained in a point-of-care device.

7. The assay of claim 1, wherein the assay is used to aid in a diagnosis and evaluation of a subject that has sustained or may have sustained an injury to the head.

8. The assay of claim 7, wherein the subject is diagnosed as having a traumatic brain injury.

9. The assay of claim 8, wherein the subject is treated for the traumatic brain injury.

10. The assay of claim 1, wherein the sample is collected using a microsampling device or a fingerstick device.

11. The assay of claim 1, wherein the sample is venous blood, capillary blood, fingerstick blood, or a combination thereof.

12. The assay of claim 1, wherein the sample is processed prior to performing the assay.

13. The assay of claim 12, wherein the sample is processed by plasma separation.

14. The assay of claim 13, wherein the sample is processed using a plasma separation device.

15. The assay of claim 14, wherein the plasma separation device is: (a) incorporated into or operably linked to the point-of-care device; or (b) separate from the point-of-care device.

16. The assay of claim 5, wherein the amount of GFAP is communicated by displaying on the device.

17. A system comprising: an assay for glial fibrillary acidic protein (GFAP), wherein the assay comprises contacting a biological sample from a subject with a cartridge comprising at least one magnetic immunosensor and (i) at least one first specific binding partner comprising at least one anti-GFAP antibody w which is configured to specifically bind to GFAP in the sample, wherein the anti-GFAP antibody that is configured to be printed on the cartridge, wherein said at least one first specific binding partner is configured to be immobilized on at least one magnetically susceptible bead;

and (ii) at least one second specific binding partner comprising a detectable label that is configured to be printed on the cartridge, thereby producing one or more complexes comprising the first specific binding partner-GFAP-second specific binding partner;

a point-of-care device comprising the cartridge, wherein the device (a) is configured to determines an amount of GFAP in a sample obtained from the subject by magnetically capturing and retaining the bead containing the complexes on the at least one magnetic immunosensor; and (b) is configured to assess a signal from the complexes, wherein the amount of detectable signal from the detectable label is configured to indicate the amount of GFAP in the sample, wherein the assay is configured to exhibit at least a 5-fold increase in sensitivity compared to an assay that does not immobilize the first specific binding partner on a magnetically susceptible bead and magnetically capture and retain the bead containing the complexes on at least one magnetic immunosensor in a cartridge contained in a point-of-care device.

18. The system of claim 17, wherein the magnetic immunosensor comprises a sensing electrode on a substantially planar chip and a magnetic layer on the chip.

19. The system of claim 18, wherein the magnetic layer comprises high-field magnetic particles.

20. The system of claim 17, wherein the system further comprises an assay for measuring an amount of ubiquitin carboxy-terminal hydrolase L1 (UCH-L1) in the sample using a non-magnetic assay.

21. The system of claim 17, wherein the assay exhibits at least a 7-fold, at least an 8-fold, at least a 9-fold, at least a 10-fold, at least a 11-fold, at least a 12-fold, at least a 13-fold, at least a 14-fold, or at least a 15-fold increase in sensitivity compared to an assay that does not immobilize the first specific binding partner on a magnetically susceptible bead and magnetically capture and retain the bead containing the complexes on at least one magnetic immunosensor in a cartridge contained in a point-of-care device.

22. The system of claim 17, wherein the assay is used to aid in a diagnosis and evaluation of a subject that has sustained or may have sustained an injury to the head.

23. The system of claim 22, wherein the subject is diagnosed as having a traumatic brain injury.

24. The system of claim 23, wherein the subject is treated for the traumatic brain injury.

25. The system of claim 17, wherein the sample is collected using a microsampling device or a fingerstick device.

26. The system of claim 17, wherein the sample is venous blood, capillary blood, fingerstick blood or a combination thereof.

27. The system of claim 17, wherein the sample is processed prior to performing the assay.

28. The assay of claim 27, wherein the sample is processed by plasma separation.

29. The system of claim 28, wherein the sample is processed using a plasma separation device.

30. The system of claim 29, wherein the plasma separation device is: (a) incorporated into or operably linked to the point-of-care device; or (b) separate from the point-of-care device.

31. The system of claim 20, wherein the amount of GFAP is communicated by displaying on the device.

32. The assay of claim 16, wherein the assay, prior to displaying the amount of the GFAP on the device, further comprises:

a. determining the amount or of GFAP in the capillary blood sample;

b. selecting a conversion factor for comparing the amount of GFAP in the sample with the amount of the GFAP in venous blood, wherein the conversion factor is a static correlation ratio, a dynamic ratio or a combination thereof; and c. normalizing the amount of GFAP in the sample with the amount of GFAP from venous blood by applying the conversion factor selected in step b) to the amount of GFAP in the sample.

33. The assay of claim 32, wherein the normalized amount of GFAP is displayed by the device.

34. The assay of claim 32, wherein the conversion factor is from about 1.2:1.0 to about 1.0:0.5.

35. The assay of claim 32, wherein the conversion factor is from about 1.0:0.85.

\*   \*   \*   \*   \*